(12) United States Patent
Liu et al.

(10) Patent No.: US 9,868,738 B2
(45) Date of Patent: Jan. 16, 2018

(54) DIAZINE-FUSED AMIDINES AS BACE INHIBITORS, COMPOSITIONS, AND THEIR USE

(71) Applicants: Merck Sharp & Dohme Corp., Rahway, NJ (US); Kun Liu, Needham, MA (US); Shuwen He, Edison, NJ (US); Jared N. Cumming, Winchester, MA (US); Andrew W. Stamford, Chatham, NJ (US)

(72) Inventors: Kun Liu, Needham, MA (US); Shuwen He, Edison, NJ (US); Jared N. Cumming, Winchester, MA (US); Andrew W. Stamford, Chatham, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/512,081

(22) PCT Filed: Sep. 14, 2015

(86) PCT No.: PCT/US2015/049882
§ 371 (c)(1),
(2) Date: Mar. 17, 2017

(87) PCT Pub. No.: WO2016/044120
PCT Pub. Date: Mar. 24, 2016

(65) Prior Publication Data
US 2017/0247377 A1      Aug. 31, 2017

Related U.S. Application Data

(60) Provisional application No. 62/052,783, filed on Sep. 19, 2014.

(51) Int. Cl.
*C07D 471/04*     (2006.01)

(52) U.S. Cl.
CPC ................. *C07D 471/04* (2013.01)

(58) Field of Classification Search
CPC .................................................. C07D 471/04
See application file for complete search history.

(56) References Cited

U.S. PATENT DOCUMENTS

| | | |
|---|---|---|
| 7,763,609 B2 | 7/2010 | Zhu et al. |
| 8,183,252 B2 | 5/2012 | Zhu et al. |
| 8,557,826 B2 | 10/2013 | Stamford et al. |
| 8,563,543 B2 | 10/2013 | Scott et al. |
| 8,569,310 B2 | 10/2013 | Iserloh et al. |
| 8,691,831 B2 | 4/2014 | Zhu et al. |
| 8,691,833 B2 | 4/2014 | Zhu et al. |
| 8,729,071 B2 | 5/2014 | Scott et al. |
| 8,829,036 B2 | 9/2014 | Zhu et al. |
| 8,940,748 B2 | 1/2015 | Scott et al. |
| 9,029,362 B2 | 5/2015 | Scott et al. |
| 9,428,475 B2 | 8/2016 | Scott et al. |
| 9,453,034 B2 | 9/2016 | Gilbert et al. |
| 9,475,785 B2 | 10/2016 | Scott et al. |
| 2009/0305998 A1 | 12/2009 | Chen et al. |
| 2016/0367563 A1 | 12/2016 | Scott et al. |

FOREIGN PATENT DOCUMENTS

EP     2634186 A1     9/2013

OTHER PUBLICATIONS

International Search Report of PCT/US2015/049882 dated Feb. 2, 2016, 11 pages.
Pubchem. Substance Record for SID 240193350. Deposit Date: Feb. 13, 2015. [retrieved on 2()Nov. 2015]. Retrieved from the Internet. <URL:https://pubchem.ncbi.nlm.nih.gov/substance/240193350#section=Top>.
Pubchem. Substance Record for SID 76409700. Deposit Date: Jun. 12, 2009. [retrieved on Nov. 20, 2015]. Retrieved from the Internet. <URL:https://pubchem.ncbi.nlm.nih.gov/substance/76409700#section=Top>.

*Primary Examiner* — Bruck Kifle
(74) *Attorney, Agent, or Firm* — Keith D. MacMillan; John C. Todaro

(57) ABSTRACT

In its many embodiments, the present invention provides certain C-6 spirocarbocyclic iminothiadiazine compounds, including compounds Formula (I) or a tautomer thereof, and pharmaceutically acceptable salts of said compounds and said tautomers, wherein $R^{1A}$, $R^{1B}$, $R^2$, $R^A$, ring A, $R^A$, m, $L_1$, $R^L$, ring C, $R^C$, and p are as defined herein. The novel compounds of the invention are useful as BACE inhibitors and/or for the treatment and prevention of various pathologies related thereto. Pharmaceutical compositions comprising one or more such compounds (alone and in combination with one or more other active agents), and methods for their preparation and use, including for the possible treatment of Alzheimer's disease, are also disclosed.

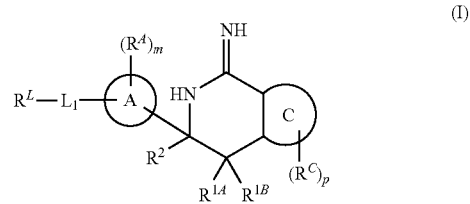

(I)

13 Claims, No Drawings

DIAZINE-FUSED AMIDINES AS BACE INHIBITORS, COMPOSITIONS, AND THEIR USE

FIELD OF THE INVENTION

This invention provides certain diazine-fused amidine compounds, and compositions comprising these compounds, as inhibitors of BACE, which may be useful for treating or preventing pathologies related thereto, including, but not limited to, Alzheimer's disease.

BACKGROUND

Amyloid beta peptide ("Aβ") is a primary component of β amyloid fibrils and plaques, which are regarded as having a role in an increasing number of pathologies. Examples of such pathologies include, but are not limited to, Alzheimer's disease, Down's syndrome, Parkinson's disease, memory loss (including memory loss associated with Alzheimer's disease and Parkinson's disease), attention deficit symptoms (including attention deficit symptoms associated with Alzheimer's disease ("AD"), Parkinson's disease, and Down's syndrome), dementia (including pre-senile dementia, senile dementia, dementia associated with Alzheimer's disease, Parkinson's disease, and Down's syndrome), progressive supranuclear palsy, cortical basal degeneration, neurodegeneration, olfactory impairment (including olfactory impairment associated with Alzheimer's disease, Parkinson's disease, and Down's syndrome), β-amyloid angiopathy (including cerebral amyloid angiopathy), hereditary cerebral hemorrhage, mild cognitive impairment ("MCI"), glaucoma, amyloidosis, type II diabetes, hemodialysis (β2 microglobulins and complications arising therefrom), neurodegenerative diseases such as scrapie, bovine spongiform encephalitis, Creutzfeld-Jakob disease, traumatic brain injury and the like.

Aβ peptides are short peptides which are made from the proteolytic break-down of the transmembrane protein called amyloid precursor protein ("APP"). Aβ peptides are made from the cleavage of APP by β-secretase activity at a position near the N-terminus of Aβ, and by gamma-secretase activity at a position near the C-terminus of Aβ. (APP is also cleaved by α-secretase activity, resulting in the secreted, non-amyloidogenic fragment known as soluble APPα.) Beta site APP Cleaving Enzyme ("BACE-1") is regarded as the primary aspartyl protease responsible for the production of Aβ by β-secretase activity. The inhibition of BACE-1 has been shown to inhibit the production of Aβ.

AD is estimated to afflict more than 20 million people worldwide and is believed to be the most common cause of dementia. AD is a disease characterized by degeneration and loss of neurons and also by the formation of senile plaques and neurofibrillary tangles. Presently, treatment of Alzheimer's disease is limited to the treatment of its symptoms rather than the example, N-methyl-D-aspartate receptor antagonists such as memantine (Namenda®, Forest Pharmaceuticals, Inc.), cholinesterase inhibitors such as donepezil (Aricept®, Pfizer), rivastigmine (Exelon®, Novartis), galantamine (Razadyne Reminyl®), and tacrine (Cognex®).

In AD, Aβ peptides, formed through β-secretase and gamma-secretase activity, can form tertiary structures that aggregate to form amyloid fibrils. Aβ peptides have also been shown to form Aβ oligomers (sometimes referred to as "Aβ aggregates" or "Abeta oligomers"). Aβ oligomers are small multimeric structures composed of 2 to 12 Aβ peptides that are structurally distinct from Aβ fibrils. Amyloid fibrils can deposit outside neurons in dense formations known as senile plaques, neuritic plaques, or diffuse plaques in regions of the brain important to memory and cognition. Aβ oligomers are cytotoxic when injected in the brains of rats or in cell culture. This Aβ plaque formation and deposition and/or Aβ oligomer formation, and the resultant neuronal death and cognitive impairment, are among the hallmarks of AD pathophysiology. Other hallmarks of AD pathophysiology include intracellular neurofibrillary tangles comprised of abnormally phosphorylated tau protein, and neuroinflammation.

Evidence suggests that Aβ, Aβ fibrils, aggregates, oligomers, and/or plaque play a causal role in AD pathophysiology. (Ohno et al., Neurobiology of Disease, No. 26 (2007), 134-145). Mutations in the genes for APP and presenilins 1/2 (PS1/2) are known to cause familial AD and an increase in the production of the 42-amino acid form of Aβ is regarded as causative. Aβ has been shown to be neurotoxic in culture and in vivo. For example, when injected into the brains of aged primates, fibrillar Aβ causes neuronal cell death around the injection site. Other direct and circumstantial evidence of the role of Aβ in Alzheimer etiology has also been published.

BACE-1 has become an accepted therapeutic target for the treatment of Alzheimer's disease. For example, McConlogue et al., J. Bio. Chem., Vol. 282, No. 36 (September 2007), have shown that partial reductions of BACE-1 enzyme activity and concomitant reductions of Aβ levels lead to a dramatic inhibition of Aβ-driven AD-like pathology, making β-secretase a target for therapeutic intervention in AD. Ohno et al. Neurobiology of Disease, No. 26 (2007), 134-145, report that genetic deletion of BACE-1 in 5XFAD mice abrogates Aβ generation, blocks amyloid deposition, prevents neuron loss found in the cerebral cortex and subiculum (brain regions manifesting the most severe amyloidosis in 5XFAD mice), and rescues memory deficits in 5XFAD mice. The group also reports that Aβ is ultimately responsible for neuron death in AD and concludes that BACE-1 inhibition has been validated as an approach for the established that inhibition or loss of β-secretase activity produces no profound phenotypic defects while inducing a concomitant reduction in Aβ. Luo et al., Nature Neuroscience, Vol. 4, No. 3, March 2001, report that mice deficient in BACE-1 have normal phenotype and abolished β-amyloid generation.

More recently, Jonsson, et al. have reported in Nature, Vol. 488, pp. 96-99 (August 2012), that a coding mutation (A673T) in the APP gene protects against Alzheimer's disease and cognitive decline in the elderly without Alzheimer's disease. More specifically, the A allele of rs63750847, a single nucleotide polymorphism (SNP), results in an alanine to threonine substitution at position 673 in APP (A673T). This SNP was found to be significantly more common in a healthy elderly control group than in an Alzheimer's disease group. The A673T substitution is adjacent to the aspartyl protease beta-site in APP, and results in an approximately 40% reduction in the formation of amyloidogenic peptides in a heterologous cell expression system in vitro. Jonsson, et al. report that an APP-derived peptide substrate containing the A673T mutation is processed 50% less efficiently by purified human BACE1 enzyme when compared to a wild-type peptide. Jonsson et al. indicate that the strong protective effect of the APP-A673T substitution against Alzheimer's disease provides proof of principle for the hypothesis that reducing the beta-cleavage of APP may protect against the disease.

BACE-1 has also been identified or implicated as a therapeutic target for a number of other diverse pathologies in which Aβ or Aβ fragments have been identified to play a causative role. One such example is in the treatment of AD-type symptoms of patients with Down's syndrome. The gene encoding APP is found on chromosome 21, which is also the chromosome found as an extra copy in Down's syndrome. Down's syndrome patients tend to acquire AD at an early age, with almost all those over 40 years of age showing Alzheimer's-type pathology. This is thought to be due to the extra copy of the APP gene found in these patients, which leads to overexpression of APP and therefore to increased levels of Aβ causing the prevalence of AD seen in this population. Furthermore, Down's patients who have a duplication of a small region of chromosome 21 that does not include the APP gene do not develop AD pathology. Thus, it is thought that inhibitors of BACE-1 could be useful in reducing Alzheimer's type pathology in Down's syndrome patients.

Another example is in the treatment of glaucoma (Guo et al., PNAS, Vol. 104, No. 33, Aug. 14, 2007). Glaucoma is a retinal disease of the eye and a major cause of irreversible blindness worldwide. Guo et al. report that Aβ colocalizes with apoptotic retinal ganglion cells time-dependent manner. The group report having demonstrated that targeting different components of the Aβ formation and aggregation pathway, including inhibition of β-secretase alone and together with other approaches, can effectively reduce glaucomatous RGC apoptosis in vivo. Thus, the reduction of Aβ production by the inhibition of BACE-1 could be useful, alone or in combination with other approaches, for the treatment of glaucoma.

Another example is in the treatment of olfactory impairment. Getchell et al., Neurobiology of Aging, 24 (2003), 663-673, have observed that the olfactory epithelium, a neuroepithelium that lines the posterior-dorsal region of the nasal cavity, exhibits many of the same pathological changes found in the brains of AD patients, including deposits of Aβ, the presence of hyperphosphorylated tau protein, and dystrophic neurites among others. Other evidence in this connection has been reported by Bacon A W, et al., Ann NY Acad Sci 2002; 855:723-31; Crino P B, Martin J A, Hill W D, et al., Ann Otol Rhinol Laryngol, 1995; 104:655-61; Davies D C, et al., Neurobiol Aging, 1993; 14:353-7; Devanand D P, et al., Am J Psychiatr, 2000; 157:1399-405; and Doty R L, et al., Brain Res Bull, 1987; 18:597-600. It is reasonable to suggest that addressing such changes by reduction of Aβ by inhibition of BACE-1 could help to restore olfactory sensitivity in patients with AD.

For compounds which are inhibitors of BACE-2, another example is in the treatment of type-II diabetes, including diabetes associated with amyloidogenesis. BACE-2 is expressed in the pancreas. BACE-2 immunoreactivity has been reported in secretory granules of beta cells, co-stored with insulin and IAPP, but lacking in the other endocrine and exocrine cell types. Stoffel et al., WO2010/063718, disclose the use of BACE-2 inhibitors in the treatment of metabolic diseases such as Type-II diabetes. The presence of BACE-2 in secretory granules of beta cells suggests that it may play a role in diabetes-associated amyloidogenesis. (Finzi, G. Franzi, et al., Ultrastruct Pathol. 2008 November-December; 32(6):246-51.)

Other diverse pathologies characterized by the formation and deposition of Aβ or fragments thereof, and/or by the presence of amyloid fibrils, oligomers, and/or plaques, include neurodegenerative diseases such as scrapie, bovine spongiform encephalitis, traumatic brain injury ("TBI"), Creutzfeld-Jakob disease and the like, type II diabetes (which is characterized by the localized accumulation of cytotoxic amyloid fibrils in the insulin producing cells of the pancreas), and amyloid angiopathy. In this regard reference can be made to the patent literature. For example, Kong et al., US2008/0015180, disclose methods and compositions for treating amyloidosis with agents that inhibit Aβ peptide formation. As another example, Loane, et al. report the targeting of amyloid precursor protein secretases as therapeutic targets targets for traumatic brain injury", Nature Medicine, Advance Online Publication, published online Mar. 15, 2009.) Still other diverse pathologies characterized by the inappropriate formation and deposition of Aβ or fragments thereof, and/or by the presence of amyloid fibrils, and/or for which inhibitor(s) of BACE are expected to be of therapeutic value are discussed further hereinbelow.

SUMMARY OF THE INVENTION

The present invention provides certain diazine-fused amidine compounds, which are collectively or individually referred to herein as "compound(s) of the invention", as described herein. The compounds of the invention are inhibitors of BACE-1 and/or BACE-2, and may be useful for treating or preventing diseases or pathologies related thereto.

In one embodiment, the compounds of the invention have the structural Formula (I):

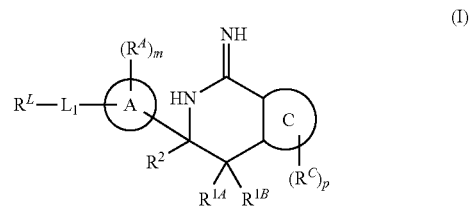

or a tautomer thereof having the structural Formula (I'):

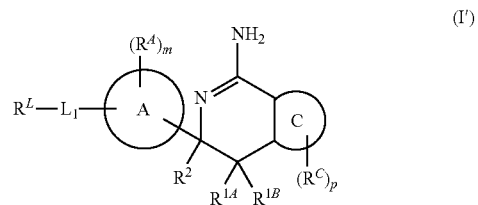

or pharmaceutically acceptable salt thereof, wherein:
-$L_1$- is a bond or the divalent moiety —C(O)NH—;
$R^{1A}$ and $R^{1B}$ are each independently selected from the group consisting of H, halogen, alkyl, and cycloalkyl,
  wherein said alkyl and said cycloalkyl are optionally substituted with one or more fluorine, and
  independently replaced with —O—, —NH—, —N(alkyl)-, —S—, —S(O)—, or —S(O)$_2$—;
$R^2$ is selected from the group consisting of H, alkyl, cycloalkyl, -alkyl-cycloalkyl, heterocycloalkyl, and -alkyl-heterocycloalkyl,
  wherein said alkyl, cycloalkyl, -alkyl-cycloalkyl, heterocycloalkyl, and -alkyl-heterocycloalkyl are optionally substituted with one or more halogen, and wherein 1 to 2 non-adjacent, non-terminal carbon atoms in said alkyl are optionally independently replaced with —O—, —NH—, —N(alkyl)-, —S—, —S(O)—, or —S(O)$_2$—;

ring A is selected from the group consisting of aryl and heteroaryl;

m is 0 or more, with the proviso that the value of m does not exceed the number of available substitutable hydrogen atoms on ring A;

each $R^A$ (when present) is independently selected from the group consisting of halogen, oxo, —OH, —CN, alkyl, —O-alkyl, and cycloalkyl, wherein said alkyl, —O-alkyl, and cycloalkyl of $R^A$ are each optionally independently unsubstituted or substituted with one or more fluorine, and wherein 1 to 2 non-adjacent, non-terminal carbon atoms in said alkyl are optionally independently replaced with —O—, —NH—, —N(alkyl)-, —S—, —S(O)—, or —S(O)$_2$—;

$R^L$ is alkyl, wherein said alkyl is optionally further substituted with one or more halogen, and wherein 1 to 2 non-adjacent, non-terminal carbon atoms in said alkyl are optionally independently replaced with —O—, —NH—, —N(alkyl)-, —S—, —S(O)—, or —S(O)$_2$—;

or, alternatively, $R^L$ is a moiety having the formula

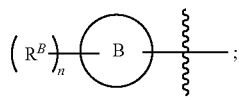

wherein ring B is selected from the group consisting of aryl, heteroaryl, cycloalkyl, and heterocycloalkyl;

n is 0 or more, with the proviso that the value of n does not exceed the number of available substitutable hydrogen atoms on ring b; and each $R^B$ (when present) is independently selected from the group consisting of halogen, oxo, —OH, —CN, —SF$_5$, —OSF$_5$, —OR$^{3B}$, —SR$^{3B}$, alkyl, alkenyl, alkynyl, cycloalkyl, -alkyl-cycloalkyl, heterocycloalkyl, -alkyl-heterocycloalkyl, aryl, and heteroaryl, wherein said alkyl, alkenyl, alkynyl, cycloalkyl, -alkyl-cycloalkyl, heterocycloalkyl, -alkyl-heterocycloalkyl, aryl, and heteroaryl of $R^B$ are each optionally independently unsubstituted or substituted with one or more groups independently selected from $R^4$, independently replaced with —O—, —NH—, —N(alkyl)-, —S—, —S(O)—, or —S(O)$_2$—;

ring C is selected from the group consisting of pyrazinyl, pyrimidinyl, and pyridazinyl;

p is 0 or more, with the proviso that the value of p does not exceed the number of available substitutable hydrogen atoms on ring C; and each $R^C$ (when present) is independently selected from the group consisting of alkyl and cycloalkyl, wherein said alkyl and cycloalkyl are each optionally substituted with one to three fluorine, and wherein 1 to 2 non-adjacent, non-terminal carbon atoms in said alkyl are optionally independently replaced with —O—, —NH—, —N(alkyl)-, —S—, —S(O)—, or —S(O)$_2$—;

each $R^{3B}$ is independently selected from the group consisting of H, alkyl, alkenyl, alkynyl, cycloalkyl, -alkyl-cycloalkyl, heterocycloalkyl, and -alkyl-heterocycloalkyl, wherein each said alkyl, alkenyl, alkynyl, cycloalkyl, -alkyl-cycloalkyl, heterocycloalkyl, and -alkyl-heterocycloalkyl of $R^{3B}$ is unsubstituted or optionally substituted with one or more fluorine, and wherein 1 to 2 non-adjacent, non-terminal carbon atoms in said alkyl are optionally independently replaced with —O—, —NH—, —N(alkyl)-, —S—, —S(O)—, or —S(O)$_2$—; and each $R^4$ (when present) is independently selected from the group consisting of halogen, —OH, —CN, alkyl, alkoxy, cycloalkyl, -alkyl-cycloalkyl, —O-cycloalkyl, -heterocycloalkyl, and -alkyl-heterocycloalkyl, wherein each said alkyl, alkoxy, cycloalkyl, -alkyl-cycloalkyl, —O-cycloalkyl, -heterocycloalkyl, and -alkyl-heterocycloalkyl are optionally substituted with one or more fluorine, and wherein 1 to 2 non-adjacent, non-terminal carbon atoms in said alkyl are optionally independently replaced with —O—, —NH—, —N(alkyl)-, —S—, —S(O)—, or —S(O)$_2$—.

In other embodiments, the invention provides compositions, including pharmaceutical compositions, comprising one or more compounds of the invention (e.g., one compound of the invention), or a tautomer thereof, or a pharmaceutically acceptable salt or solvate of said compound(s) and/or said tautomer(s), optionally together with one or more additional therapeutic agents, optionally in an acceptable (e.g., pharmaceutically acceptable) carrier or diluent.

In other embodiments, the invention provides various methods of treating, preventing, ameliorating, and/or delaying the onset of an Aβ pathology and/or a symptom or symptoms more compounds of the invention, or a tautomer thereof, or pharmaceutically acceptable salt or solvate of said compound(s) and/or said tautomer(s), to a patient in need thereof. Such methods optionally additionally comprise administering an effective amount of one or more additional therapeutic agents, simultaneously or sequentially, suitable for treating the patient being treated.

These and other embodiments of the invention, which are described in detail below or will become readily apparent to those of ordinary skill in the art, are included within the scope of the invention.

DETAILED DESCRIPTION

For each of the following embodiments, any variable not explicitly defined in the embodiment is as defined in Formula (I) or (IA). In each of the embodiments described herein, each variable is selected independently of the other unless otherwise noted.

In one embodiment, the compounds of the invention have the structural Formula (IA):

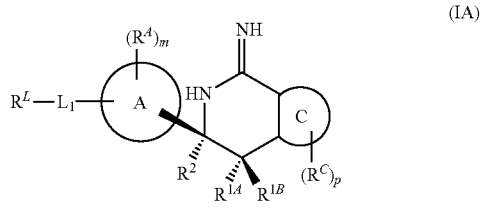

or a tautomer thereof having the structural Formula (IA'):

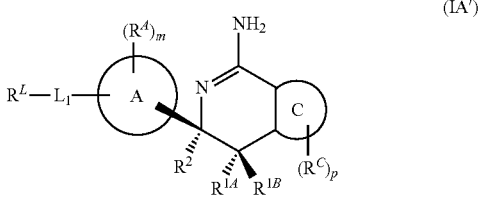

or pharmaceutically acceptable salt thereof, wherein each variable is as described in Formula (I).

In one embodiment, in each of Formulas (I), (I'), (IA), and (IA'): and —CH$_2$CH$_2$OCH$_3$.

In one embodiment, in each of Formulas (I), (I'), (IA), and (IA'):
R$^{1A}$ is selected from the group consisting of H, fluorine, methyl, and cyclopropyl.

In one embodiment, in each of Formulas (I), (I'), (IA), and (IA'):
R$^{1A}$ is selected from the group consisting of H and fluorine.

In one embodiment, in each of Formulas (I), (I'), (IA), and (IA'):
R$^{1B}$ is selected from the group consisting of H, fluorine, methyl, ethyl, cyclopropyl, and —CH$_2$CH$_2$OCH$_3$.

In one embodiment, in each of Formulas (I), (I'), (IA), and (IA'):
R$^{1B}$ is selected from the group consisting of H, fluorine, methyl, and cyclopropyl.

In one embodiment, in each of Formulas (I), (I'), (IA), and (IA'):
R$^{1B}$ is selected from the group consisting of H and fluorine.

In one embodiment, in each of Formulas (I), (I'), (IA), and (IA'):
R$^{1A}$ is selected from the group consisting of H, fluorine, methyl, ethyl, cyclopropyl, and —CH$_2$CH$_2$OCH$_3$; and
R$^{1B}$ is selected from the group consisting of H, fluorine, methyl, ethyl, cyclopropyl, and —CH$_2$CH$_2$OCH$_3$.

In one embodiment, in each of Formulas (I), (I'), (IA), and (IA'):
R$^{1A}$ is selected from the group consisting of H, fluorine, methyl, and cyclopropyl; and
R$^{1B}$ is selected from the group consisting of H, fluorine, methyl, and cyclopropyl.

In one embodiment, in each of Formulas (I), (I'), (IA), and (IA'):
R$^{1A}$ is selected from the group consisting of H, fluorine, methyl, and cyclopropyl; and
R$^{1B}$ is selected from the group consisting of H and fluorine.

In one embodiment, in each of Formulas (I), (I'), (IA), and (IA'):
R$^{1A}$ is selected from the group consisting of H and fluorine; and
R$^{1B}$ is selected from the group consisting of H and fluorine.

In one embodiment, in each of Formulas (I), (I'), (IA), and (IA'):
R$^{1A}$ and R$^{1B}$ are H.

In one embodiment, in each of Formulas (I), (I'), (IA), and (IA'):
R$^{1A}$ and R$^{1B}$ are fluorine.

In one embodiment, in each of Formulas (I), (I'), (IA), and (IA'):
R$^2$ is selected from the group consisting of H, methyl, ethyl, cyclopropyl, —CH$_2$-cyclopropyl, —CH$_2$F, —CHF$_2$, —CF$_3$, and —CH$_2$OCH$_3$.

R$^2$ is selected from the group consisting of methyl, cyclopropyl, —CH$_2$F, and —CHF$_2$.

In one embodiment, in each of Formulas (I), (I'), (IA), and (IA'):
R$^2$ is selected from the group consisting of methyl and —CHF$_2$.

In one embodiment, in each of Formulas (I), (I'), (IA), and (IA'):
R$^{1A}$ is selected from the group consisting of H, fluorine, methyl, and cyclopropyl; and
R$^{1B}$ is selected from the group consisting of H, fluorine, methyl, and cyclopropyl; and
R$^2$ is selected from the group consisting of methyl and —CHF$_2$.

In one embodiment, in each of Formulas (I), (I'), (IA), and (IA'):
R$^{1A}$ is selected from the group consisting of H, fluorine, methyl, and cyclopropyl; and
R$^{1B}$ is selected from the group consisting of H and fluorine;
R$^2$ is selected from the group consisting of methyl and —CHF$_2$.

In one embodiment, in each of Formulas (I), (I'), (IA), and (IA'):
R$^{1A}$ is selected from the group consisting of H and fluorine;
R$^{1B}$ is selected from the group consisting of H and fluorine; and
R$^2$ is selected from the group consisting of methyl and —CHF$_2$.

In one embodiment, in each of Formulas (I), (I'), (IA), and (IA'):
R$^{1A}$ and R$^{1B}$ are H; and
R$^2$ is selected from the group consisting of methyl and —CHF$_2$.

In one embodiment, in each of Formulas (I), (I'), (IA), and (IA'):
R$^{1A}$ and R$^{1B}$ are fluorine; and
R$^2$ is methyl.

The following alternative embodiments of ring A, R$^A$ and m are contemplated in combination with any of the embodiments described hereinabove.

In one embodiment, in each of Formulas (I), (I'), (IA), and (IA'):
ring A is selected from the group consisting of phenyl, pyridazinyl, pyridinyl, pyrimidinyl, pyrazinyl, pyrazolyl, triazinyl, thiazolyl, and thienyl.

In one embodiment, in each of Formulas (I), (I'), (IA), and (IA'):
ring A is selected from the group consisting of phenyl, pyridinyl, and thienyl.

In one embodiment, in each of Formulas (I), (I'), (IA), and (IA'):
ring A is selected from the group consisting of phenyl and thienyl.

In one embodiment, in each of Formulas (I), (I'), (IA), and (IA'): chloro, bromo, —CN, —OCH$_3$, —CH$_2$OCH$_3$, methyl, ethyl, cyclopropyl, —CF$_3$, —CHF$_2$, —CH$_2$F, —OCF$_3$, and —OCHF$_2$.

In one embodiment, in each of Formulas (I), (I'), (IA), and (IA'):

each $R^A$ (when present) is independently selected from the group consisting of fluoro, chloro, methyl, and —CHF$_2$.

In one embodiment, in each of Formulas (I), (I'), (IA), and (IA'):

each $R^A$ (when present) is independently selected from the group consisting of fluoro and chloro.

In one embodiment, in each of Formulas (I), (I'), (IA), and (IA'):

ring A is selected from the group consisting of phenyl, pyridazinyl, pyridinyl, pyrimidinyl, pyrazinyl, pyrazolyl, triazinyl, thiazolyl, and thienyl;

m is 0, 1, 2, or 3, with the proviso that the value of m does not exceed the number of available substitutable hydrogen atoms on ring A; and each $R^A$ (when present) is independently selected from the group consisting of fluoro, chloro, bromo, —CN, —OCH$_3$, —CH$_2$OCH$_3$, methyl, ethyl, cyclopropyl, —CF$_3$, —CHF$_2$, —CH$_2$F, —OCF$_3$, and —OCHF$_2$.

In one such embodiment, m is 0. In another such embodiment, m is 1. In another such embodiment, m is 2. In another such embodiment, m is 3.

In one embodiment, in each of Formulas (I), (I'), (IA), and (IA'):

ring A is selected from the group consisting of phenyl, pyridinyl, and thienyl;

m is 0, 1, 2, or 3, with the proviso that the value of m does not exceed the number of available substitutable hydrogen atoms on ring A; and each $R^A$ (when present) is independently selected from the group consisting of fluoro, chloro, methyl, and —CHF$_2$.

In one such embodiment, m is 0. In another such embodiment, m is 1. In another such embodiment, m is 2. In another such embodiment, m is 3, with the proviso that the value of m does not exceed the number of available substitutable hydrogen atoms on ring A.

In one embodiment, in each of Formulas (I), (I'), (IA), and (IA'):

ring A is selected from the group consisting of phenyl and thienyl;

m is 0, 1, 2, or 3, with the proviso that the value of m does not exceed the number of available substitutable hydrogen atoms on ring A; and each $R^A$ (when present) is independently selected from the group consisting of fluoro and chloro. embodiment, m is 2. In another such embodiment, m is 3, with the proviso that the value of m does not exceed the number of available substitutable hydrogen atoms on ring A.

The following alternative embodiments of $R^L$ are contemplated in combination with any of the embodiments described hereinabove.

In one embodiment, in each of Formulas (I), (I'), (IA), and (IA'):

$R^L$ is lower alkyl,
wherein said lower alkyl is optionally further substituted with one or more fluorine, and
wherein 1 to 2 non-adjacent, non-terminal carbon atoms in said alkyl are optionally independently replaced with —O—, —NH—, —N(alkyl)-, —S—, —S(O)—, or —S(O)$_2$—.

In one embodiment, in each of Formulas (I), (I'), (IA), and (IA'):

$R^L$ is selected from the group consisting of methyl, ethyl, —CF$_3$, —CHF$_2$, —CH$_2$F, —CH$_2$CF$_3$, —CF$_2$CH$_3$, —CH$_2$OCH$_3$, —CH$_2$OCH$_2$CH$_3$, —CH$_2$CH$_2$OCH$_3$, —CH(OCH$_3$)CH$_3$, —CH$_2$SCH$_3$, —CH$_2$N(CH$_3$)$_2$, —CH$_2$OCF$_3$, and —CH$_2$OCHF$_2$.

In one embodiment, in each of Formulas (I), (I'), (IA), and (IA'):

$R^L$ is selected from the group consisting of methyl, —CHF$_2$, —CH$_2$OCH$_3$, CH$_2$OCF$_3$, and —CH$_2$OCHF$_2$.

In one embodiment, in each of Formulas (I), (I'), (IA), and (IA'):

$R^L$ is a moiety having the formula

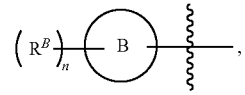

wherein:

ring B is selected from the group consisting of azetidinyl, benzimidazolyl, benzoisothiazolyl, benzoisoxazolyl, benzothiazolyl, benzoxazolyl, cyclobutyl, cyclohexyl, cyclopentyl, cyclopropyl, dihydroindenyl, dihydrooxazolyl, furanyl, imidazolyl, imidazopyridinyl, imidazopyrimidinyl, imidazothiazolyl, indenyl, indolyl, isothiazolyl, isoxazolyl, morpholinyl, oxadiazolyl, oxazolyl, oxetanyl, phenyl, piperazinyl, piperidinyl, pyrazinyl, pyrazolyl, pyrazolopyridinyl, pyrazolopyrimidinyl, pyridazinyl, pyridinyl, pyrimidinyl, pyrazolopyridinyl, pyrrolidinyl, pyrrolyl, pyrrolopyridinyl, pyrrolopyrimidinyl, tetrahydrofuranyl, tetrahydropyranyl, tetrazolyl, thiadiazolyl, thiazolyl, thienyl, thienylpyridine, thiomorpholinyl, thiomorpholinyl dioxide, and triazolyl.

In one embodiment, in each of Formulas (I), (I'), (IA), and (IA'):

$R^L$ is a moiety having the formula

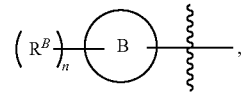

wherein: imidazopyridinyl, imidazopyrimidinyl, imidazothiazolyl, indolyl, isothiazolyl, isoxazolyl, oxadiazolyl, oxazolyl, oxetanyl, phenyl, pyrazinyl, pyrazolyl, pyridazinyl, pyridinyl, pyrimidinyl, pyrrolyl, tetrahydrofuranyl, tetrahydropyranyl, thiadiazolyl, thiazolyl, and thienyl.

In one embodiment, in each of Formulas (I), (I'), (IA), and (IA'):

$R^L$ is a moiety having the formula

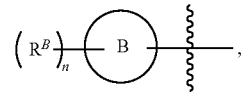

wherein:
ring B is selected from the group consisting of indolyl, phenyl, pyridinyl, and pyrimidinyl.

In one embodiment, in each of Formulas (I), (I'), (IA), and (IA'):

$R^L$ is a moiety having the formula

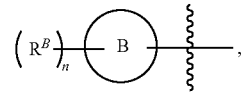

wherein:

each $R^B$ group (when present) is independently selected from the group consisting of halogen, oxo, —OH, —CN, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —CH$_2$OCH$_2$CH$_3$, —C≡CH, —C≡C—CH$_3$, —CF$_3$, —CHF$_2$, —CH$_2$F, —OCF$_3$, —OCH$_2$CF$_3$, —OCHF$_2$, —OCH$_2$F, —OCH$_2$CH$_2$F, phenyl, pyridinyl, oxadiazolyl, isoxazolyl, oxazolyl, and pyrrolyl, wherein each said phenyl, pyridinyl, oxadiazolyl, isoxazolyl, oxazolyl, and pyrrolyl is optionally substituted with from 1 to 3 substituents independently selected from the group consisting of fluoro, chloro, —CN, methyl, —OCH$_3$, and —CF$_3$.

In one embodiment, in each of Formulas (I), (I'), (IA), and (IA'):

$R^L$ is a moiety having the formula

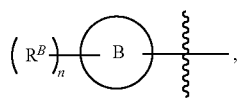

wherein:

each $R^B$ group (when present) is independently selected from the group consisting of fluoro, chloro, —CN, —OCH$_3$, —O—CH$_2$-cyclopropyl, —OCH$_2$—C≡C—H, —OCH$_2$—C≡C—CH$_3$, methyl, ethyl, cyclopropyl, —CH$_2$-cyclopropyl, —CH$_2$OCH$_3$, —C≡CH, —C≡C—CH$_3$, —CF$_3$, —CHF$_2$, —OCF$_3$, —OCHF$_2$, oxadiazolyl, isoxazolyl, and oxazolyl, wherein each said oxadiazolyl, isoxazolyl, and oxazolyl is optionally substituted with one substituent from the group consisting of fluoro and methyl.

In one embodiment, in each of Formulas (I), (I'), (IA), and (IA'):

$R^L$ is a moiety having the formula

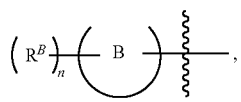

wherein:

each $R^B$ group (when present) is independently selected from the group consisting of fluoro, chloro, —CN, —C≡C—CH$_3$, —OMe, —CF$_3$, and oxadiazolyl.

In one embodiment, in each of Formulas (I), (I'), (IA), and (IA'):

$R^L$ is a moiety having the formula

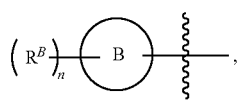

wherein:

ring B is selected from the group consisting of azetidinyl, benzimidazolyl, benzoisothiazolyl, benzoisoxazolyl, benzothiazolyl, benzoxazolyl, cyclobutyl, cyclohexyl, cyclopentyl, cyclopropyl, dihydroindenyl, dihydrooxazolyl, furanyl, imidazolyl, imidazopyridinyl, imidazopyrimidinyl, imidazothiazolyl, indenyl, indolyl, isothiazolyl, isoxazolyl, morpholinyl, oxadiazolyl, oxazolyl, oxetanyl, phenyl, piperazinyl, piperidinyl, pyrazinyl, pyrazolyl, pyrazolopyridinyl, pyrazolopyrimidinyl, pyridazinyl, pyridinyl, pyrimidinyl, pyrazolopyridinyl, pyrrolidinyl, pyrrolyl, pyrrolopyridinyl, pyrrolopyrimidinyl, tetrahydrofuranyl, tetrahydropyranyl, tetrazolyl, thiadiazolyl, thiazolyl, thienyl, thienylpyridine, thiomorpholinyl, thiomorpholinyl dioxide, and triazolyl;

each $R^B$ group (when present) is independently selected from the group consisting of halogen, oxo, —OH, —CN, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$ methyl, ethyl, propyl, cyclopropyl, —CH$_2$-cyclopropyl, —CH$_2$OCH$_3$, —CH$_2$OCH$_2$CH$_3$, —C≡CH, —C≡C—CH$_3$, —CF$_3$, —CHF$_2$, —CH$_2$F, —OCF$_3$, —OCH$_2$CF$_3$, —OCHF$_2$, —OCH$_2$F, —OCH$_2$CH$_2$F, phenyl, pyridinyl, oxadiazolyl, isoxazolyl, oxazolyl, and pyrrolyl, wherein each said phenyl, pyridinyl, oxadiazolyl, isoxazolyl, oxazolyl, and pyrrolyl is optionally substituted with from 1 to 3 substituents independently selected from the group consisting of fluoro, chloro, —CN, methyl, —OCH$_3$, and —CF$_3$; and n is 0, 1, 2, or 3.

In one such embodiment, n is 0. In another such embodiment, n is 1. In another such embodiment, n is 2. In another such embodiment, n is 3, with the proviso that the value of n does not exceed the number of available substitutable hydrogen atoms on ring B.

In one embodiment, in each of Formulas (I), (I'), (IA), and (IA'):

$R^L$ is a moiety having the formula

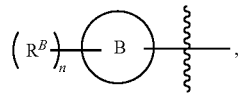

wherein: imidazopyridinyl, imidazopyrimidinyl, imidazothiazolyl, indolyl, isothiazolyl, isoxazolyl, oxadiazolyl, oxazolyl, oxetanyl, phenyl, pyrazinyl, pyrazolyl, pyridazinyl, pyridinyl, pyrimidinyl, pyrrolyl, tetrahydrofuranyl, tetrahydropyranyl, thiadiazolyl, thiazolyl, and thienyl;

each $R^B$ group (when present) is independently selected from the group consisting of fluoro, chloro, —CN, —OCH$_3$, —O—CH$_2$-cyclopropyl, —OCH$_2$—C≡C—H, —OCH$_2$—C≡C—CH$_3$, methyl, ethyl, cyclopropyl, —CH$_2$-cyclopropyl, —CH$_2$OCH$_3$, —C≡CH, —C≡C—CH$_3$, —CF$_3$, —CHF$_2$, —OCF$_3$, —OCHF$_2$, oxadiazolyl, isoxazolyl, and oxazolyl, wherein each said oxadiazolyl, isoxazolyl, and oxazolyl is optionally substituted with one substituent from the group consisting of fluoro and methyl; and n is 0, 1, 2, or 3, with the proviso that the value of n does not exceed the number of available substitutable hydrogen atoms on ring B.

In one such embodiment, n is 0. In another such embodiment, n is 1. In another such embodiment, n is 2. In another such embodiment, n is 3, with the proviso that the value of n does not exceed the number of available substitutable hydrogen atoms on ring B.

In one embodiment, in each of Formulas (I), (I'), (IA), and (IA'):

$R^L$ is a moiety having the formula

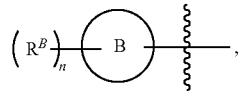

wherein:

ring B is selected from the group consisting of indolyl, phenyl, pyridinyl, and pyrimidinyl;

each $R^B$ group (when present) is independently selected from the group consisting of fluoro, chloro, —CN, —C≡C—CH$_3$, —OMe, —CF$_3$, and oxadiazolyl; and n is 0, 1, 2, or 3.

In one such embodiment, n is 0. In another such embodiment, n is 1. In another such embodiment, n is 2. In another such embodiment, n is 3, with the proviso that the value of n does not exceed the number of available substitutable hydrogen atoms on ring B.

The following alternative embodiments of ring C, $R^C$, and p are contemplated in combination with any of the embodiments described hereinabove.

In one embodiment, in each of Formulas (I), (I'), (IA), and (IA'):

ring C is selected from the group consisting of pyrazine and pyrimidine.

In one embodiment, in each of Formulas (I), (I'), (IA), and (IA'):

p is 0 or 1.

ring C is selected from the group consisting of pyrazine and pyrimidine; and p is 0 or 1.

In one embodiment, in each of Formulas (I), (I'), (IA), and (IA'):

$R^C$ (when present) is independently selected from the group consisting of methyl, ethyl, —CF$_3$, —CHF$_2$, —CH$_2$F, —CH$_2$OCH$_3$, and cyclopropyl.

In one embodiment, in each of Formulas (I), (I'), (IA), and (IA'):

$R^C$ (when present) is independently selected from the group consisting of methyl, —CF$_3$, and cyclopropyl.

In one embodiment, in each of Formulas (I), (I'), (IA), and (IA'):

ring C is selected from the group consisting of pyrazine and pyrimidine;

p is 0 or 1; and $R^C$ (when present) is independently selected from the group consisting of methyl, ethyl, —CF$_3$, —CHF$_2$, —CH$_2$F, —CH$_2$OCH$_3$, and cyclopropyl.

In one embodiment, in each of Formulas (I), (I'), (IA), and (IA'):

ring C is selected from the group consisting of pyrazine and pyrimidine;

p is 0 or 1; and $R^C$ (when present) is independently selected from the group consisting of methyl, —CF$_3$, and cyclopropyl.

In one embodiment, in each of Formulas (I), (I'), (IA), and (IA'):

ring C, $R^C$, and p form a moiety selected from the group consisting of:

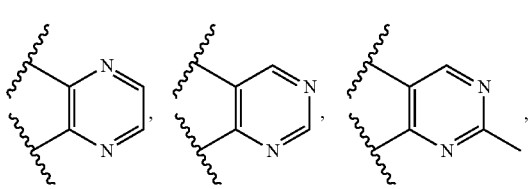

-continued

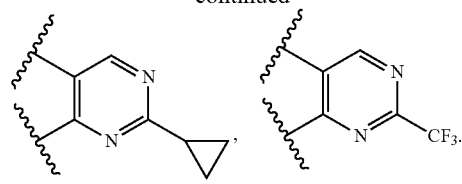

The following alternatives of -L$_1$- are contemplated in combination with any of the embodiments described hereinabove.

In one embodiment, in each of Formulas (I), (I'), (IA), and (IA'):

-L$_1$- is a bond.

-L$_1$- is the divalent moiety —C(O)NH—. In these embodiments, the moiety:

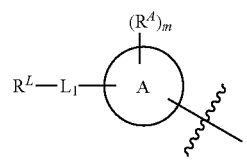

has the form:

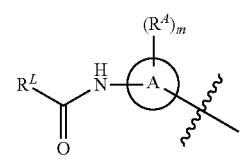

Specific non-limiting examples of compounds of the invention are shown in the table of examples below. While only one tautomeric form of each compound is shown in the tables, it shall be understood that all tautomeric forms of the compounds are contemplated as being within the scope of the non-limiting examples.

In another embodiment, in each of Formulas (I), (I'), (IA), and (IA'), 1 to 3 carbon atoms of the compounds of the invention may be replaced with 1 to 3 silicon atoms so long as all valency requirements are satisfied.

Another embodiment provides a composition comprising a compound of the invention and a pharmaceutically acceptable carrier or diluent.

Another embodiment provides a composition comprising a compound of the invention, either as the sole active agent, or optionally in combination with one or more additional therapeutic agents, and a pharmaceutically acceptable carrier or diluent. Non-limiting examples of additional therapeutic agents which may be useful in combination with the compounds of the invention include those selected from the group consisting of: (a) drugs that may be useful for the treatment of Alzheimer's disease and/or drugs that may be useful for treating one or more symptoms of Alzheimer's disease, (b) drugs that may be useful for inhibiting the synthesis Aβ, (c) drugs that may be useful for treating neurodegenerative diseases, and (d) drugs that may be useful for the treatment of type II diabetes and/or one or more symptoms or associated pathologies thereof.

Non-limiting examples of additional therapeutic agents which may be useful in combination with the compounds of the invention include drugs that may be useful for the treatment, prevention, delay of onset, amelioration of any pathology associated with Aβ and/or a symptom thereof. Non-limiting examples of pathologies associated with Aβ include: associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $\beta_2$ microglobulins and complications arising therefrom in hemodialysis patients), scrapie, bovine spongiform encephalitis, and Creutzfeld-Jakob disease, comprising administering to said patient at least one compound of the invention, or a tautomer or isomer thereof, or pharmaceutically acceptable salt or solvate of said compound or said tautomer, in an amount effective to inhibit or treat said pathology or pathologies.

Non-limiting examples of additional therapeutic agents for that may be useful in combination with compounds of the invention include: muscarinic antagonists (e.g., $m_1$ agonists (such as acetylcholine, oxotremorine, carbachol, or McNa343), or $m_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®), (±)-2,3-dihydro-5,6-dimethoxy-2-[[1-(phenylmethyl)-4-piperidinyl]methyl]-1H-inden-1-one hydrochloride), galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies (such as bapineuzemab, Wyeth/Elan); vitamin E; nicotinic acetylcholine receptor agonists; CB1 receptor inverse agonists or CB1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors (e.g., GSK3beta inhibitors, cdk5 inhibitors, or ERK inhibitors); Tau aggregation inhibitors (e.g., Rember®); RAGE inhibitors (e.g., TTP 488 (PF-4494700)); anti-Abeta vaccine; APP ligands; agents that upregulate insulin, as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g., PBT2); and GPR3 modulators; and antihistamines such as Dimebolin (e.g., Dimebon®, Pfizer).

Another embodiment provides a method of preparing a pharmaceutical composition comprising the step of admixing at least one compound of the invention or pharmaceutically acceptable salt thereof, and a pharmaceutically acceptable carrier or diluent.

Another embodiment provides a method of inhibiting β-secretase comprising exposing a population of cells expressing β-secretase to at least one compound of the invention, or a tautomer thereof, in an amount effective to inhibit β-secretase. In one such embodiment, said population of cells is in vivo. In another such embodiment, said population of cells is ex vivo. In another such embodiment, said population of cells is in vitro.

Additional embodiments in which the compounds of the invention may be useful include: a method of inhibiting β-secretase in a patient in need thereof. A method of inhibiting the formation of Aβ from APP in a patient in need thereof. A method of inhibiting the formation of Aβ plaque and/or Aβ fibrils and/or Aβ oligomers and/or senile plaques and/or neurofibrillary tangles and/or inhibiting the deposition of amyloid protein (e.g., amyloid beta protein) in, on or around neurological tissue (e.g., the brain), in a patient in need thereof. Each such embodiment comprises administering at least one compound of the invention, or a tautomer thereof, or pharmaceutically acceptable salt of said compound or said tautomer, in a therapeutically effective amount to inhibit said pathology or condition in said patient.

Additional embodiments in which the compounds of the invention may be useful include: a method of treating, preventing, and/or delaying the onset of one or more pathologies Aβ. Non-limiting examples of pathologies which may be associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $\beta_2$ microglobulins and complications arising therefrom in hemodialysis patients), scrapie, bovine spongiform encephalitis, and Creutzfeld-Jakob disease, said method(s) comprising administering to said patient in need thereof at least one compound of the invention, or a tautomer thereof, or pharmaceutically acceptable salt of said compound or said tautomer, in an amount effective to inhibit said pathology or pathologies.

Another embodiment in which the compounds of the invention may be useful includes a method of treating Alzheimer's disease, wherein said method comprises administering an effective (i.e., therapeutically effective) amount of one or more compounds of the invention (or a tautomer thereof, or pharmaceutically acceptable salt of said compound or said tautomer), optionally in further combination with one or more additional therapeutic agents which may be effective to treat Alzheimer's disease or a disease or condition associated therewith, to a patient in need of treatment. In embodiments wherein one or more additional therapeutic agents are administered, such agents may be administered sequentially or together. Non-limiting examples of associated diseases or conditions, and non-limiting examples of suitable additional therapeutically active agents, are as described above.

Another embodiment in which the compounds of the invention may be useful includes a method of treating mild cognitive impairment ("MCI"), wherein said method comprises administering an effective (i.e., therapeutically effective) amount of one or more compounds of the invention (or a tautomer thereof, or pharmaceutically acceptable salt of said compound or said tautomer) to a patient in need of treatment. In one such embodiment, treatment is commenced prior to the onset of symptoms. a method of preventing, or alternatively of delaying the onset, of mild cognitive impairment or, in a related embodiment, of preventing or alternatively of delaying the onset of Alzheimer's disease. In such embodiments, treatment can be initiated prior to the onset of symptoms, in some embodiments significantly before (e.g., from several months to several years before) the onset of symptoms to a patient at risk for developing MCI or Alzheimer's disease. Thus, such methods comprise administering, prior to the onset of symptoms or clinical or biological evidence of MCI or Alzheimer's disease (e.g., from several months to several years before, an effective (i.e., therapeutically effective), and over a period of time and at a frequency of dose sufficient for the therapeutically effective degree of inhibition of the BACE enzyme over the period of treatment, an amount of one or more compounds of the invention (or a tautomer thereof, or pharmaceutically acceptable salt of said compound or said tautomer) to a patient in need of treatment.

Another embodiment in which the compounds of the invention may be useful includes a method of treating Down's syndrome, comprising administering an effective (i.e., therapeutically effective) amount of one or more compounds of the invention (or a tautomer thereof, or pharmaceutically acceptable salt or solvate of said compound or said tautomer) to a patient in need of treatment.

Another embodiment in which the compounds of the invention may be useful includes a kit comprising, in separate containers, in a single package, pharmaceutical compositions for use in combination, wherein one container comprises an effective amount of a compound of the invention (or a tautomer thereof, or pharmaceutically acceptable salt of said compound or said tautomer) in a pharmaceutically acceptable carrier, and another container (i.e., a second container) comprises an effective amount of another pharmaceutically active ingredient, the combined quantities of the compound of the invention and the other pharmaceutically active ingredient being effective to: (a) treat Alzheimer's disease, or (b) inhibit the deposition of amyloid protein in, on or around neurological tissue (e.g., the brain), or (c) treat neurodegenerative diseases, or (d) inhibit the activity of BACE-1 and/or BACE-2.

In various embodiments, the compositions and methods disclosed above and below wherein the compound(s) of the invention is a compound or compounds selected from the group consisting of the exemplary compounds of the invention described herein.

In another embodiment, the invention provides methods of treating a disease or pathology, wherein said disease or pathology is Alzheimer's disease, olfactory impairment associated with Alzheimer's disease, Down's syndrome, olfactory impairment associated with disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease. Such methods comprise administering a compound of the invention, or a pharmaceutically acceptable salt thereof, to a patient in need thereof in an amount effective to treat said disease or pathology.

In another embodiment, the invention provides for the use of any of the compounds of the invention for use as a medicament, or in medicine, or in therapy.

In another embodiment, the invention provides for use of a compound of the invention for the manufacture of a medicament for the treatment of a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease.

Definitions

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy" etc.

It shall be understood that, in the various embodiments of the invention described herein, any variable not explicitly defined in the context of the embodiment is as defined in Formula (I). All valences not explicitly filled are assumed to be filled by hydrogen. those research animals and companion animals such as mice, primates, monkeys, great apes, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, or they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

"Halogen" (or "halo") means fluorine, chlorine, bromine, or iodine. Preferred are fluorine, chlorine and bromine.

"Alkyl" means an aliphatic hydrocarbon group, which may be straight or branched, comprising 1 to about 10 carbon atoms. "Lower alkyl" means a straight or branched alkyl group comprising 1 to about 4 carbon atoms. Branched means that one or more lower alkyl groups such as methyl, ethyl or propyl, are attached to a linear alkyl chain. Non-limiting examples of suitable alkyl groups include methyl, ethyl, n-propyl, isopropyl, n-butyl, i-butyl, and t-butyl.

"Alkenyl" means an aliphatic hydrocarbon group containing at least one carbon-carbon double bond and which may be straight or branched and comprising about 2 to about 10 carbon atoms in the straight or branched chain. Branched means that one or more lower alkyl groups such as methyl, ethyl propyl, ethenyl or propenyl are attached to a linear or branched alkenyl chain. "Lower alkenyl" means about 2 to about 4 carbon atoms in the chain which may be straight or branched. Non-limiting examples of suitable alkenyl groups include ethenyl, propenyl, n-butenyl, 3-methylbut-2-enyl, n-pentenyl, octenyl and decenyl. triple bond and which may be straight or branched and comprising about 2 to about 10 carbon atoms in the chain. Branched means that one or more lower alkyl groups such as methyl, ethyl or propyl, or lower alkenyl or lower alkynyl groups, are attached to a linear alkynyl chain. "Lower alkynyl" means about 2 to about 4 carbon atoms in the chain which may be straight or branched. Non-limiting examples of suitable alkynyl groups include ethynyl, propynyl, 2-butynyl and 3-methylbutynyl.

"Aryl" means an aromatic monocyclic or multicyclic ring system comprising about 6 to about 14 carbon atoms, preferably 6 to 10 carbon atoms. The aryl group can be optionally substituted with one or more "ring system substituents" which may be the same or different, and are as defined herein. Non-limiting examples of suitable aryl groups include phenyl and naphthyl. "Monocyclic aryl" means phenyl.

"Heteroaryl" means an aromatic monocyclic or multicyclic ring system comprising about 5 to about 14 ring atoms, preferably 5 to 10 ring atoms, in which one or more of the ring atoms is an element other than carbon, for example nitrogen, oxygen or sulfur, alone or in combination. Preferred heteroaryls contain 5 to 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from the group consisting of N, O, and S, and oxides thereof. The point of attachment to the parent monocyclic heteroaryl moities include pyridyl, pyrazinyl, furanyl, thienyl, pyrimidinyl, pyridazinyl, pyridoneyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic monocyclic or multicyclic ring system comprising 3 to 10 carbon atoms, preferably 3 to 6 carbon atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of multicyclic cycloalkyls include [1.1.1]-bicyclopentane, 1-decalinyl, norbornyl, adamantyl and the like.

"Heterocycloalkyl" (or "heterocyclyl") means a non-aromatic saturated monocyclic or multicyclic ring system comprising 3 to 10 ring atoms, preferably 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

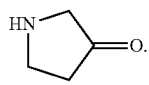

As used herein, the term "monocyclic heterocycloalkyl" refers monocyclic versions of the heterocycloalkyl moities described herein and include a 4- to 7-membered monocyclic heterocycloalkyl groups comprising from 1 to 4 ring heteroatoms, said ring heteroatoms being independently selected attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

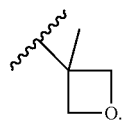

It should be noted that in hetero-atom containing ring systems of this invention, there are no hydroxyl groups on carbon atoms adjacent to a N, O or S, as well as there are no N or S groups on carbon adjacent to another heteroatom.

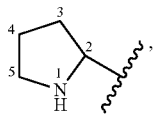

there is no —OH attached directly to carbons marked 2 and 5.

"Alkoxy" means an —O-alkyl group in which the alkyl group is as previously described. Non-limiting examples of alkoxy groups include methoxy, ethoxy, n-propoxy, iso-propoxy and n-butoxy. The bond to the parent moiety is through the oxygen.

Any of the foregoing functional groups may be unsubstituted or substituted as described herein. The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl-moiety or the like includes substitution on any ring portion and/or on the alkyl portion of the group.

When a variable appears more than once in a group, e.g., $R^6$ in —$N(R^6)_2$, or a variable appears more than once in a structure presented herein, the variables can be the same or different. isomers, e.g., containing (R)- and (S)-stereochemistry. For example:

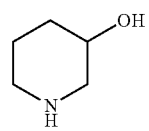

means containing both

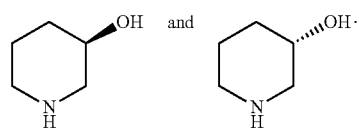

The wavy line ~~~, as used herein, indicates a point of attachment to the rest of the compound. Lines drawn into the ring systems, such as, for example:

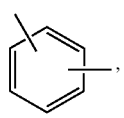

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

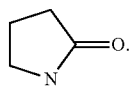

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

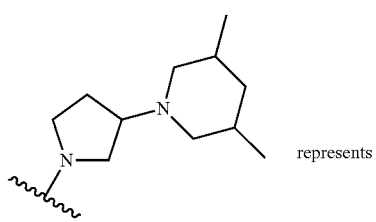

represents

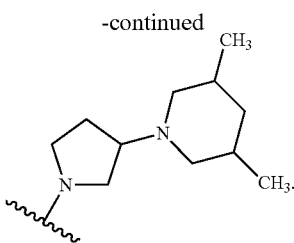

In another embodiment, the compounds of the invention, and/or compositions comprising them, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer thereof, or pharmaceutically acceptable salt of said compound or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan. group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Those skilled in the art will recognize those instances in which the compounds of the invention may be converted to prodrugs and/or solvates, another embodiment of the present invention. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms where they exist. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

Those skilled in the art will recognize those instances in which the compounds of the invention may form salts. In such instances, another embodiment provides pharmaceutically invention herein is understood to include reference to salts thereof, unless otherwise indicated. The term "salt(s)", as employed herein, denotes any of the following: acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also potentially useful. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplary acid addition salts which may be useful include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others. within the scope of the invention and all acid and base salts are considered as potentially useful alternatives to the free forms of the corresponding compounds for purposes of the invention.

Another embodiment which may be useful includes pharmaceutically acceptable esters of the compounds of the invention. Such esters may include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

As mentioned herein, under certain conditions the compounds of the invention may form tautomers. Such tautomers, when present, comprise another embodiment of the invention. It shall be understood that all tautomeric forms of such compounds are within the scope of the compounds of the invention. For example, all keto-enol and imine-enamine forms of the compounds, when present, are included in the invention. Thus, compounds of the invention conforming to the formula:

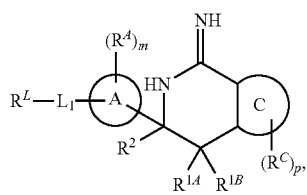

and its tautomer, which can be depicted as:

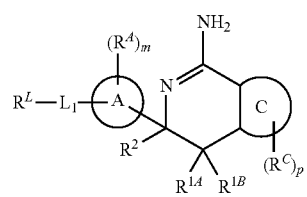

are both contemplated as being within the scope of the compounds of the invention. As noted above, while only one said tautomeric form of each example compound of the invention may be the compounds are contemplated as being within the scope of the non-limiting example compounds of the invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Where various stereoisomers of the compounds of the invention are possible, another embodiment provides for diastereomeric mixtures and individual enantiomers of the compounds of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Another embodiment which may be useful include isotopically-labelled compounds of the invention. Such compounds are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, and $^{36}$Cl, respectively.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Polymorphic forms of the compounds of the invention, and of the salts, solvates, esters and prodrugs of the compounds of the invention, are intended to be included in the present invention.

Another embodiment provides suitable dosages and dosage forms of the compounds of the invention. Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/day of the mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, preferably from about 1 mg to about 50 mg, more preferably from about 1 mg to about 25 mg, according to the particular application. In another embodiment, a typical recommended daily dosage regimen for oral administration can range from about 1 mg/day to about 500 mg/day, preferably 1 mg/day to 200 mg/day, in two to four divided doses.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, another embodiment provides combinations comprising an amount of at least one compound of the invention, or a pharmaceutically acceptable salt, solvate, ester or prodrug thereof, and an effective amount of one or more additional agents described above.

Another embodiment provides for pharmaceutically acceptable compositions comprising a compound of the invention, either as the neat chemical or optionally further comprising additional ingredients. For preparing pharmaceutical compositions from the compounds of the invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. Non-limiting examples which may be useful include water or water-propylene glycol solutions for parenteral emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

Another embodiment which may be useful includes compositions comprising a compound of the invention formulated for transdermal delivery. The transdermal compositions can take the form of creams, lotions, aerosols and/or emulsions and can be included in a transdermal patch of the matrix or reservoir type as are conventional in the art for this purpose.

Other embodiment which may be useful includes compositions comprising a compound of the invention formulated for subcutaneous delivery or for oral delivery. In some embodiments, it may be advantageous for the pharmaceutical preparation comparing one or more compounds of the invention be prepared in a unit dosage form. In such forms, the preparation may be subdivided into suitably sized unit doses containing appropriate quantities of the active component, e.g., an effective amount to achieve the desired purpose. Each of the foregoing alternatives, together with their corresponding methods of use, are considered as included in the various embodiments of the invention.

PREPARATIVE EXAMPLES

Compounds of the invention can be made using procedures known in the art. The following reaction schemes show typical procedures, but those skilled in the art will recognize that other procedures can also be suitable. Reactions may involve monitoring for consumption of starting material, and there are many methods for said monitoring, including but not limited to thin layer chromatography (TLC) and liquid chromatography mass spectrometry (LCMS), and those skilled in the art will recognize that where one method is specified, other non-limiting methods may be substituted.

Techniques, solvents and reagents may be referred to by their abbreviations as follows:
Acetonitrile: MeCN, ACN Methanol: MeOH
Aqueous: aq. Microliters: μl or μL
1-[Bis(dimethylamino)methylene]-1H-1,2,3 Milligrams: mg
-triazolo[4,5-b]pyridinium 3-oxide Milliliters: mL
hexafluorophosphate: HATU Millimoles: mmol
[1,1'-Bis(diphenylphosphino)ferrocene] Micromoles: uM or μM
-dichloropalladium(II): Pd(dppf)Cl$_2$ Minutes: min
Carboxybenzyl: Cbz Molar: M
Concentrated: conc. n-Butyllithium: nBuLi or n-BuLi
Di-tert-butyldicarbonate: Boc$_2$O Normal: N
Dichloromethane: DCM Nuclear magnetic resonance spectroscopy:
Diisopropylethylamine: DIEA or iPr$_2$NEt NMR
Dimethylacetamide: DMA Palladium on carbon: Pd/C
Dimethylformamide: DMF Petroleum ether: PE
Dimethylsulfoxide: DMSO Pound per square inch: psi
Ethanol: EtOH Preparative: prep-, p-
Ethyl: Et Room temperature (ambient, about 25° C.): rt or
Ethyl acetate: AcOEt, EtOAc, or EA RT Example: Ex. Saturated: sat.

Grams: g Silica gel: $SiO_2$

Hexanes: hex Sodium ethoxide: NaOEt

High performance liquid chromatography: Supercritical Fluid Chromatography: SFC

HPLC tert-Butoxycarbonyl: t-Boc or Boc

Hours: h Temperature: temp.

Liquid chromatography mass Spectrometry: Tetrahydrofuran: THF

LCMS Thin layer chromatography: TLC

Liter: L Titanium(IV)ethoxide: $Ti(OEt)_4$

Lithium bis(trimethylsilyl)amide: LHMDS Triethylamine: $Et_3N$ or TEA

Lithium diisopropylamide: LDA Trifluoroacetic acid: TFA

Method A

Synthesis of (S)-tert-butyl (7-(5-bromo-2-fluorophenyl)-7-methyl-7,8-dihydropyrido[4,3-d]pyrimidin-5(6H)-ylidene)carbamate (A12)

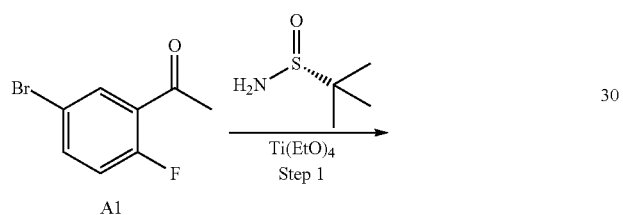

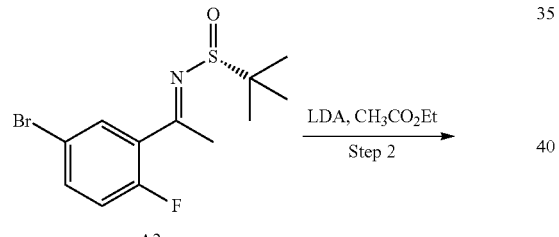

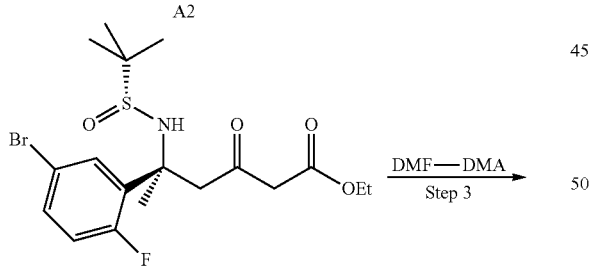

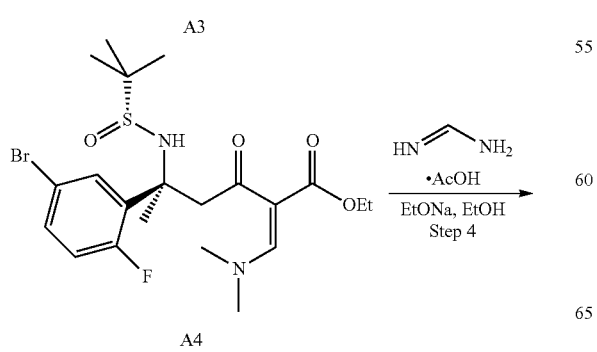

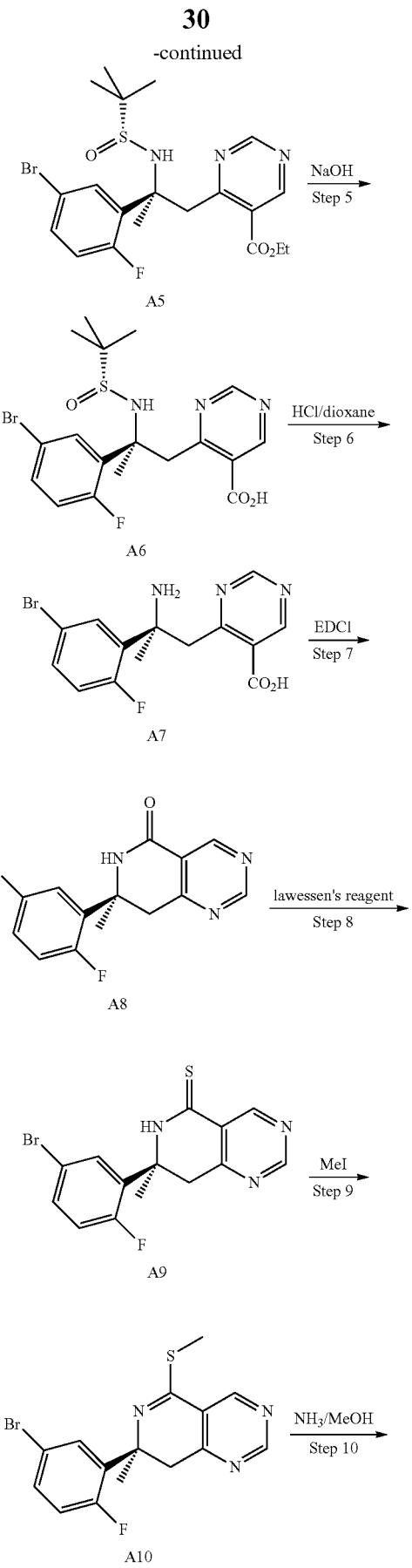

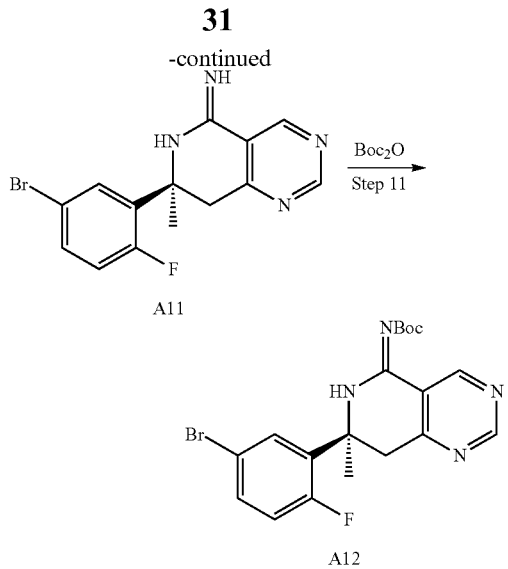

Step 1: (R,E)-N-(1-(5-bromo-2-fluorophenyl)ethylidene)-2-methylpropane-2-sulfinamide A solution of 1-(5-bromo-2-fluorophenyl)ethanone (60 g, 280 mmol), R-(+)-2-Methylpropane-2-sulfinic acid amide (35 g, 290 mmol) and Ti(OEt)$_4$ (128 g, 560 mol) in THF (600 mL) was stirred at 70° C. for 8 h, quenched by water (200 mL), filtered and extracted. The combined extracts were concentrated and purified by silica column to afford the title compound. LCMS m/z=320 (M+1).

Step 2: (S)-ethyl 5-(5-bromo-2-fluorophenyl)-5-((R)-1,1-dimethylethylsulfinamido)-3-oxohexanoate A solution of LDA (200 mL, 197 mmol, 2 N in THF) was added EtOAc (14.5 g, 164 mmol) and stirred at −78° C. for 2 h. A solution of (R,E)-N-(1-(5-bromo-2-fluoro-phenyl)ethylidene)-2-methylpropane-2-sulfinamide (10.5 g, 33 mmol) in THF (200 mL) was added and stirred at −78° C. for 2 h, quenched by NH$_4$Cl (aq, 200 mL), extracted with EtOAc and concentrated. The residue was purified by silica column to afford the title compound. $^1$H NMR (400 MHz, CDCl$_3$): δ 7.67-7.64 (m, 1 H), 7.37-7.35 (m, 1 H), 6.93-6.90 (m, 1 H), 4.19-4.13 (m, 3 H), 3.43-3.41 (m, 2 H), 2.09 (s, 2 H), 1.76 (s, 2 H), 1.31-1.627 (m, 12 H).

Step 3: (S,E)-ethyl 5-(5-bromo-2-fluorophenyl)-2-((dimethylamino)methylene)-5-((R)-1,1-dimethylethylsulfinamido)-3-oxohexanoate A solution of (S)-ethyl 5-(5-bromo-2-fluorophenyl)-5-((R)-1,1-dimethylethyl-sulfinamido)-3-oxohexanoate (28 g, 62.3 mmol) in DMF-DMA (70 mL) was stirred at 10° C. for 3 h. The mixture was concentrated at 30° C. under reduced pressure to afford the title compound. It was used in next step without further purification. LCMS m/z=505 (M+1).

Step 4: ethyl 4-((S)-2-(5-bromo-2-fluorophenyl)-2-((R)-1,1-dimethylethyl sulfinamido)propyl)pyrimidine-5-carboxylate To a solution of sodium ethoxide (9.9 mmol, prepared from 0.23 g of sodium metal in 28 mL of ethanol) was added (S,E)-ethyl 5-(5-bromo-2-fluorophenyl)-2-((dimethylamino)methylene)-5-((R)-1,1-dimethylethylsulfinamido)-3-oxohexanoate (5 g, 9.9 mmol, see scheme 2.3) and formamidine acetate (1.6 g, 9.9 mmol). The mixture was refluxed for 18 h, and concentrated. The residue was dissolved in DCM and washed with water. The organic layer was dried over Na$_2$SO$_4$, concentrated to afford the title compound. LCMS m/z=486 (M+1). $^1$H NMR (400 MHz, CDCl$_3$): δ 9.22 (s, 1 H), 8.74 (s, 1 H), 7.34-6.91 (m, 3 H), 3.80-3.70 (m, 2 H), 3.27-3.06 (m, 2 H), 2.78-2.15 (m, 3 H), 1.49 (s, 3 H), 1.23-0.90 (m, 9 H).

Step 5: 4-((S)-2-(5-bromo-2-fluorophenyl)-2-((R)-1,1-dimethylethylsulfinamido) propyl)pyrimidine-5-carboxylic acid To a solution of ethyl 4-((S)-2-(5-bromo-2-fluorophenyl)-2-((R)-1,1-dimethylethyl-sulfinamido)propyl)pyrimidine-5-carboxylate (4 g, 8.2 mmol) in MeOH (50 mL) cooled to 0° C. was added aqueous NaOH (15 mL, 2 M in water). The resulting mixture was stirred at RT for 0.5 h, and acidified with HCl (aq., 1 M) to pH 5. The solution was extracted with DCM. The combined extracts were dried over Na$_2$SO$_4$, concentrated to afford the title compound. LCMS m/z=458 (M+1).

Step 6: (S)-4-(2-amino-2-(5-bromo-2-fluorophenyl) propyl)pyrimidine-5-carboxylic acid To a solution of 4-((S)-2-(5-bromo-2-fluorophenyl)-2-((R)-1,1-dimethylethylsulfinamido)propyl)pyrimidine-5-carboxylic acid (3.1 g, 6.8 mmol) in DCM (50 mL) cooled to 0° C. was added HCl/dioxane (8 mL, 4 M). The resulting mixture was stirred at RT for 5 mins, and concentrated to afford the title compound. LCMS m/z=354 (M+1).

Step 7: (S)-7-(5-bromo-2-fluorophenyl)-7-methyl-7,8-dihydropyrido[4,3-d]pyrimidin-5(6H)-one A mixture of (S)-4-(2-amino-2-(5-bromo-2-fluorophenyl) propyl)pyrimidine-5-carboxylic acid (2.3 g, 6.5 mmol), HATU (4.9 g, 13 mmol) and DIEA (1.7 g, 13 mmol) in DMF (40 mL) was stirred at RT overnight, and quenched with water, extracted with EtOAc. The combined extracts were dried over Na$_2$SO$_4$, concentrated, purified by silica column chromatography (PE:EtOAc=1:10) to afford the title compound. LCMS m/z=336 (M+1).

Step 8: (S)-7-(5-bromo-2-fluorophenyl)-7-methyl-7,8-dihydropyrido[4,3-d]pyrimidine-5(6H)-thione A mixture of (S)-7-(5-bromo-2-fluorophenyl)-7-methyl-7,8-dihydropyrido[4,3-d]pyrimidin-5(6H)-one (1 g, 3.0 mmol) in toluene (40 mL) was added Lawesson's reagent (1.8 g, 4.5 mmol) and heated at 80° C. for 2 h. After cooling, the mixture was diluted with EtOAc. The organic layer was washed with water, dried over Na$_2$SO$_4$, concentrated and purified by silica column (PE:EtOAc=1:10) to afford the title compound. LCMS m/z=352 (M+1).

Step 9: (S)-7-(5-bromo-2-fluorophenyl)-7-methyl-5-(methylthio)-7,8-dihydropyrido[4,3-d]pyrimidine The mixture of (S)-7-(5-bromo-2-fluorophenyl)-7-methyl-7,8-dihydropyrido[4,3-d]pyrimidine-5(6H)-thione (2.8 g, 7.9 mmol), K$_2$CO$_3$ (1.9 g, 15.8 mmol) and CH$_3$I (3.4 g, 24 mmol) in THF (80 mL) was heated at 50° C. for 2 h, and quenched with water, extracted with EtOAc. The combined extracts were dried over Na$_2$SO$_4$, concentrated and purified by silica column (PE:EtOAc=1:1) to afford the title compound. LCMS m/z=366 (M+1). ¹H NMR (400 MHz, MeOH): δ 9.22 (s, 1 H), 8.74 (s, 1 H), 7.34-6.91 (m, 3 H), 3.80-3.70 (m, 2 H), 2.78-2.15 (m, 3 H), 1.23-0.90 (m, 3 H).

Step 10: (S)-7-(5-bromo-2-fluorophenyl)-7-methyl-7,8-dihydropyrido[4,3-d]pyrimidin-5(6H)-imine To a solution of (S)-7-(5-bromo-2-fluorophenyl)-7-methyl-5-(methylthio)-7,8-dihydropyrido[4,3-d]pyrimidine (300 mg, 0.82 mmol) in MeOH (10 mL) was added NH₃/MeOH (10 mL, saturated with NH₃ at −78° C.). The solution was stirred at 100° C. overnight, and concentrated to afford the title compound. LCMS m/z=335 (M+1). ¹H NMR (400 MHz, MeOH): δ 9.27 (s, 2 H), 7.43-7.46 (m, 1 H), 7.32-7.34 (m, 1 H), 7.05-7.10 (m, 1 H), 3.89 (d, J=17.2 Hz, 1 H), 3.64 (d, J=17.2 Hz, 1 H), 1.91 (m, 3 H).

Step 11: (S)-tert-butyl (7-(5-bromo-2-fluorophenyl)-7-methyl-7,8-dihydropyrido[4,3-d]pyrimidin-5(6H)-ylidene)carbamate A mixture of (S)-7-(5-bromo-2-fluorophenyl)-7-methyl-7,8-dihydropyrido[4,3-d]pyrimidin-5(6H)-imine (260 mg, 0.78 mmol), DIEA (300 mg, 2.33 mmol) and (Boc)₂O (503 mg, 2.33 mmol) in MeOH (20 mL) was stirred at 25° C. for 5 h. The mixture was concentrated and purified by column chromatography (PE:EtOAc=10:1) to afford the title compound. LCMS m/z=435 (M+1).

Method B

Synthesis of (S)-7-(5-bromo-3-chlorothiophen-2-yl)-7-methyl-7,8-dihydropyrido[4,3-d]pyrimidin-5(6H)-imine (B12)

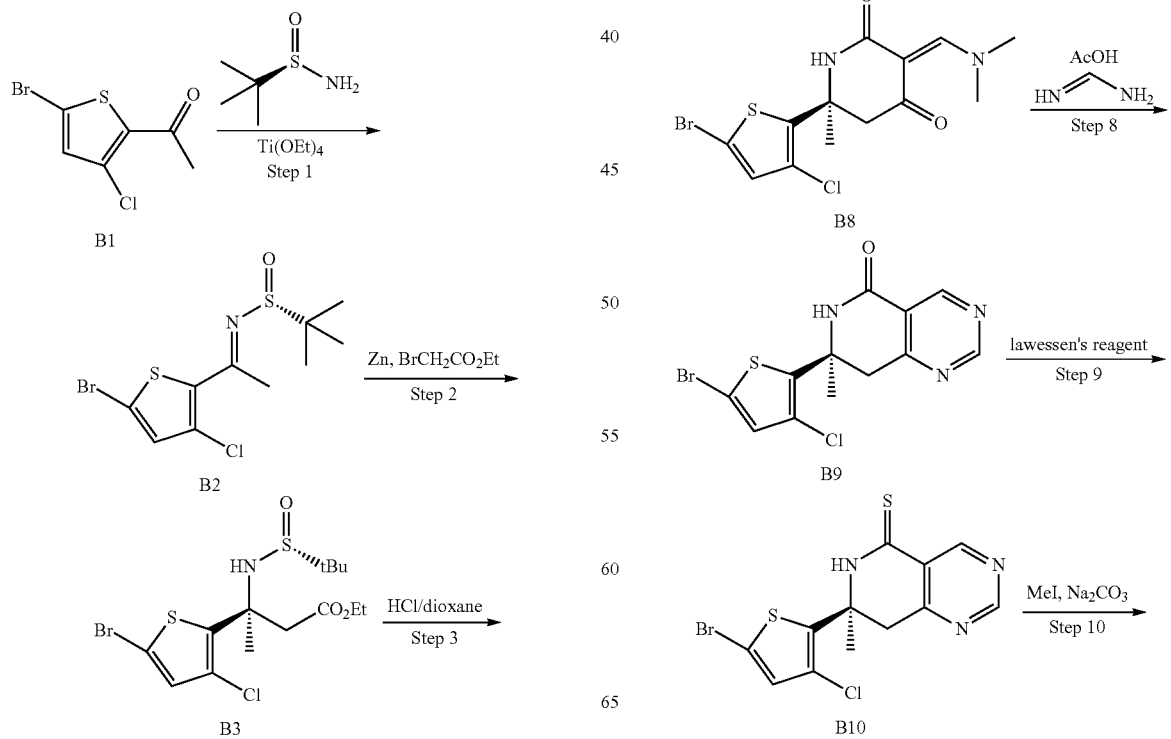

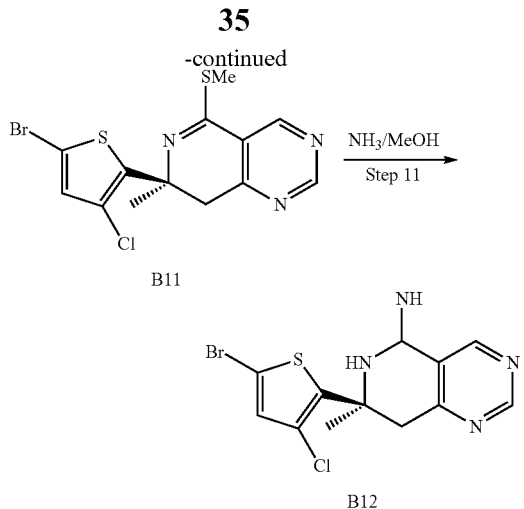

Step 1: (R,E)-N-(1-(5-bromo-3-chlorothiophen-2-yl)ethylidene)-2-methylpropane-2-sulfinamide A mixture of 1-(5-bromo-3-chlorothiophen-2-yl)ethanone (5.3 g, 22 mmol), (R)-(+)-2-methyl-2-propanesulfinamide (2.7 g, 22 mmol) and Ti(OEt)$_4$ (10 g, 44 mmol) in THF (50 mL) was heated to reflux overnight, and quenched by water (150 mL). The mixture was filtered. The filtrate was extracted with EtOAc. The combined extracts were dried over Na$_2$SO$_4$, filtered, concentrated and purified by silica column (PE:EtOAc=20:1) to afford the title compound. LCMS m/z=342/344 (M+1). $^1$H NMR (400 MHz, CDCl$_3$): δ 7.00 (m, 1 H), 2.88 (s, 3 H), 1.33 (s, 9 H).

Step 2: (S)-ethyl 3-(5-bromo-3-chlorothiophen-2-yl)-3-((R)-1,1-dimethylethylsulfin amido)butanoate A mixture of Zn (2 g, 30 mmol) and CuCl (0.3 g, 3 mmol) in 20 mL of THF was heated to reflux for 0.5 h and cooled. Ethyl bromoacetate (1.26 g, 7.5 mmol) in 5 mL of THF was added dropwise to above mixture and stirred at RT for 0.5 h, then heated to 50° C. for 0.5 h. The resulting mixture was cooled to 0° C., and added a solution of (R,E)-N-(1-(5-bromo-3-chlorothiophen-2-yl)ethylidene)-2-methylpropane-2-sulfinamide (1.03 g, 3 mmol) in 5 mL of THF. After stirring at 0° C. for 1 h, the mixture was filtered. The filtrate was extracted with EtOAc, and washed with 5% HCl, sat. aq. NaHCO$_3$, dried over Na$_2$SO$_4$, filtered, concentrated to afford the title compound. LCMS m/z=430/431 (M+1). $^1$H NMR (400 MHz, CDCl$_3$): δ 6.86 (s, 1 H), 6.14 (s, 1 H), 4.11-4.13 (m, 2 H), 3.71 (d, J=16.8 Hz, 1 H), 3.14 (d, J=16.8 Hz, 1 H), 1.87 (s, 3 H), 1.36 (s, 9 H), 1.22 (t, J=6.8 Hz, 3 H).

Step 3: (S)-ethyl 3-amino-3-(5-bromo-3-chlorothiophen-2-yl)butanoate

To a solution of (S)-ethyl 3-(5-bromo-3-chlorothiophen-2-yl)-3-((R)-1,1-dimethyl-ethylsulfinamido)butanoate (10 g, 23 mmol) in DCM (100 mL) was added HCl/dioxane (10 mL, 4 M) at 0° C. and stirred at RT for 1 h. The mixture was concentrated to afford the title compound. LCMS m/z=326/328 (M+1).

Step 4: (S)-ethyl 3-(5-bromo-3-chlorothiophen-2-yl)-3-(3-ethoxy-3-oxopropanamido) butanoate A mixture of (S)-ethyl 3-amino-3-(5-bromo-3-chloroth-iophen-2-yl)butanoate (1.5 g, 4.7 mmol), malonic acid monoethyl ester (0.62 g, 4.7 mmol), HATU (2.68 g, 7.05 mmol) and DIEA (1.82 g, 14.1 mmol) in DMF (20 mL) was stirred at RT overnight. After quenched by water, the mixture was extracted with EtOAc. The combined extracts were dried over Na$_2$SO$_4$ and concentrated. The residue was purified by silica column to afford the title compound. LCMS m/z=440/442 (M+1).

Step 5: (6S)-ethyl 6-(5-bromo-3-chlorothiophen-2-yl)-6-methyl-2,4-dioxopiperidine-3-carboxylate To a solution of NaOEt in EtOH, which was prepared from Na (173 mg, 7.5 mmol) in EtOH (20 mL), was added (S)-ethyl 3-(5-bromo-3-chlorothiophen-2-yl)-3-(3-ethoxy-3-oxopropanamido)butanoate (1.1 g, 2.5 mmol). Then the mixture was heated to reflux for 1 h and quenched by H$_2$O and 2 M HCl, extracted with EtOAc. The combined EtOAc layers were dried over Na$_2$SO$_4$ and concentrated to afford the title compound. LCMS m/z=394/396 (M+1).

Step 6: (S)-6-(5-bromo-3-chlorothiophen-2-yl)-6-methylpiperidine-2,4-dione

The mixture of (6S)-ethyl 6-(5-bromo-3-chlorothiophen-2-yl)-6-methyl-2,4-dioxo-piperidine-3-carboxylate (0.9 g, 2.3 mmol) in CH$_3$CN (10 mL) and H$_2$O (0.1 mL) was heated to reflux for 16 hours, concentrated. The residue was purified by silica column (PE:EtOAc=5:1) to afford the title compound. LCMS m/z=322/324 (M+1). $^1$H NMR (400 MHz, CDCl$_3$): δ 7.40 (s, 1H), 6.89 (s, 1 H), 3.56-3.60 (m, 3 H), 3.65-3.69 (m, 1 H), 1.82 (s, 3 H).

Step 7: (S,E)-6-(5-bromo-3-chlorothiophen-2-yl)-3-((dimethylamino)methylene)-6-methylpiperidine-2,4-dione A solution of (S)-6-(5-bromo-3-chlorothiophen-2-yl)-6-methylpiperidine-2,4-dione (3 g, 9 mmol) in DMF-DMA (20 mL) was stirred at 100° C. for 3 h, concentrated at 30° C. under reduce pressure to afford the title compound. LCMS m/z=397/399 (M+1). $^1$H NMR (400 MHz, CDCl$_3$): δ 7.88 (s, 1 H), 6.80 (s, 1 H), 6.05 (brs, 1 H), 3.32-3.35 (m, 4 H), 3.11 (s, 3 H), 2.71-2.79 (m, 1 H), 2.02 (s, 3 H).

Step 8: (S)-7-(5-bromo-3-chlorothiophen-2-yl)-7-methyl-7,8-dihydropyrido[4,3-d]pyrimidin-5(6H)-one To a solution of (S,E)-6-(5-bromo-3-chlorothiophen-2-yl)-3-((dimethylamino)-methylene)-6-methylpiperidine-2,4-dione (2.5 g, 6.6 mmol) in EtOH (30 mL) was added NaOEt (448 mg, 6.6 mmol) and methanimidamide monoacetate (529 mg, 6.6 mmol) at 25° C. The mixture was stirred at 80° C. for 12 h, and quenched by water, extracted with EtOAc. The combined extracts were washed with brine, dried over Na$_2$SO$_4$, concentrated. The residue was purified by column (PE:EtOAc=1:1) to afford the title compound. LCMS m/z=358/360 (M+1). $^1$H NMR (400 MHz, CDCl$_3$): δ 9.24 (s, 2 H), 6.87 (s, 1 H), 4.00-4.15 (m, 1 H), 3.35-3.40 (m, 1H), 1.96 (s, 3 H).

Step 9: (S)-7-(5-bromo-3-chlorothiophen-2-yl)-7-methyl-7,8-dihydropyrido[4,3-d]pyrimidine-5(6H)-thione To a solution of (S)-7-(5-bromo-3-chlorothiophen-2-yl)-7-methyl-7,8-dihydropyrido[4,3-d]pyrimidin-5(6H)-one (2 g, 5.9 mmol) in toluene (15 mL) was added Lawesson's reagent (1.43 g, 3.54 mmol). The mixture was heated to reflux for 1 h, concentrated. The residue was purified by silica column (PE:EtOAc=1:1) to afford the title compound. LCMS m/z=374/376 (M+1).

Step 10: (S)-7-(5-bromo-3-chlorothiophen-2-yl)-7-methyl-5-(methylthio)-7,8-dihydropyrido[4,3-d]pyrimidine To a solution of (S)-7-(5-bromo-3-chlorothiophen-2-yl)-7-methyl-7,8-dihydropyrido[4,3-d]pyrimidine-5(6H)-thione (1.5 g, 4.6 mmol) in THF (30 mL) was added MeI (1.14 g, 8.62 mmol) and NaHCO$_3$ (1.83 g, 17.2 mmol). The mixture was heated at 40° C. for 1 h, filtered. The filtrate was concentrated and purified by silica column (PE:EtOAc=1:1) to afford the title compound. LCMS m/z=388/390 (M+1). $^1$H NMR (400 MHz, CDCl$_3$): δ 9.14 (s, 1 H), 8.86 (s, 1 H), 6.87 (s, 1 H), 3.81-3.86 (m, 1 H), 3.15-3.19 (m, 1 H), 2.60 (s, 3 H), 1.49 (s, 3H).

Step 11: (S)-7-(5-bromo-3-chlorothiophen-2-yl)-7-methyl-7,8-dihydropyrido[4,3-d]pyrimidin-5(6H)-imine A solution of (S)-7-(5-bromo-3-chlorothiophen-2-yl)-7-methyl-5-(methylthio)-7,8-dihydropyrido[4,3-d]pyrimidine (0.5 g, 1.3 mmol) in MeOH (30 mL) saturated with NH$_3$ (gas) in the sealed tube was stirred at 100° C. for 48 h. The solution was concentrated and purified by silica column (PE:EtOAc=1:1) to afford the title compound. LCMS m/z=357 (M+1). $^1$H NMR (400 MHz, CD$_3$OD): δ 9.31 (s, 1 H), 9.27 (s, 1 H), 7.01 (s, 1 H), 3.95-4.00 (m, 1 H), 3.60-3.64 (m, 1 H), 1.96 (s, 3 H).

Method B2

Synthesis of (S)-7-(5-bromo-3-chlorothiophen-2-yl)-7-methyl-7,8-dihydropyrido[4,3-d]pyrimidin-5(6H)-imine (B12)

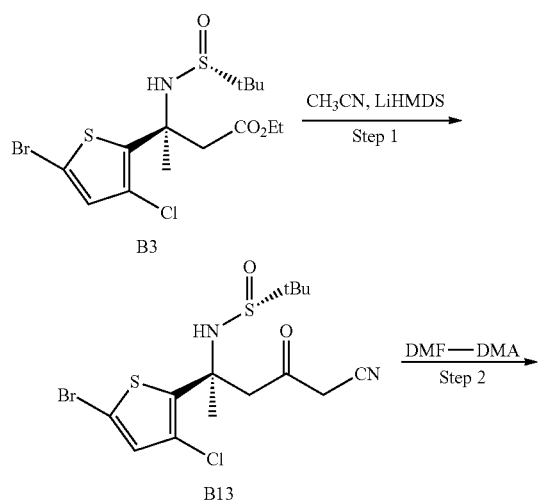

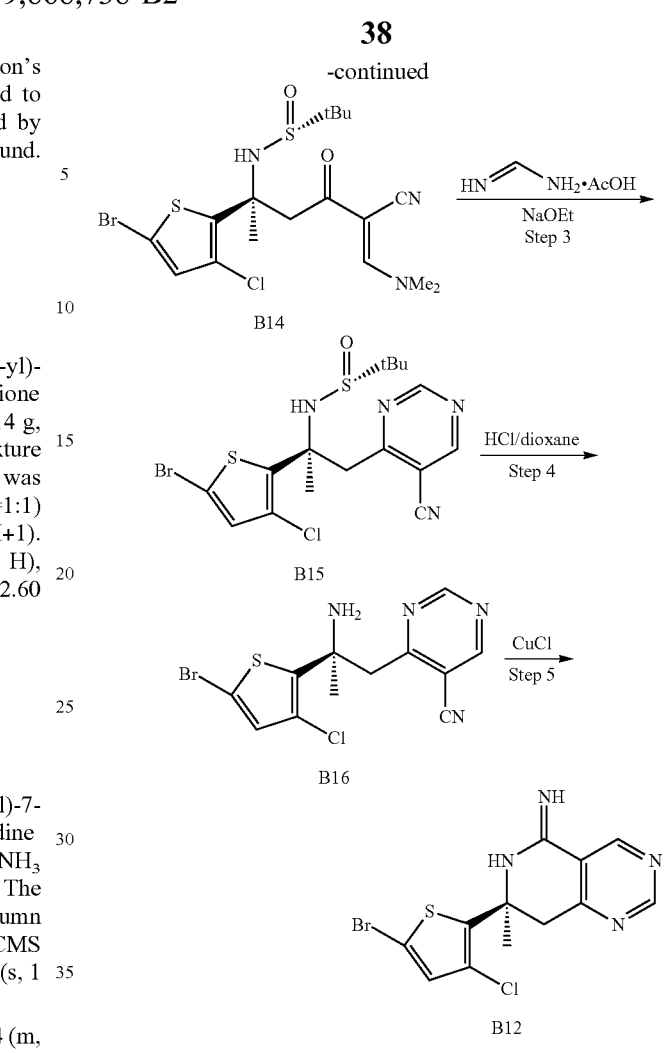

Step 1: (R)-N-((S)-2-(5-bromo-3-chlorothiophen-2-yl)-5-cyano-4-oxopentan-2-yl)-2-methylpropane-2-sulfinamide To a solution of CH$_3$CN (95 mg, 2.32 mmol) in THF (10 mL) was added LiHMDS (7 mL, 1 M in THF, 7 mmol) dropwise at −78° C. After stirring for 10 mins, the reaction mixture was added a solution of (S)-ethyl 3-(5-bromo-3-chlorothiophen-2-yl)-3-((R)-1,1-dimethylethylsulfinamido) butanoate (1 g, 2.32 mmol) in THF (5 mL) dropwise. The resulting mixture was stirred at −78° C. for 0.5 h, and RT for 3 h, quenched with H$_2$O, extracted with EtOAc. The organic layers were washed with brine, dried over Na$_2$SO$_4$, concentrated and purified by silica column chromatography (PE: EtOAc=10:1) to afford the title compound. LCMS m/z=425/427 (M+1). $^1$H NMR (400 MHz, CDCl$_3$): δ 6.74 (s, 1 H), 4.07-4.12 (m, 1H), 3.44 (s, 2 H), 3.34-3.38 (m, 1 H), 1.69 (s, 3 H), 1.22 (s, 9 H).

Step 2: (R)-N-((S,E)-2-(5-bromo-3-chlorothiophen-2-yl)-5-cyano-6-(dimethylamino)-4-oxohex-5-en-2-yl)-2-methylpropane-2-sulfinamide A solution of (R)-N-((S)-2-(5-bromo-3-chlorothiophen-2-yl)-5-cyano-4-oxopentan-2-yl)-2-methylpropane-2-sulfinamide (0.6 g, 1.4 mmol) in DMF-DMA (10 mL) was stirred at 100° C. for 1 h, and concentrated at 30° C. under reduce pressure to afford the title compound. LCMS m/z=480/482 (M+1). ¹H NMR (400 MHz, CDCl₃): δ 7.72 (s, 1 H), 6.75 (s, 1 H), 4.30-4.34 (m, 1 H), 3.36 (s, 3 H), 3.27-3.31 (m, 1 H), 3.18 (s, 3 H), 1.77 (s, 3 H), 1.28 (s, 9 H).

Step 3: (R)-N-((S)-2-(5-bromo-3-chlorothiophen-2-yl)-1-(5-cyanopyrimidin-4-yl)propan-2-yl)-2-methylpropane-2-sulfinamide To a solution of (R)-N-((S,E)-2-(5-bromo-3-chlorothiophen-2-yl)-5-cyano-6-(dimethylamino)-4-oxo hex-5-en-2-yl)-2-methylpropane-2-sulfinamide (0.6 g, 1.2 mmol) in EtOH (10 mL) was added TEA (242 mg, 2.4 mmol) and methanimidamide monoacetate (187 mg, 1.9 mmol) at 25° C., then stirred at 80° C. for 8 h. The mixture was diluted with water, extracted with EtOAc. The combined extracts were washed with brine, dried over Na₂SO₄, concentrated. The residue was purified by silica column (PE:EtOAc=1:1) to afford the title compound. LCMS m/z=461/463 (M+1). ¹H NMR (400 MHz, CDCl₃): δ 9.10 (s, 1 H), 8.86 (s, 1 H), 6.98 (s, 1 H), 4.38-4.43 (m, 1 H), 3.84-3.88 (m, 1 H), 1.94 (s, 3 H), 1.33 (s, 9 H).

Step 4: (S)-4-(2-amino-2-(5-bromo-3-chlorothiophen-2-yl)propyl)pyrimidine-5-carbonitrile To a solution of (R)-N-((S)-2-(5-bromo-3-chlorothiophen-2-yl)-1-(5-cyanopyrimidin-4-yl)propan-2-yl)-2-methylpropane-2-sulfinamide (500 mg, 1.1 mmol) in DCM (10 mL) was added HCl/dioxane (1 mL, 4 M) and stirred for 2 h. The mixture was concentrated to give afford the title compound. LCMS m/z=357/359 (M+1).

Step 5: (S)-7-(5-bromo-3-chlorothiophen-2-yl)-7-methyl-7,8-dihydropyrido[4,3-d]pyrimidin-5(6H)-imine A solution of (S)-4-(2-amino-2-(5-bromo-3-chlorothiophen-2-yl)propyl)pyrimidine-5-carbonitrile (400 mg, 1.1 mmol) and CuCl (194 mg, 1.7 mmol) in EtOH (15 mL) was refluxed under N₂ for 5 h. The reaction mixture was diluted with water and extracted with EtOAc. The combined extracts were washed with water and brine, dried with Na₂SO₄, concentrated. The residue was purified by silica column (PE:EtOAc=2:1) to give afford the title compound. LCMS m/z=357 (M+1). ¹H NMR (400 MHz, CDCl₃): δ 9.20 (s, 1 H), 9.09 (s, 1 H), 6.81 (s, 1 H), 3.64-3.69 (m, 1 H), 3.49-3.54 (m, 1 H), 1.72 (s, 3 H).

Method C

Synthesis of (S)-7-(4-bromothiophen-2-yl)-8,8-difluoro-7-methyl-7,8-dihydro-pyrido[4,3-d]pyrimidin-5(6H)-imine (C7)

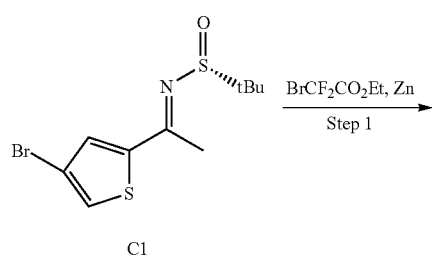

Step 1: (S)-ethyl 3-(4-bromothiophen-2-yl)-3-((R)-1,1-dimethylethylsulfinamido)-2,2-difluorobutanoate To a mixture of Zn dust (10.6 g, 0.16 mol) and CuCl (1.62 g, 16 mmol) in dry THF (100 mL) was heated to reflux and stirred vigorously for 30 min. The heating bath was removed. A solution of ethyl 2-bromo-2, 2-difluoroacetate (8.2 g, 40 mmol) was added slowly until refluxing was re-initiated. The addition was continued at a rate that maintained a controllable refluxing. Once addition was complete, the resulting mixture was stirred at 25° C. for 30 min, then at 50° C. for 30 min. The reaction mixture was cooled to 0°

C. A solution of (R,E)-N-(1-(4-bromothiophen-2-yl)ethylidene)-2-methylpropane-2-sulfinamide (5 g, 16 mmol) in THF (20 mL) was added slowly. After stirring at 0° C. for 4 hours, the mixture was filtered. The filtrate was washed with 5% HCl, saturated aqueous NaHCO₃ and brine. The organic layer was dried over Na₂SO₄ and concentrated to give afford the title compound. LCMS m/z=432/434 (M+1). ¹H NMR (400 MHz, CDCl₃): δ 7.24 (s, 1 H), 7.01 (s, 1 H), 4.22-4.30 (m, 2H), 1.95 (s, 3 H), 1.28 (s, 9 H), 1.25 (t, J=7.2 Hz, 3 H).

Step 2: 4-bromo-2-((S)-5-cyano-2-(((R)-cyanosulfinyl)amino)-3,3-difluoro-4-oxo-pentan-2-yl)thiophene To a solution of acetonitrile (0.11 g, 2.5 mmol) in THF (5 mL) was added LiHMDS (7 mL, 6.9 mmol, 1 M in THF) at −78° C. After stirring at −78° C. for 1 h, the mixture was added a solution of (S)-ethyl 3-(4-bromothiophen-2-yl)-3-((R)-1,1-dimethylethyl sulfinamido)-2,2-difluorobutanoate (1 g, 2.3 mmol) in THF (10 mL) and stirred at RT for 1 h. The mixture was quenched by H₂O, extracted with EtOAc. The combined extracts were dried over Na₂SO₄, concentrated, purified by silica column (PE:EtOAc=1:2) to give afford the title compound. LCMS m/z=427/429 (M+1). ¹H NMR (400 MHz, CDCl₃): δ 7.16 (s, 1 H), 6.9 (s, 1 H), 3.47 (s, 2 H), 1.76 (s, 3 H), 1.24 (s, 9 H).

Step 3: ((S,E)-5-(4-bromothiophen-2-yl)-2-cyano-5-(((R)-cyanosulfinyl)amino)-4,4-difluoro-3-oxohex-1-en-1-yl)dimethylamine To a mixture of 4-bromo-2-((S)-5-cyano-2-(((R)-cyanosulfinyl)amino)-3,3-difluoro-4-oxopentan-2-yl)thiophene (0.55 mg, 1.28 mmol) in DMF-DMA (8 mL) and heated at 40° C. overnight. The mixture was concentrated and purified by silica column (PE:EtOAc=1:2) to ive afford the title compound. LCMS m/z=440/442 (M+1). ¹H NMR (400 MHz, CD₃OD): δ 9.79 (s, 1 H), 7.13 (s, 1 H), 6.96 (s, 1 H), 3.42 (s, 1 H), 3.25 (s, 1 H), 1.87 (s, 1 H), 1.21 (s, 9H).

Step 4: (R)-N-((S)-2-(4-bromothiophen-2-yl)-1-(5-cyanopyrimidin-4-yl)-1,1-difluoropropan-2-yl)-2-methylpropane-2-sulfinamide To a solution of ((S,E)-5-(4-bromothiophen-2-yl)-2-cyano-5(((R)-cyanosulfinyl)amino)-4,4-difluoro-3-oxohex-1-en-1-yl)dimethylamine (0.1 g, 0.21 mmol) and formamidinium acetate (32 mg, 0.31 mmol) in EtOH (2 mL) was added TEA (42 mg, 0.41 mmol). The mixture was refluxed for 6 h, and concentrated. The residue was concentrated and purified by silica column (PE:EtOAc=2:1) to afford the title compound. LCMS m/z=421/423 (M+1). ¹H NMR (400 MHz, CDCl₃): δ 9.32 (s, 1 H), 9.05 (s, 1 H), 7.20 (s, 1 H), 7.15 (s, 1 H), 2.00 (s, 3 H), 1.23 (s, 9 H).

Step 5: (S)-4-(2-amino-2-(4-bromothiophen-2-yl)-1,1-difluoropropyl)pyrimidine-5-carbonitrile To a solution of (R)-N-((S)-2-(4-bromothiophen-2-yl)-1-(5-cyanopyrimidin-4-yl)-1,1-difluoropropan-2-yl)-2-methylpropane-2-sulfinamide (0.17 g, 0.37 mmol) in DCM (20 mL) cooled to 0° C. was added HCl/dioxane (2 mL, 4 M) and stirred at RT for 2 h. The reaction mixture was concentrated and dissolved in DCM. The solution was washed with saturated NaHCO₃ (aq.), dried over Na₂SO₄, concentrated to afford the title compound. LCMS m/z=359/361 (M+1).

Step 6: (S)-7-(4-bromothiophen-2-yl)-8,8-difluoro-7-methyl-7,8-dihydropyrido[4,3-d]pyrimidin-5(6H)-imine A suspension of (S)-4-(2-amino-2-(4-bromothiophen-2-yl)-1,1-difluoropropyl)pyrimidine-5-carbonitrile (0.13 g, 0.36 mmol) and CuCl (54 mg, 0.54 mmol) in EtOH (5 mL) was heated to reflux overnight, diluted with DCM (20 mL), and filtered. The filtrate was concentrated and purified by p-TLC (PE:EtOAc=3:1) to afford the title compound. LCMS m/z=359 (M+1). ¹H NMR (400 MHz, CD₃OD): δ 9.37 (s, 1 H), 9.23 (s, 1 H), 7.26 (s, 1 H), 6.99 (s, 1 H), 1.65 (s, 3 H).

Method D

Synthesis of (S)-tert-butyl(7-(5-amino-2-fluorophenyl)-2,7-dimethyl-7,8-dihydro-pyrido[4,3-d]pyrimidin-5(6H)-ylidene)carbamate (D16)

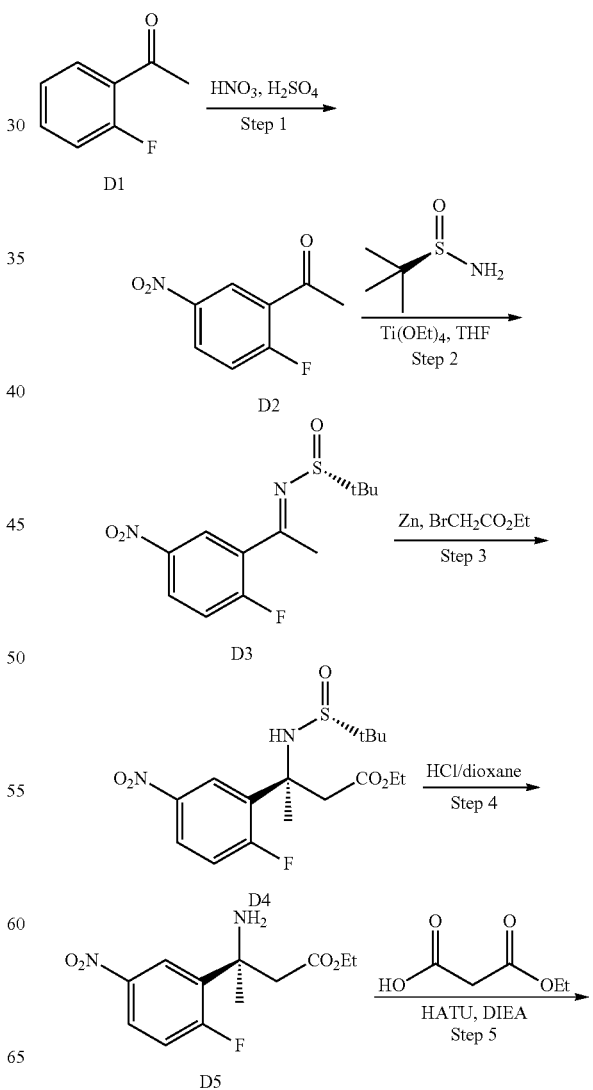

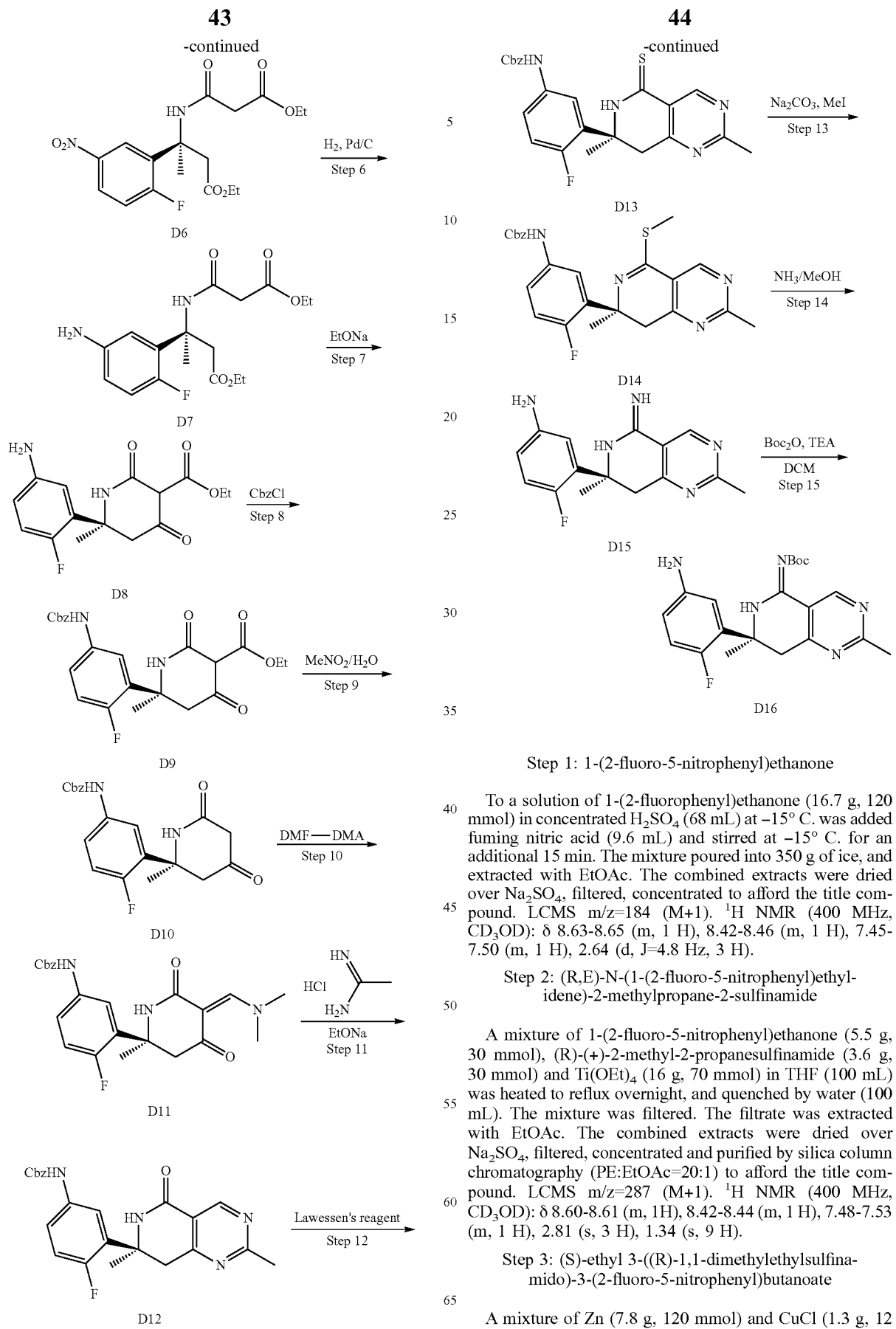

Step 1: 1-(2-fluoro-5-nitrophenyl)ethanone

To a solution of 1-(2-fluorophenyl)ethanone (16.7 g, 120 mmol) in concentrated $H_2SO_4$ (68 mL) at −15° C. was added fuming nitric acid (9.6 mL) and stirred at −15° C. for an additional 15 min. The mixture poured into 350 g of ice, and extracted with EtOAc. The combined extracts were dried over $Na_2SO_4$, filtered, concentrated to afford the title compound. LCMS m/z=184 (M+1). $^1$H NMR (400 MHz, $CD_3OD$): δ 8.63-8.65 (m, 1 H), 8.42-8.46 (m, 1 H), 7.45-7.50 (m, 1 H), 2.64 (d, J=4.8 Hz, 3 H).

Step 2: (R,E)-N-(1-(2-fluoro-5-nitrophenyl)ethylidene)-2-methylpropane-2-sulfinamide A mixture of 1-(2-fluoro-5-nitrophenyl)ethanone (5.5 g, 30 mmol), (R)-(+)-2-methyl-2-propanesulfinamide (3.6 g, 30 mmol) and Ti(OEt)$_4$ (16 g, 70 mmol) in THF (100 mL) was heated to reflux overnight, and quenched by water (100 mL). The mixture was filtered. The filtrate was extracted with EtOAc. The combined extracts were dried over $Na_2SO_4$, filtered, concentrated and purified by silica column chromatography (PE:EtOAc=20:1) to afford the title compound. LCMS m/z=287 (M+1). $^1$H NMR (400 MHz, $CD_3OD$): δ 8.60-8.61 (m, 1H), 8.42-8.44 (m, 1 H), 7.48-7.53 (m, 1 H), 2.81 (s, 3 H), 1.34 (s, 9 H).

Step 3: (S)-ethyl 3-((R)-1,1-dimethylethylsulfinamido)-3-(2-fluoro-5-nitrophenyl)butanoate A mixture of Zn (7.8 g, 120 mmol) and CuCl (1.3 g, 12 mmol) in 40 mL of THF was heated to reflux for 0.5 h and cooled. Ethyl bromoacetate (5.5 g, 30 mmol) in 15 mL of THF was added dropwise to above mixture, and stirred at RT for 0.5 h, then heated to 50° C. for 0.5 h. The resulting mixture was cooled to 0° C., and added a solution of (R,E)-N-(1-(2-fluoro-5-nitrophenyl)ethylidene)-2-methyl-propane-2-sulfinamide (3.5 g, 12 mmol) in 10 mL of THF. After stirring at 0° C. for 1 h, the mixture was filtered. The filtrate was extracted with EtOAc, and washed with 5% HCl, sat. aq NaHCO$_3$, dried over Na$_2$SO$_4$, filtered, concentrated to afford the title compound. LCMS m/z=375 (M+1). H NMR (400 MHz, CD$_3$OD): δ 8.61-8.62 (m, 1 H), 8.42-8.45 (m, 1 H), 7.48-7.55 (m, 1 H), 4.15-4.26 (q, J=7.2 Hz, 2 H), 2.95-3.25 (m, 2 H), 1.95 (s, 3 H), 1.25 (s, 9 H), 1.22 (t, J=7.2 Hz, 3 H).

Step 4: (S)-ethyl 3-amino-3-(2-fluoro-5-nitrophenyl) butanoate

To a solution of (S)-ethyl 3-((R)-1,1-dimethylethylsulfinamido)-3-(2-fluoro-5-nitro-phenyl)butanoate (11 g, 30 mmol) in DCM (100 mL) was added HCl/dioxane (20 mL, 4 M), the mixture was stirred at RT for 1 h. The mixture was concentrated to afford the title compound. LCMS m/z=271 (M+1).

Step 5: (S)-ethyl 3-(3-ethoxy-3-oxopropanamido)-3-(2-fluoro-5-nitrophenyl)butanoate A mixture of (S)-ethyl 3-amino-3-(2-fluoro-5-nitrophenyl)butanoate (7.8 g, 30 mmol), malonic acid monoethyl ester (5.3 g, 42 mmol), HATU (32 g, 85 mmol) and DIEA (21 g, 165 mmol) in DMF (100 mL) was stirred at RT overnight. After quenched by water, the mixture was extracted with EtOAc. The combined extracts were dried over Na$_2$SO$_4$ and concentrated. The residue was purified by silica column to afford the title compound. LCMS m/z=385 (M+1). $^1$H NMR (400 MHz, CD$_3$OD): δ 8.20-8.32 (m, 1 H), 8.16-8.19 (m, 1 H), 7.26-7.31 (m, 1H), 4.14 (q, J=7.2 Hz, 2 H), 4.02 (q, J=7.2 Hz, 2 H), 3.33 (d, J=14.4 Hz, 1 H), 3.12 (d, J=14.4 Hz, 1 H), 2.75 (s, 2 H), 1.84 (s, 3 H), 1.22 (t, J=7.2 Hz, 3 H), 1.13 (t, J=7.2 Hz, 3 H).

Step 6: (S)-ethyl 3-(5-amino-2-fluorophenyl)-3-(3-ethoxy-3-oxopropanamido)butanoate To a solution of (S)-ethyl 3-(3-ethoxy-3-oxopropanamido)-3-(2-fluoro-5-nitrophenyl) butanoate (5.7 g, 15 mmol) in MeOH (150 mL) was added Pd/C (1.5 g, 10%) and the solution was stirred at room temperature under H$_2$ (45 psi) for 7 h. The reaction mixture was filtered and the filtrate was concentrated to afford the title compound. LCMS m/z=355 (M+1). $^1$H NMR (400 MHz, CDCl$_3$): δ 7.98 (s, 1 H), 8.21-8.32 (m, 1 H), 8.15-8.19 (m, 1 H), 7.25-7.31 (m, 1 H), 4.15 (q, J=7.2 Hz, 2 H), 4.05 (q, J=7.2 Hz, 2 H), 3.35 (s, 2 H), 3.31 (d, J=14.4 Hz, 1 H), 2.95 (d, J=14.4 Hz, 1 H), 2.75 (s, 2 H), 1.84 (s, 3 H), 1.21 (t, J=7.2 Hz, 3 H), 1.15 (t, J=7.2 Hz, 3 H).

Step 7: (6S)-ethyl 6-(5-amino-2-fluorophenyl)-6-methyl-2,4-dioxopiperidine-3-carboxylate To a solution of NaOEt in EtOH, which was prepared from Na (580 mg, 25 mmol) in EtOH (25 mL), was added (S)-ethyl 3-(5-amino-2-fluorophenyl)-3-(3-ethoxy-3-oxopropanamido)butanoate (4.2 g, 12 mmol). Then the mixture was heated to reflux for 1 h and quenched by H$_2$O and 2 M HCl until pH 6. The resulting solution was extracted with EtOAc. The combined EtOAc layers were dried over Na$_2$SO$_4$ and concentrated to afford the title compound. LCMS m/z=309 (M+1).

Step 8: (6S)-ethyl 6-(5-(((benzyloxy)carbonyl)amino)-2-fluorophenyl)-6-methyl-2,4-dioxopiperidine-3-carboxylate To a solution of (6S)-ethyl 6-(5-amino-2-fluorophenyl)-6-methyl-2,4-dioxopiperidine-3-carboxylate (1.2 g, 4 mmol) and Na$_2$CO$_3$ (850 mg, 8 mmol) in H$_2$O (20 mL) and acetone (20 mL) at 0° C. was added dropwise Cbz-Cl (700 mg, 4 mmol). The mixture was stirred at 0° C. for 0.5 h and extracted with DCM. The combined extracts were dried over Na$_2$SO$_4$ and concentrated. The residue was purified by silica column to afford the title compound. LCMS m/z=443 (M+1). $^1$H NMR (400 MHz, CD$_3$OD): δ 7.35-7.45 (m, 7 H), 6.91-6.98 (m, 1 H), 5.15 (s, 2 H), 4.15 (q, J=7.2 Hz, 2 H), 3.38 (s, 1 H), 2.93 (d, J=14.4 Hz, 1 H), 2.68 (d, J=14.4 Hz, 1 H), 1.65 (s, 3 H), 1.26 (t, J=7.2 Hz, 3 H).

Step 9: (S)-benzyl (4-fluoro-3-(2-methyl-4,6-dioxopiperidin-2-yl)phenyl)carbamate A solution of (6S)-ethyl 6-(5-(((benzyloxy)carbonyl)amino)-2-fluorophenyl)-6-methyl-2,4-dioxopiperidine-3-carboxylate (5 g, 11.3 mmol) in MeNO$_2$ (150 mL) and H$_2$O (0.5 mL) was heated to reflux for 15 h, and then concentrated. The residue was purified by silica column to afford the title compound. LCMS m/z=371 (M+1). $^1$H NMR (400 MHz, CDCl$_3$): δ 7.19-7.33 (m, 6 H), 6.78-6.99 (m, 2 H), 6.72 (s, 1 H), 5.08 (s, 2 H), 3.32 (d, J=14.4 Hz, 1 H), 2.96-3.16 (m, 2 H), 2.64 (d, J=14.4 Hz, 1 H), 2.65 (s, 1 H), 1.66 (s, 3 H).

Step 10: (S,E)-benzyl (3-(5-((dimethylamino)methylene)-2-methyl-4,6-dioxo piperidin-2-yl)-4-fluorophenyl)carbamate A mixture of (S)-benzyl (4-fluoro-3-(2-methyl-4,6-dioxopiperidin-2-yl)phenyl)carbamate (500 mg, 1.3 mmol) in DMF-DMA (15 mL) was heated to reflux for 1 h, concentrated to afford the title compound. LCMS m/z=426 (M+1).

Step 11: (S)-benzyl (3-(2,7-dimethyl-5-oxo-5,6,7,8-tetrahydropyrido[4,3-d]pyrimidin-7-yl)-4-fluorophenyl)carbamate To a solution of (S,E)-benzyl (3-(5-((dimethylamino)methylene)-2-methyl-4,6-dioxopiperidin-2-yl)-4-fluorophenyl)carbamate (4.6 g, 10 mmol) in EtOH (100 mL) was added NaOEt (680 mg, 10 mmol) and methanimidamide monoacetate (248 mg, 10 mmol) at 25° C., then stirred at 80° C. for 3 h. The mixture was diluted with water, extracted with EtOAc. The combined extracts were washed with brine, dried over Na$_2$SO$_4$, concentrated. The residue was purified by silica column (PE:EtOAc=1:2) to afford the title compound. LCMS m/z=421 (M+1). $^1$H NMR (400 MHz, CDCl$_3$): δ 8.87 (s, 1 H), 8.20 (s, 1 H), 7.33-7.35 (m, 2 H), 7.05-7.21 (m, 5 H), 5.44 (s, 2 H), 3.42-3.68 (m, 2 H), 2.73 (s, 3 H), 1.80 (s, 3 H).

Step 12: (S)-benzyl (3-(2,7-dimethyl-5-thioxo-5,6,7,8-tetrahydropyrido[4,3-d]pyrimidin-7-yl)-4-fluorophenyl)carbamate To a solution of (S)-benzyl (3-(2,7-dimethyl-5-oxo-5,6,7,8-tetrahydropyrido[4,3-d]pyrimidin-7-yl)-4-fluorophenyl)

carbamate (3 g, 7 mmol) in toluene (30 mL) was added Lawesson's reagent (1.4 g, 3 mmol) and heated to reflux for 1 h. The mixture was concentrated and purified by column (PE:EA=1:1) to afford the title compound. LCMS m/z=437 (M+1). ¹H NMR (400 MHz, CDCl₃): δ 9.42 (s, 1 H), 8.37 (s, 1 H), 7.34-7.35 (m, 2 H), 7.25-7.32 (m, 5H), 5.14 (s, 2 H), 3.40-3.71 (m, 2 H), 2.71 (s, 3 H), 1.85 (s, 3 H).

Step 13: (S)-benzyl (3-(2,7-dimethyl-5-(methylthio)-7,8-dihydropyrido[4,3-d]pyrimidin-7-yl)-4-fluorophenyl)carbamate To a solution of (S)-benzyl (3-(2,7-dimethyl-5-thioxo-5,6,7,8-tetrahydropyrido[4,3-d]pyrimidin-7-yl)-4-fluorophenyl)carbamate (4.4 g, 10 mmol) in THF (50 mL) were added MeI (2.84 g, 20 mmol) and NaHCO₃ (1.68 g, 20 mmol) and heated to 40° C. for 16 h. After filtering, the filtrate was concentrated. The residue was purified by silica column (PE:EtOAc=3:1) to afford the title compound. LCMS m/z=451 (M+1). ¹H NMR (400 MHz, CDCl₃): δ 8.76 (s, 1 H), 7.80 (s, 1 H), 7.34-7.35 (m, 5 H), 7.00-7.24 (m, 1 H), 6.66 (s, 1 H), 5.18 (s, 2H), 3.10-3.51 (m, 2 H), 2.73 (s, 3 H), 2.61 (s, 3 H), 1.45 (s, 3 H).

Step 14: (S)-4-fluoro-3-(5-imino-2,7-dimethyl-5,6,7,8-tetrahydropyrido[4,3-d]pyrimidin-7-yl)aniline A solution of (S)-benzyl (3-(2,7-dimethyl-5-(methylthio)-7,8-dihydropyrido[4,3-d]pyrimidin-7-yl)-4-fluorophenyl) carbamate (750 mg, 2 mmol) in MeOH (30 mL) saturated with NH₃ (gas) in the sealed tube was stirred at 100° C. for 48 h. The solvent was removed to afford the title compound. m/z=286 (M+1). ¹H NMR (400 MHz, CD₃OD): δ 9.01 (s, 1 H), 6.80 (s, 1 H), 6.55-6.58 (m, 1 H), 6.38 (s, 1 H), 3.44-3.69 (m, 2 H), 2.73 (s, 3 H), 1.85 (s, 3 H).

Step 15: (S)-tert-butyl (7-(5-amino-2-fluorophenyl)-2,7-dimethyl-7,8-dihydropyrido[4,3-d]pyrimidin-5(6H)-ylidene)carbamate To a solution of (S)-4-fluoro-3-(5-imino-2,7-dimethyl-5,6,7,8-tetrahydropyrido[4,3-d]pyrimidin-7-yl)aniline (500 mg, 1.7 mmol) in DCM/MeOH (50:1, 20 mL) was added (Boc)₂O (370 mg, 1.7 mmol) and DIEA (670 mg, 5.2 mmol) and stirred at 0° C. for 6 h. The mixture was concentrated and purified by silica column (PE:EtOAc=1:1) to afford the title compound. LCMS m/z=386 (M+1). ¹H NMR (400 MHz, CD₃OD): δ 9.10 (s, 1 H), 6.79-6.84 (m, 1 H), 6.52-6.55 (m, 1 H), 6.42 (s, 1 H), 3.40-3.71 (m, 2 H), 2.65 (s, 3 H), 1.82 (s, 3H), 1.46 (s, 9 H).

Method E

Synthesis of (S)-tert-butyl(7-(5-amino-2-fluorophenyl)-7-(difluoromethyl)-2-methyl-7,8-dihydropyrido[4,3-d]pyrimidin-5(6H)-ylidene)carbamate (E11)

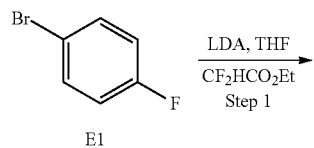

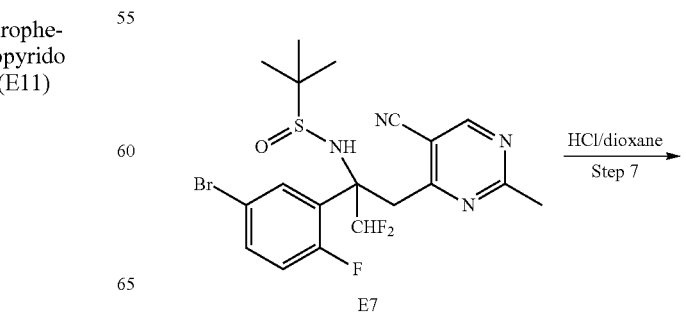

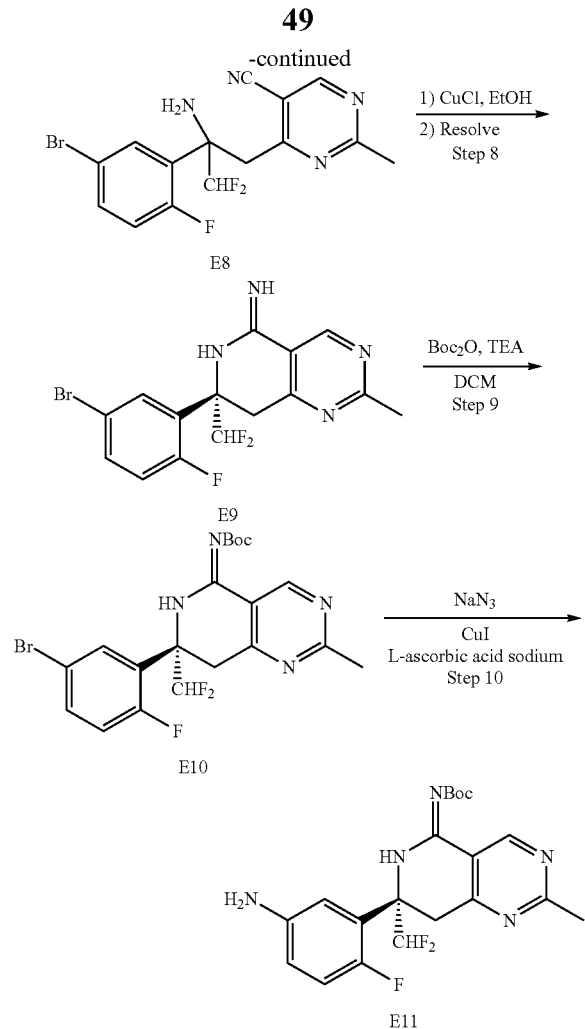

concentrated. The residue was purified by silica column (PE:EtOAc=10:1) to afford the title compound. LCMS m/z=356. $^1$H NMR (400 MHz, CDCl$_3$): δ 7.61-7.41 (m, 2 H), 7.06-6.95 (m, 1 H), 6.54-6.06 (m, 1 H), 1.35-1.27 (m, 9 H).

Step 3: methyl 3-(5-bromo-2-fluorophenyl)-3-(1,1-dimethylethylsulfinamido)-4,4-difluorobutanoate To a solution of methyl acetate (3.74 g, 50.5 mmol) in THF (150 mL) was added LDA (21 mL, 42.1 mmol, 2 N in THF) at −78° C. and stirred at −78° C. for 0.5 h. Triisopropoxytitanium (IV) chloride (84 mL, 84 mmol) was added dropwise at −78° C. for 0.5 h. Then (Z)-N-(1-(5-bromo-2-fluorophenyl)-2,2-difluoroethylidene)-2-methylpropane-2-sulfinamide (10 g, 28.1 mmol) was added at −78° C. for 0.5 h. The mixture was stirred at −78° C. for 1 h. The mixture was quenched with aq NH$_4$Cl, Filtrated and extracted with EtOAc. The combined extracts were washed with water and brine, dried with Na$_2$SO$_4$, filtered and concentrated. The residue was purified by silica column (PE:EtOAc=10:1) to afford the title compound. LCMS m/z=430/432 (M+1). $^1$H NMR (400 MHz, CDCl$_3$): δ 7.68-7.59 (m, 1 H), 7.54-7.41 (m, 1 H), 7.03-6.90 (m, 1 H), 6.58-6.08 (m, 1 H), 3.69 (d, J=14.1 Hz, 3 H), 3.43-3.20 (m, 2 H), 1.28 (d, J=1.6 Hz, 9 H).

Step 4: N-(2-(5-bromo-2-fluorophenyl)-5-cyano-1,1-difluoro-4-oxopentan-2-yl)-2-methylpropane-2-sulfinamide To a solution of acetonitrile (0.525 g, 12.78 mmol) in THF (100 mL) was added lithium bis(trimethylsilyl)amide (34.9 mL, 34.9 mmol, 1 M in THF) at −78° C. and stirred at −78° C. for 10 min. Then methyl 3-(5-bromo-2-fluorophenyl)-3-(1,1-dimethylethylsulfinamido)-4,4-difluorobutanoate (5 g, 11.62 mmol) was added and stirred at −78° C. for 1 h, then 25° C. for 2 h. The mixture was quenched with water, extracted with EtOAc. The combined extracts were washed with water and brine, dried with Na$_2$SO$_4$, filtered and concentrated. The residue was purified by silica column (PE:EtOAc=2:1) to afford the title compound. LCMS m/z=439/441 (M+1). $^1$H NMR (400 MHz, CDCl$_3$): δ 7.63 (t, J=6.7 Hz, 1 H), 7.55-7.43 (m, 1 H), 7.05-6.90 (m, 1 H), 6.42-5.97 (m, 1 H), 3.91-3.68 (m, 2 H), 3.67-3.59 (m, 2 H), 1.29 (s, 9 H).

Step 5: (E)-N-(2-(5-bromo-2-fluorophenyl)-5-cyano-6-(dimethylamino)-1,1-difluoro-4-oxohex-5-en-2-yl)-2-methylpropane-2-sulfinamide To a solution of N-(2-(5-bromo-2-fluorophenyl)-5-cyano-1,1-difluoro-4-oxopentan-2-yl)-2-methylpropane-2-sulfinamide (8 g, 18.21 mmol) in DMF-DMA (50 mL) was added and stirred at 50° C. for 1 h. The mixture was quenched with water, extracted with EtOAc. The combined extracts were washed with water and brine, dried with Na$_2$SO$_4$, filtered and concentrated to afford the title compound. LCMS m/z=494/496 (M+1).

Step 6: N-(2-(5-bromo-2-fluorophenyl)-3-(5-cyano-2-methylpyrimidin-4-yl)-1,1-difluoropropan-2-yl)-2-methylpropane-2-sulfinamide To a solution of (E)-N-(2-(5-bromo-2-fluorophenyl)-5-cyano-6-(dimethylamino)-1,1-difluoro-4-oxohex-5-en-2-yl)-2-methylpropane-2-sulfinamide (8 g, 16.65 mmol) in EtOH (100 mL) was added triethylamine (3.37 g, 33.3

Step 1: 1-(5-bromo-2-fluorophenyl)-2,2-difluoroethanone

To a solution of 1-bromo-4-fluorobenzene (40 g, 229 mmol) in THF (1000 mL) was added LDA (126 mL, 251 mmol, 2 N in THF) at −78° C. and stirred at −78° C. for 1 h. Then ethyl 2, 2-difluoroacetate (31.2 g, 251 mmol) was added dropwise and stirred at −78° C. for 3 h. The mixture was quenched with water, extracted with EtOAc. The combined extracts were washed with water and brine, dried with Na$_2$SO$_4$, filtered and concentrated. The residue was purified by silica column (PE:EtOAc=10:1) to afford the title compound. LCMS m/z=253 (M+1). $^1$H NMR (400 MHz, CDCl$_3$): δ 8.02 (dd, J=6.1, 2.5 Hz, 1 H), 7.72 (ddd, J=8.7, 4.4, 2.5 Hz, 1 H), 7.10 (dd, J=9.8, 9.0 Hz, 1 H), 6.22-6.54 ppm (m, 1 H).

Step 2: (Z)-N-(1-(5-bromo-2-fluorophenyl)-2,2-difluoroethylidene)-2-methylpropane-2-sulfinamide A suspension of 1-(5-bromo-2-fluorophenyl)-2,2-difluoroethanone (46 g, 182 mmol), 2-methylpropane-2-sulfinamide (33.1 g, 273 mmol) and tetraethoxytitanium (83 g, 364 mmol) in THF (100 mL) was stirred at 80° C. for 8 h. The reaction quenched with ice-water. The mixture filtered and extracted with EtOAc. The combined organic layers were washed with brine and dried over Na$_2$SO$_4$, filtered and mmol), acetimidamide hydrochloride (2.362 g, 24.98 mmol) and refluxed at 90° C. for 16 h. The mixture was concentrated, purified by silica column (PE:EtOAc=2:1) to afford the title compound. LCMS m/z=489/491 (M+1). $^1$H NMR (400 MHz, CDCl$_3$): δ 8.82 (d, J=2.3 Hz, 1 H), 7.86 (dd, J=2.2, 6.8 Hz, 0.5 H), 7.77-7.66 (m, 0.5 H), 7.57-7.45 (m, 1 H), 7.03-6.88 (m, 1 H), 6.59-6.37 (m, 1 H), 4.01-3.78 (m, 2 H), 2.80-2.64 (m, 3 H), 1.35-1.29 (m, 9 H).

Step 7: 4-(2-amino-2-(5-bromo-2-fluorophenyl)-3,3-difluoropropyl)-2-methylpyrimidine-5-carbonitrile To a solution of N-(2-(5-bromo-2-fluorophenyl)-3-(5-cyano-2-methylpyrimidin-4-yl)-1,1-difluoropropan-2-yl)-2-methylpropane-2-sulfinamide (5 g, 10.22 mmol) in DCM (60 mL) was added HCl/dioxane (10 mL) at 0° C., then warmed to 25° C., and stirred for another 2 h. The reaction mixture was concentrated, dissolved in MeOH, neutralized with aq. NaHCO$_3$ at 0° C., extracted with DCM. The organic layers were dried over Na$_2$SO$_4$ filtered and concentrated to afford the title compound. LCMS m/z=385/387 (M+1).

Step 8: (S)-7-(5-bromo-2-fluorophenyl)-7-(difluoromethyl)-2-methyl-7,8-dihydropyrido[4,3-d]pyrimidin-5(6H)-imine The mixture of 4-(2-amino-2-(5-bromo-2-fluorophenyl)-3,3-difluoropropyl)-2-methyl pyrimidine-5-carbonitrile (4 g, 10.38 mmol) and copper(I) chloride (2.056 g, 20.77 mmol) in EtOH (100 mL) was stirred at 80° C. for 21 h, concentrated. The residue was diluted with 15% NH$_3$ (aq.) solution and extracted with DCM. The combined layers were washed with brine, dried over Na$_2$SO$_4$ and concentrated. The residue was purified by silica column (PE:EtOAc=1:1) to afford the title compound. LCMS m/z=385/387 (M+1). 7-(5-bromo-2-fluorophenyl)-7-(difluoromethyl)-2-methyl-7,8-dihydropyrido[4,3-d]pyrimidin-5(6H)-imine was resolved by SFC to afford the title compound. $^1$H NMR (400 MHz, CD$_3$OD): δ 8.83 (s, 1 H), 7.55 (dd, J=2.3, 7.0 Hz, 1 H), 7.43 (dd, J=3.7, 8.4 Hz, 1 H), 7.02 (dd, J=8.6, 11.7 Hz, 1 H), 6.40-6.05 (m, 1 H), 3.65-3.56 (m, 1 H), 3.46-3.40 (m, 1 H), 2.66 (s, 3 H).

Step 9: (S)-tert-butyl (7-(5-bromo-2-fluorophenyl)-7-(difluoromethyl)-2-methyl-7,8-dihydropyrido[4,3-d]pyrimidin-5(6H)-ylidene)carbamate To a solution of (S)-7-(5-bromo-2-fluorophenyl)-7-(difluoromethyl)-2-methyl-7,8-dihydropyrido[4,3-d]pyrimidin-5(6H)-imine (350 mg, 0.909 mmol) in DCM (10 mL) was added BOC$_2$O (397 mg, 1.817 mmol), and DIEA (0.317 ml, 1.817 mmol). The mixture was stirred at 30° C. for 16 h, concentrated and purified by silica column (PE:EtOAc=3:1) to afford the title compound. LCMS m/z=485/487 (M+1).

Step 10: (S)-tert-butyl (7-(5-amino-2-fluorophenyl)-7-(difluoromethyl)-2-methyl-7,8-dihydropyrido[4,3-d]pyrimidin-5(6H)-ylidene)carbamate To a solution of (S)-tert-butyl (7-(5-bromo-2-fluorophenyl)-7-(difluoromethyl)-2-methyl-7,8-dihydropyrido[4,3-d]pyrimidin-5(6H)-ylidene)carbamate (250 mg, 0.515 mmol) and sodium azide (268 mg, 4.12 mmol) in EtOH/H$_2$O (15/5 mL) were added, copper(I) iodide (49.1 mg, 0.258 mmol), L-ascorbic acid sodium (73.3 mg, 0.515 mmol) and sodium ascorbate (51.0 mg, 0.258 mmol) at 25° C. under N$_2$ atmosphere, then the solution was stirred at 55° C. for 2 h. The solution was cooled and 5 ml NH$_3$ (sat. aq.) added, extracted with EtOAc. The combined layers were washed with brine, dried with Na$_2$SO$_4$, filtered and concentrated, purified by silica column (PE:EtOAc=3:1) to afford the title compound. LCMS m/z=422 (M+1). $^1$H NMR (400 MHz, CDCl$_3$): δ=9.29 (s, 1 H), 6.86 (dd, J=8.8, 11.8 Hz, 1 H), 6.54 (td, J=3.4, 8.5 Hz, 1 H), 6.49-6.18 (m, 2 H), 3.61 (d, J=8.8 Hz, 2 H), 2.74-2.63 (m, 3 H), 1.57 (s, 9 H).

Method F

Synthesis of (Z)-tert-butyl(7-(5-amino-2-fluorophenyl)-7-methyl-7,8-dihydropyrido[3,4-b]pyrazin-5(6H)-ylidene)carbamate (F8)

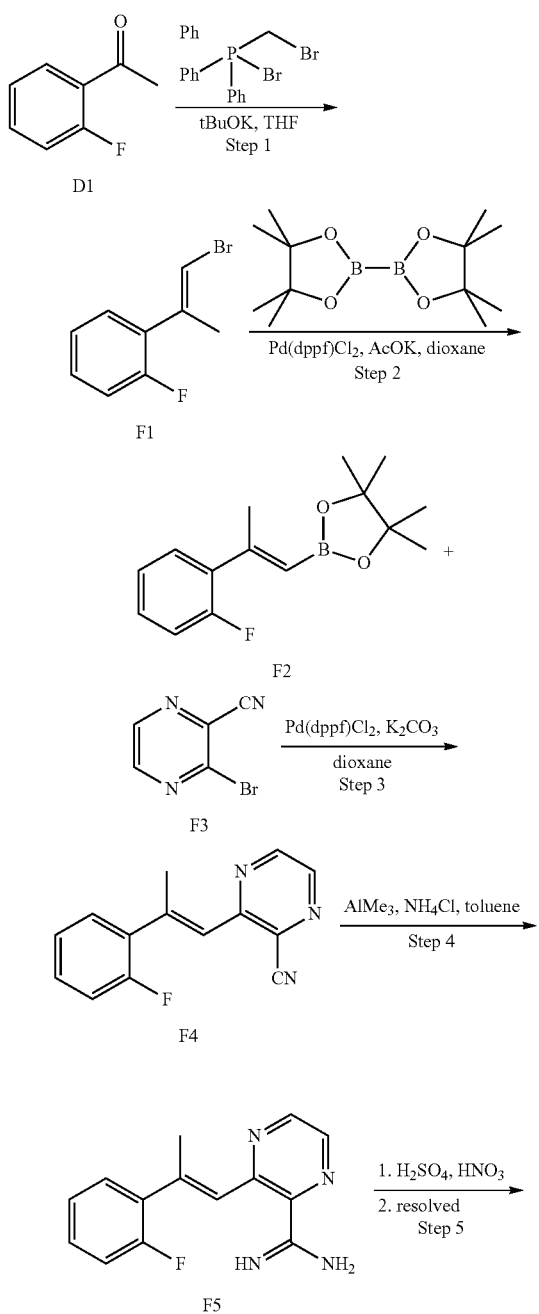

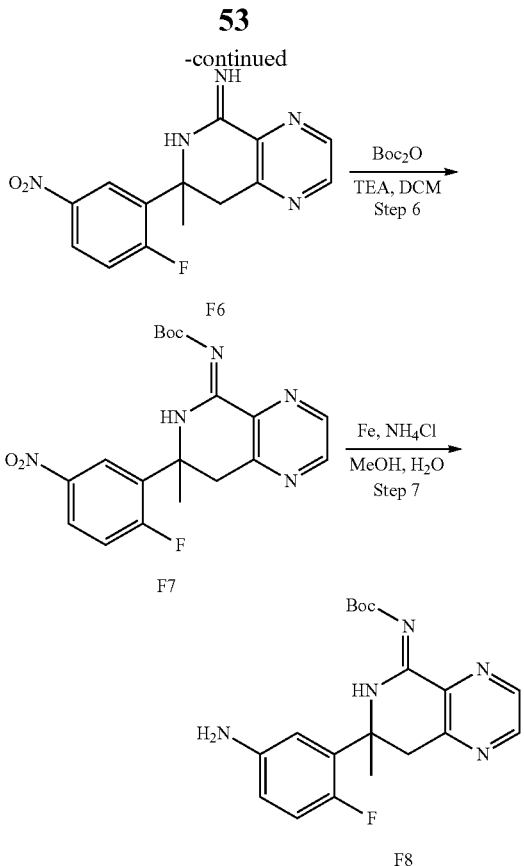

F6

F7

F8

Step 1: (E)-1-(1-bromoprop-1-en-2-yl)-2-fluorobenzene

To a solution of bromo(bromomethyl)triphenylphosphorane (18.47 g, 42.3 mmol) in THF (300 mL) was added potassium 2-methylpropan-2-olate (4.39 g, 39.1 mmol) in THF (40 mL) at 0° C. After 30 min, 1-(2-fluorophenyl) ethanone (4.5 g, 32.6 mmol) was added. The mixture was stirred at 0° C. for 4 h, quenched with water, extracted with EtOAc. The combined extracts were washed with water and brine, dried over $Na_2SO_4$, concentrated and purified by silica column (PE) to afford the title compound. $^1$H NMR (400 MHz, CDCl3): δ 7.41-7.02 (m, 4 H), 6.48-6.26 (m, 1 H), 2.20 (d, J=7.8 Hz, 1.5 H), 2.13 (d, J=0.8 Hz, 1.5 H).

Step 2: (E)-2-(2-(2-fluorophenyl)prop-1-en-1-yl)-4,4,5,5-tetramethyl-1,3,2-dioxa-borolane A mixture of (E)-1-(1-bromoprop-1-en-2-yl)-2-fluorobenzene (2.3 g, 23.3 mmol), 4,4,4',4',5,5,5',5'-octamethyl-2,2'-bi(1,3,2-dioxaborolane) (3.54 g, 13.95 mmol), Pd(dppf)Cl₂ (0.85 g, 1.16 mmol) and potassium acetate (2.28 g, 23.3 mmol) in dioxane (30 mL) was stirred at 70° C. for 12 h. The mixture was added H₂O and extracted with EtOAc. The combined extracts were washed with brine, dried over Na₂SO₄, concentrated to afford the title compound. $^1$H NMR (400 MHz, CDCl3): δ 7.31-7.15 (m, 2 H), 7.11-6.95 (m, 2 H), 5.66-5.50 (m, 1 H), 2.42-2.14 (m, 3 H), 1.36-1.24 (m, 6 H), 1.09 (s, 6 H).

Step 3: (E)-3-(2-(2-fluorophenyl)prop-1-en-1-yl) pyrazine-2-carbonitrile

A solution of (E)-2-(2-(2-fluorophenyl)prop-1-en-1-yl)-4,4,5,5-tetramethyl-1,3,2-dioxaborolane (100 mg, 0.38 mmol), 3-bromopyrazine-2-carbonitrile (70 mg, 0.381 mmol), Pd(dppf)Cl₂ (27.9 mg, 0.038 mmol) and K₂CO₃ (0.57 mL, 1.14 mmol) in dioxane (8 mL) was stirred at 70° C. for 12 h. After cooled to 25° C., the mixture was filtered, extracted with EtOAc. The combined extracts were washed with water and brine, dried over Na₂SO₄, concentrated and purified by silica column to afford the title compound. LCMS m/z=240 (M+1). $^1$H NMR (400 MHz, CDCl3): δ 8.78 (d, J=1.6 Hz, 1 H), 8.50 (s, 1 H), 7.46-7.30 (m, 2 H), 7.23-7.16 (m, 1 H), 7.16-7.07 (m, 1 H), 6.99 (s, 1 H), 2.61 (s, 3 H).

Step 4: (E)-3-(2-(2-fluorophenyl)prop-1-en-1-yl) pyrazine-2-carboximidamide

To a solution of NH₄Cl (1.4 g, 26.9 mmol) in toluene (3 mL) was added AlMe₃ (13.5 ml, 27 mmol) at 0° C. under N₂. The mixture was stirred at 25° C. for 1 h, then (E)-3-(2-(2-fluorophenyl)prop-1-en-1-yl)pyrazine-2-carbonitrile (180 mg, 0.75 mmol) in toluene (2 mL) was added, stirred at 100° C. for 18 h. After cooled to 0° C., the mixture was quenched with potassium sodium tartrate tetrahydrate (10.1 g) and 2M NaOH (15.4 ml), stirred at 25° C. for 1 h, then The mixture was extracted with EtOAc. The combined extracts were washed with water and brine, dried over Na₂SO₄, concentrated and purified by silica column (DCM:MeOH=20:1) to afford the title compound. $^1$H NMR (400 MHz, CDCl3): δ 8.80 (d, J=1.6 Hz, 1 H), 8.52 (s, 1 H), 7.41 (t, J=7.2 Hz, 1 H), 7.36-7.28 (m, 1 H), 7.22-7.08 (m, 2 H), 6.99-6.91 (m, 1 H), 2.37 (s, 3 H).

Step 5: 7-(2-fluoro-5-nitrophenyl)-7-methyl-7,8-dihydropyrido[3,4-b]pyrazin-5(6H)-imine A solution of (E)-3-(2-(2-fluorophenyl)prop-1-en-1-yl) pyrazine-2-carboximidamide (110 mg, 0.43 mmol) in conc. H₂SO₄ (11 mL) was stirred at 25° C. for 12 h. Then conc. HNO₃ (33 mg, 0.52 mmol) was added, the mixture was stirred at 25° C. for 1 h, quenched with aqueous solution of Na₂CO₃, extracted with EtOAc. The combined extracts were washed with water and brine, dried over Na₂SO₄, concentrated and purified by p-TLC and prep-HPLC (MeCN/water with 0.1% TFA modifier) to afford the title compound as the TFA salts. LCMS m/z=302 (M+1). $^1$H NMR (400 MHz, CD₃OD): δ8.83 (br. s., 1 H), 8.70 (br. s., 1 H), 8.30-8.22 (m, 1 H), 8.19 (dd, J=2.5, 6.8 Hz, 1 H), 7.44 (dd, J=9.2, 11.2 Hz, 1 H), 4.05 (d, J=17.2 Hz, 1 H), 3.81 (d, J=17.2 Hz, 1 H), 1.99 (s, 3 H).

Step 6: (Z)-tert-butyl (7-(2-fluoro-5-nitrophenyl)-7-methyl-7,8-dihydropyrido[3,4-b]pyrazin-5(6H)-ylidene)carbamate A mixture of 7-(2-fluoro-5-nitrophenyl)-7-methyl-7,8-dihydropyrido[3,4-b]pyrazin-5(6H)-imine (900 mg, 3.0 mmol), TEA (0.83 mL, 6.0 mmol), and Boc₂O (0.83 ml, 3.6 mmol) in DCM (10 mL) was stirred at 25° C. for 12 h. Then concentrated and purified by column (PE:EtOAc=3:1) to afford the title compound. LCMS m/z=402 (M+1). $^1$H NMR (400 MHz, CDCl3): δ 9.11 (d, J=4.0 Hz, 1 H), 8.67-8.55 (m, 1 H), 8.48 (br. s., 1 H), 8.20-8.08 (m, 1 H), 7.20 (t, J=9.8 Hz, 1 H), 3.79 (d, J=16.3 Hz, 1 H), 3.36 (d, J=16.6 Hz, 1 H), 1.66-1.54 (m, 12 H).

Step 7: (Z)-tert-butyl (7-(5-amino-2-fluorophenyl)-7-methyl-7,8-dihydropyrazin[3,4-b]pyrazin-5(6H)-ylidene)carbamate A mixture of (Z)-tert-butyl (7-(2-fluoro-5-nitrophenyl)-7-methyl-7,8-dihydropyrido[3,4-b]pyrazin-5(6H)-ylidene)

carbamate (200 mg, 0.50 mmol), NH₄Cl (133 mg, 2.49 mmol) and Fe powder (139 mg, 2.49 mmol) in MeOH (3 mL) and water (1 mL) was stirred at 70° C. for 1.5 h. The filtrate was extracted with EtOAc, washed with water and brine, dried over Na₂SO₄, concentrated and purified by preparative TLC (DCM:MeOH=20:1) to afford the title compound. LCMS m/z=372 (M+1). ¹H NMR (400 MHz, CDCl3): δ 9.04 (br. s., 1 H), 8.72-8.43 (m, 1 H), 6.97-6.73 (m, 1 H), 6.61-6.25 (m, 2 H), 4.07 (d, J=17.6 Hz, 1 H), 3.59 (d, J=17.6 Hz, 1 H), 2.04-1.93 (m, 3 H), 1.70-1.32 (m, 9 H).

Method G

Synthesis of (S)-tert-butyl(7-(5-amino-2-fluorophenyl)-7-methyl-7,8-dihydropyrido [4,3-d]pyrimidin-5(6H)-ylidene)carbamate (G2)

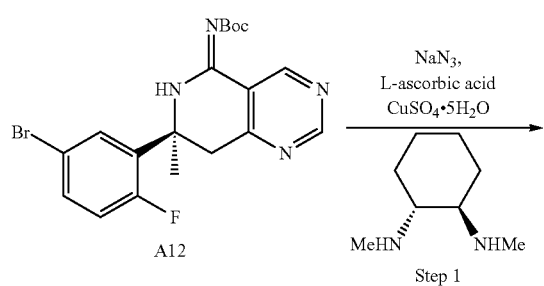

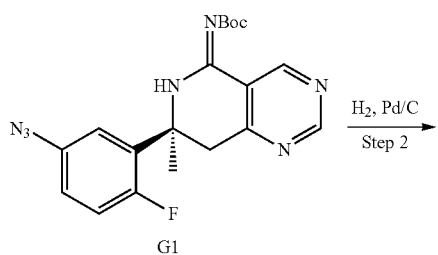

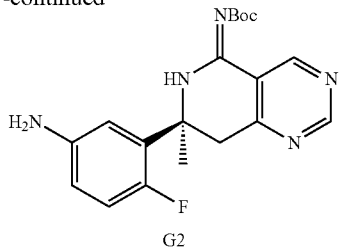

Step 1: (S)-tert-butyl (7-(5-azido-2-fluorophenyl)-7-methyl-7,8-dihydropyrido[4,3-d]pyrimidin-5(6H)-ylidene)carbamate A 0.66 M solution of L-ascorbic acid was prepared by dissolving L-ascorbic acid sodium salt (0.79 g, 2.0 mmol) in water (6 mL). To a solution of (S)-tert-butyl (7-(5-bromo-2-fluorophenyl)-7-methyl-7,8-dihydropyrido[4,3-d]pyrimidin-5(6H)-ylidene)carbamate (370 mg, 0.85 mmol) in EtOH (4 mL) was added (1R,2R)-N¹,N²-dimethyl-cyclohexane-1,2-diamine (39 mg, 0.28 mmol), sodium azide (166 mg, 2.55 mmol), aqueous L-ascorbic acid sodium salt (0.6 mL, 0.66 M) and water (0.7 mL). The reaction flask was degassed and evacuated with nitrogen. Copper (II) sulfate penta-hydrate (47 mg, 0.2 mmol) was added and the mixture was stirred at 80° C. for 1 hour, cooled to room temperature. The solution was quenched with ice water, and extracted with EtOAc. The EtOAc layer was dried over Na₂SO₄ and concentrated to afford the title compound. LCMS m/z=398 (M+1).

Step 2: (S)-tert-butyl (7-(5-amino-2-fluorophenyl)-7-methyl-7,8-dihydropyrido[4,3-d]pyrimidin-5(6H)-ylidene)carbamate To a mixture of (S)-tert-butyl (7-(5-azido-2-fluorophenyl)-7-methyl-7,8-dihydro-pyrido[4,3-d]pyrimidin-5(6H)-ylidene)carbamate (200 mg, 0.5 mmol) in MeOH (10 mL) was added Pd/C (50 mg, 10%) and stirred at 20° C. under H₂ (45 psi) for 2 hours. The mixture was filtered. The filtrate was concentrated and purified by column (PE:EA=5:1) to afford the title compound. LCMS m/z=372 (M+1). ¹H NMR (400 MHz, CDCl₃): δ 10.50 (s, 1 H), 9.37 (s, 1H), 9.10 (s, 1 H), 6.82~6.77 (m, 1 H), 6.46~6.42 (m, 1 H), 6.34~6.32 (m, 1 H), 3.80 (d, J=16.8 Hz, 1 H), 3.32 (d, J=16.8 Hz, 1 H), 1.84 (s, 3 H), 1.58 (s, 9 H).

Following the methods described above, intermediates H to R were prepared.

| Intermediate | Structure | Method | ¹H NMR (400 MHz, CD₃OD) | LCMS m/z (M + 1) |
|---|---|---|---|---|
| H | 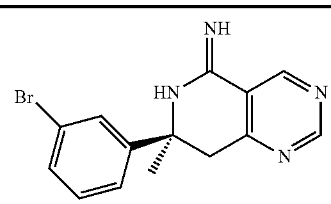 | A | δ 9.22 (s, 2 H), 8.74 (s, 1 H), 7.34-6.91 (m, 3 H), 3.80-3.70 (m, 2 H), 1.23-0.90 (m, 3 H). | 317 |
| I | 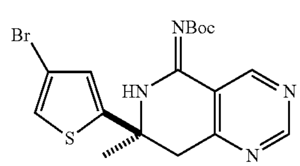 | A | Not recorded | 423 |

-continued

| Intermediate | Structure | Method | ¹H NMR (400 MHz, CD₃OD) | LCMS m/z (M + 1) |
|---|---|---|---|---|
| J | 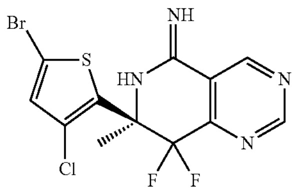 [SMILES: C[C@]1(c2sc(Br)cc2Cl)NC(=N)c2cncnc2C1(F)F] | C | δ 9.64 (s, 1 H), 9.58 (s, 1 H), 7.10 (s, 1 H), 1.99 (s, 3 H). | 393 |
| K | 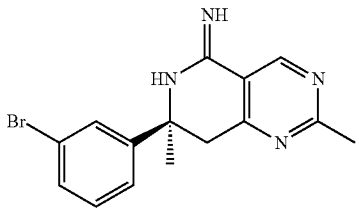 [SMILES: Cc1ncc2c(n1)C[C@@](C)(c1cccc(Br)c1)NC2=N] | B | δ 9.14 (s, 1 H), 7.59 (s, 1 H), 7.46-7.42 (m, 1 H), 7.38-7.36 (m, 1 H), 7.28-7.24 (m, 1 H), 3.75 (d, J = 16.8 Hz, 1 H), 3.59 (d, J = 16.8 Hz, 1 H), 2.74 (s, 3 H), 1.84 (s, 3 H). | 331 |
| L | 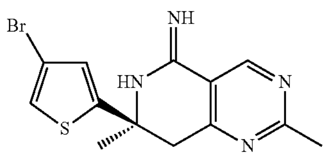 [SMILES: Cc1ncc2c(n1)C[C@@](C)(c1cc(Br)cs1)NC2=N] | B | δ 9.2 (s, 1 H), 7.3 (s, 1 H), 7.0 (s, 1 H), 3.6 (s, 2 H), 2.7 (s, 3 H), 1.9 (s, 3 H). | 337 |
| M | 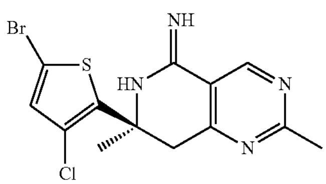 [SMILES: Cc1ncc2c(n1)C[C@@](C)(c1sc(Br)cc1Cl)NC2=N] | B | δ 9.16 (s, 1 H), 7.02 (s, 1 H), 3.92 (d, J = 17.2 Hz, 1 H), 3.56 (d, J = 17.2 Hz, 1 H), 2.75 (s, 3 H), 1.95 (s, 3 H). | 371 |
| N | 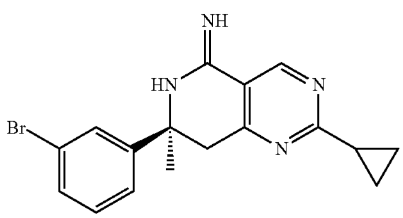 [SMILES: C[C@@]1(c2cccc(Br)c2)Cc2nc(C3CC3)ncc2C(=N)N1] | B | δ 9.03 (s, 1 H), 7.58 (s, 1 H), 7.45-7.43 (m, 1 H), 7.38-7.36 (m, 1 H), 7.30-7.25 (m, 1 H), 3.70 (d, J = 16.8 Hz, 1 H), 3.52 (d, J = 16.8 Hz, 1 H), 3.32-3.27 (m, 1 H), 1.82 (s, 3 H), 1.25-1.21 (m, 4 H). | 357 |
| O | 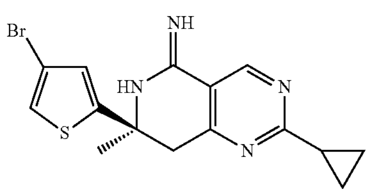 [SMILES: C[C@@]1(c2cc(Br)cs2)Cc2nc(C3CC3)ncc2C(=N)N1] | B | δ 9.05 (s, 1 H), 7.30 (s, 1 H), 6.97 (s, 1 H), 3.56 (s, 2 H), 2.49 (s, 3 H), 2.33-2.27 (m, 1 H), 1.87 (s, 3 H), 1.22-1.21 (m, 4 H). | 363 |
| P | 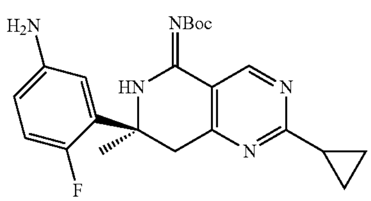 | D | Not recorded. | 412 |
| Q | 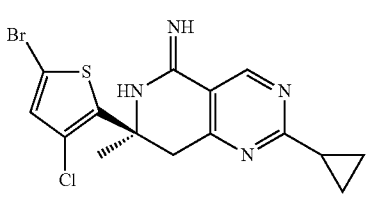 [SMILES: C[C@@]1(c2sc(Br)cc2Cl)Cc2nc(C3CC3)ncc2C(=N)N1] | B | δ 9.05 (s, 1 H), 7.01 (s, 1 H), 3.84-3.88 (m, 1 H), 3.48-3.52 (m, 1 H), 2.30-2.33 (m, 1 H), 1.92 (s, 3 H), 1.22-1.24 (m, 4 H). | 397 |

-continued

| Intermediate Structure | Method | $^1$H NMR (400 MHz, CD$_3$OD) | LCMS m/z (M + 1) |
|---|---|---|---|
| 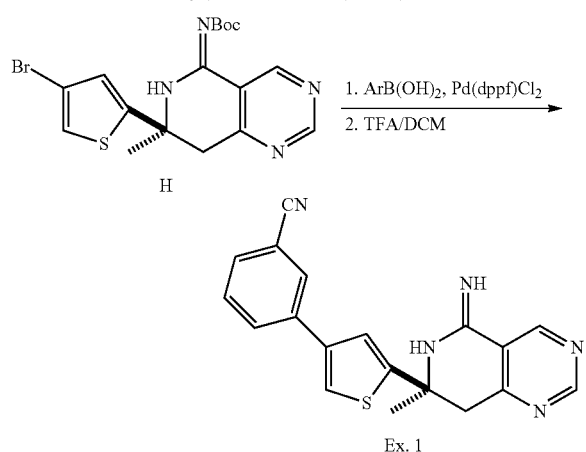 | B | δ 9.46 (s, 1 H), 7.34 (s, 1 H), 7.05 (s, 1 H), 3.84 (d, J = 17.2 Hz, 1 H), 3.76 (d, J = 17.2 Hz, 1 H), 1.92 (s, 3 H). | 391 |

Method AA

Synthesis of (S)-3-(5-(5-imino-7-methyl-5,6,7,8-tetrahydropyrido[4,3-d]pyrimidin-7-yl)thiophen-3-yl)benzonitrile (Ex. 1)

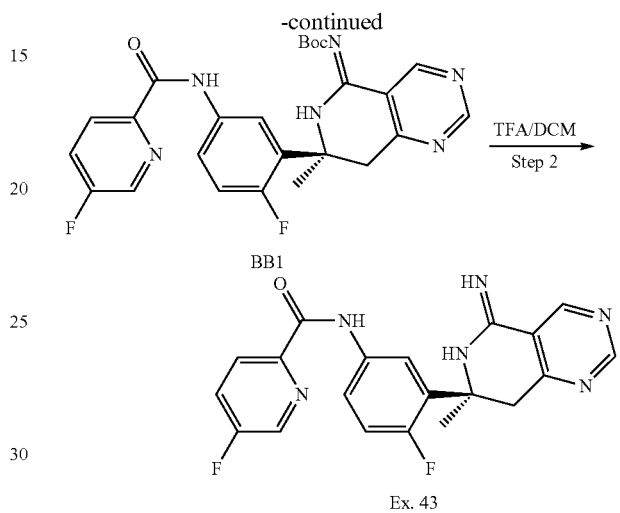

To a mixture of (S)-tert-butyl (7-(4-bromothiophen-2-yl)-7-methyl-7,8-dihydropyrido[4,3-d]pyrimidin-5(6H)-ylidene)carbamate (60 mg, 0.19 mmol), (3-cyanophenyl)boronic acid (41 mg, 0.28 mmol) and K$_2$CO$_3$ (40 mg, 0.28 mmol) in DMF (2 mL) and H$_2$O (0.5 mL) was added Pd(dppf)Cl$_2$ (31 mg, 0.038 mmol) at 25° C. The mixture was stirred at 100° C. for 1 h. The mixture was diluted with water, extracted with EtOAc. The combined extracts were washed with brine, dried over Na$_2$SO$_4$ and concentrated. The residue in TFA/DCM (20 mL, 1:10) stirred for 2 h, and then concentrated, purified by p-HPLC (ACN/water with 0.1% TFA modifier) to afford the title compound as the TFA salt. m/z=346 (M+1). $^1$H NMR (400 MHz, CD$_3$OD): δ 9.29 (s, 1 H), 9.26 (s, 1 H), 7.94 (s, 1 H), 7.86 (d, J=8.0 Hz, 1 H), 7.66 (s, 1H), 7.61 (d, J=8.0 Hz, 1 H), 7.53 (d, J=8.0 Hz, 1 H), 7.45 (s, 1 H), 3.68-3.82 (m, 2 H), 1.90 (s, 3 H).

Method BB

Synthesis of (S)-5-fluoro-N-(4-fluoro-3-(5-imino-7-methyl-5,6,7,8-tetrahydropyrido[4,3-d]pyrimidin-7-yl)phenyl)picolinamide (Ex. 43)

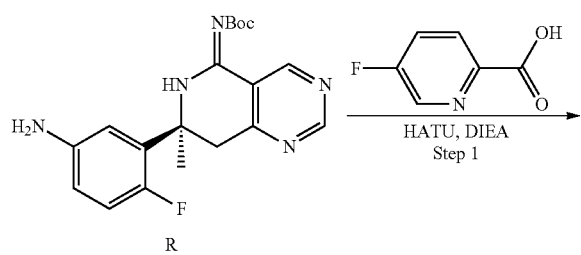

Step 1: (S)-tert-butyl (7-(2-fluoro-5-(5-fluoropicolinamido)phenyl)-7-methyl-7,8-dihydropyrido[4,3-d]pyrimidin-5(6H)-ylidene)carbamate A mixture of (S)-tert-butyl (7-(5-amino-2-fluorophenyl)-7-methyl-7,8-dihydropyrido[4,3-d]pyrimidin-5(6H)-ylidene)carbamate (150 mg, 0.4 mmol), 5-Fluoro-pyridine-2-carboxylic acid (68 mg, 0.485 mmol), HATU (442 mg, 1.164 mmol) and DIEA (300 mg, 2.328 mmol) in DMF (5 mL) was stirred at 20° C. under N$_2$ for 2 hours. The mixture was quenched with water and extracted with EtOAc. The EtOAc layer was dried over Na$_2$SO$_4$ and concentrated. The residue was purified by silica column (PE:EtOAc=3:1) to afford the title compound. m/z=495 (M+1).

Step 2: (S)-5-fluoro-N-(4-fluoro-3-(5-imino-7-methyl-5,6,7,8-tetrahydropyrido[4,3-d]pyrimidin-7-yl)phenyl)picolinamide To a solution of (S)-tert-butyl (7-(2-fluoro-5-(5-fluoropicolinamido)phenyl)-7-methyl-7,8-dihydropyrido[4,3-d]pyrimidin-5(6H)-ylidene)carbamate (170 mg, 0.34 mmol) in DCM (2 mL) was added TFA (0.5 mL) at 0° C., and then the mixture was stirred at 20° C. for 1 h. The mixture was concentrated and purified by p-HPLC (ACN/water with 0.1% TFA modifier) to afford the title compound as the TFA salt. m/z=395 (M+1). $^1$H NMR (400 MHz, CD$_3$OD): δ 9.23 (s, 2 H), 8.56 (s, 1 H), 8.25-8.21 (m, 1 H), 7.87-7.76 (m, 2 H), 7.62-7.59 (m, 1 H), 7.18-7.12 (m, 1 H), 3.90 (d, J=17.2 Hz, 1 H), 3.66 (d, J=17.2 Hz, 1 H), 1.96 (s, 3 H).

In another embodiment, the compounds of the invention comprise the example compounds shown in the table below, or a tautomer thereof, or a pharmaceutically acceptable salt of said compound or said tautomer. Examples 2 to 42 were prepared using the method similar to Ex. 1. Example 44 to 51 were synthesized using the method similar to Ex. 43.

BACE-1 values reported in this table were measured using BACE-1 Ki Assay (BACE-1 HTRF FRET Assay).

TABLE 1

| Ex | Structure<br>IUPAC Name | m/z | BACE-1<br>$K_i$ (nM) | BACE-2<br>$K_i$ (nM) |
|---|---|---|---|---|
| 1 | 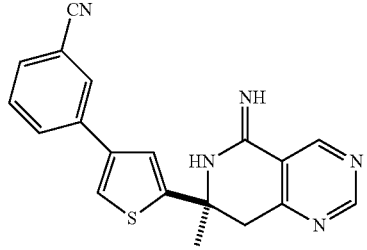 [SMILES: C[C@@]1(c2cc(-c3cccc(C#N)c3)cs2)Cc2ncncc2C(=N)N1]<br>3-{5-[(7S)-5-imino-7-methyl-5,6,7,8-tetrahydro-pyrido[4,3-d]pyrimidin-7-yl]thiophen-3-yl}benzonitrile | 346 | * | * |
| 2 | 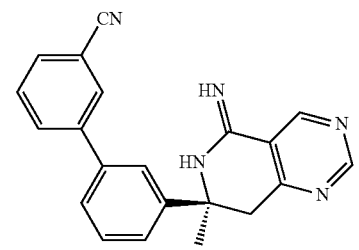<br>3'-[(7S)-5-imino-7-methyl-5,6,7,8-tetrahydro-pyrido[4,3-d]pyrimidin-7-yl]biphenyl-3-carbonitrile | 340 | * | * |
| 3 | 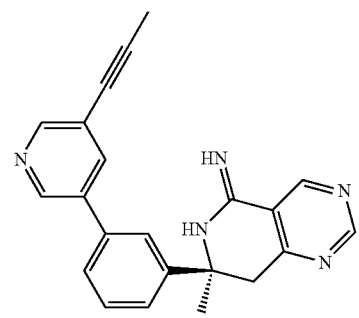 [SMILES: CC#Cc1cncc(-c2cccc([C@]3(C)Cc4ncncc4C(=N)N3)c2)c1]<br>(7S)-7-methyl-7-[3-(5-prop-1-yn-1-ylpyridin-3-yl)phenyl]-7,8-dihydro-pyrido[4,3-d]pyrimidin-5(6H)-imine | 354 | * | * |
| 4 | 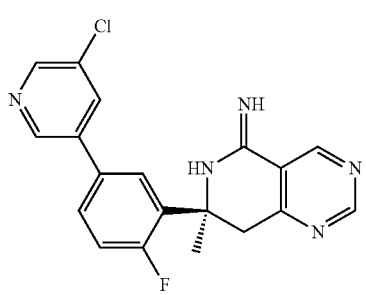<br>(7S)-7-[5-(5-chloropyridin-3-yl)-2-fluoro-phenyl]-7-methyl-7,8-dihydropyrido[4,3-d]pyrimidin-5(6H)-imine | 368 | 253.3 | 129.5 |

TABLE 1-continued

| Ex | Structure / IUPAC Name | m/z | BACE-1 K$_i$ (nM) | BACE-2 K$_i$ (nM) |
|---|---|---|---|---|
| 5 | (7S)-7-(4-fluoro-3'-methoxybiphenyl-3-yl)-7-methyl-7,8-dihydro-pyrido[4,3-d]pyrimidin-5(6H)-imine | 363 | 198.9 | 53.5 |
| 6 | (7S)-7-[4-fluoro-3'-(trifluoromethyl)biphenyl-3-yl]-7-methyl-7,8-dihydropyrido[4,3-d]pyrimidin-5(6H)-imine | 401 | 3036 | 549.3 |
| 7 | (7S)-7-(2-fluoro-5-pyrimidin-5-ylphenyl)-7-methyl-7,8-dihydro-pyrido[4,3-d]pyrimidin-5(6H)-imine | 335 | 770.8 | 3455 |
| 8 | (7S)-7-[2-fluoro-5-(5-methoxypyridin-3-yl)phenyl]-7-methyl-7,8-dihydropyrido[4,3-d]pyrimidin-5(6H)-imine | 364 | 224.8 | 87.8 |

TABLE 1-continued

| Ex | Structure IUPAC Name | m/z | BACE-1 $K_i$ (nM) | BACE-2 $K_i$ (nM) |
|---|---|---|---|---|
| 9 | 5-{4-fluoro-3-[(7S)-5-imino-7-methyl-5,6,7,8-tetrahydropyrido[4,3-d]pyrimidin-7-yl]phenyl}pyridine-3-carbonitrile | 359 | 600.6 | 483.0 |
| 10 | (7S)-7-(2-fluoro-5-pyridin-3-ylphenyl)-7-methyl-7,8-dihydropyrido[4,3-d]pyrimidin-5(6H)-imine | 334 | 746.2 | 1177 |
| 11 | 4'-fluoro-3'-[(7S)-5-imino-7-methyl-5,6,7,8-tetrahydropyrido[4,3-d]pyrimidin-7-yl]biphenyl-3-carbonitrile | 358 | 827.3 | 259.0 |
| 12 | (7S)-7-[2-fluoro-5-(5-prop-1-yn-1-ylpyridin-3-yl)phenyl]-7-methyl-7,8-dihydropyrido[4,3-d]pyrimidin-5(6H)-imine | 372 | 108.5 | 20.2 |

TABLE 1-continued

| Ex | Structure IUPAC Name | m/z | BACE-1 K$_i$ (nM) | BACE-2 K$_i$ (nM) |
|---|---|---|---|---|
| 13 | 3-{4-chloro-5-[(7S)-5-imino-7-methyl-5,6,7,8-tetrahydropyrido[4,3-d]pyrimidin-7-yl]thiophen-2-yl}benzonitrile | 380 | 35.2 | 15.1 |
| 14 | 5-{4-chloro-5-[(7S)-5-imino-7-methyl-5,6,7,8-tetrahydropyrido[4,3-d]pyrimidin-7-yl]thiophen-2-yl}pyridine-3-carbonitrile | 381 | 75.2 | 31.6 |
| 15 | (7S)-7-{3-chloro-5-[3-(1,3,4-oxadiazol-2-yl)phenyl]thiophen-2-yl}-7-methyl-7,8-dihydropyrido[4,3-d]pyrimidin-5(6H)-imine | 423 | 11.1 | 37.3 |
| 16 | 5-{4-chloro-5-[(7S)-5-imino-7-methyl-5,6,7,8-tetrahydropyrido[4,3-d]pyrimidin-7-yl]thiophen-2-yl}-2-fluorobenzonitrile | 398 | 36.4 | 16.7 |

TABLE 1-continued

| Ex | Structure IUPAC Name | m/z | BACE-1 K$_i$ (nM) | BACE-2 K$_i$ (nM) |
|---|---|---|---|---|
| 17 | (7S)-7-{3-chloro-5-[3-fluoro-5-(1,3,4-oxadiazol-2-yl)phenyl]thiophen-2-yl}-7-methyl-7,8-dihydropyrido[4,3-d]pyrimidin-5(6H)-imine | 441 | 16.5 | 21.6 |
| 18 | 3-{5-[(7S)-8,8-difluoro-5-imino-7-methyl-5,6,7,8-tetrahydropyrido[4,3-d]pyrimidin-7-yl]thiophen-3-yl}benzonitrile | 382 | 81.5 | 39.8 |
| 19 | 3-{4-chloro-5-[(7S)-8,8-difluoro-5-imino-7-methyl-5,6,7,8-tetrahydropyrido[4,3-d]pyrimidin-7-yl]thiophen-2-yl}benzonitrile | 416 | 245.7 | 128 |
| 20 | (7S)-7-{3-chloro-5-[3-(1,3,4-oxadiazol-2-yl)phenyl]thiophen-2-yl}-8,8-difluoro-7-methyl-7,8-dihydropyrido[4,3-d]pyrimidin-5(6H)-imine | 459 | 33.3 | 118.2 |

TABLE 1-continued

| Ex | Structure IUPAC Name | m/z | BACE-1 $K_i$ (nM) | BACE-2 $K_i$ (nM) |
|----|----------------------|-----|-------------------|-------------------|
| 21 | 3'-[(7S)-5-imino-2,7-dimethyl-5,6,7,8-tetrahydropyrido[4,3-d]pyrimidin-7-yl]biphenyl-3-carbonitrile | 354 | * | * |
| 22 | (7S)-2,7-dimethyl-7-[3-(5-prop-1-yn-1-ylpyridin-3-yl)phenyl]-7,8-dihydropyrido[4,3-d]pyrimidin-5(6H)-imine | 368 | * | * |
| 23 | 3-{5-[(7S)-5-imino-2,7-dimethyl-5,6,7,8-tetrahydropyrido[4,3-d]pyrimidin-7-yl]thiophen-3-yl}benzonitrile | 360.0 | 150.7 | 87.9 |
| 24 | 3-{4-chloro-5-[(7S)-5-imino-2,7-dimethyl-5,6,7,8-tetrahydropyrido[4,3-d]pyrimidin-7-yl]thiophen-2-yl}benzonitrile | 394 | 52.7 | 28.0 |

TABLE 1-continued

| Ex | Structure IUPAC Name | m/z | BACE-1 $K_i$ (nM) | BACE-2 $K_i$ (nM) |
|---|---|---|---|---|
| 25 | 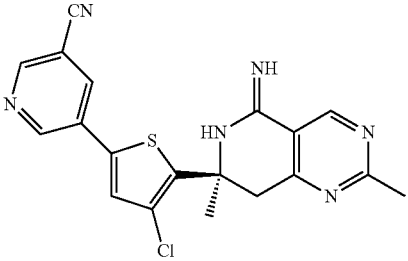 [SMILES: Cc1ncc2c(n1)C[C@@](C)(c1sc(-c3cncc(C#N)c3)cc1Cl)NC2=N]  5-{4-chloro-5-[(7S)-5-imino-2,7-dimethyl-5,6,7,8-tetrahydropyrido[4,3-d]pyrimidin-7-yl]thiophen-2-yl}pyridine-3-carbonitrile | 395 | 125.2 | 62.4 |
| 26 | 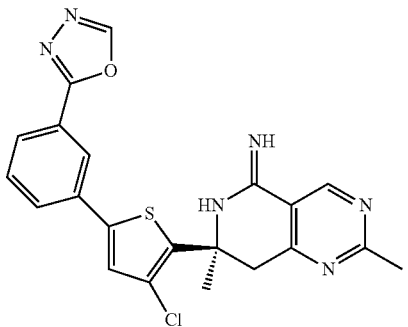 [SMILES: Cc1ncc2c(n1)C[C@@](C)(c1sc(-c3cccc(-c4nnco4)c3)cc1Cl)NC2=N]  (7S)-7-{3-chloro-5-[3-(1,3,4-oxadiazol-2-yl)phenyl]thiophen-2-yl}-2,7-dimethyl-7,8-dihydropyrido[4,3-d]pyrimidin-5(6H)-imine | 437 | 10.6 | 29.1 |
| 27 | 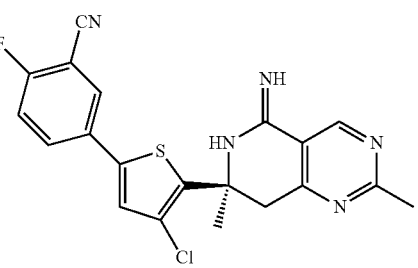  5-{4-chloro-5-[(7S)-5-imino-2,7-dimethyl-5,6,7,8-tetrahydropyrido[4,3-d]pyrimidin-7-yl]thiophen-2-yl}-2-fluorobenzonitrile | 412 | 52.1 | 28.3 |
| 28 | 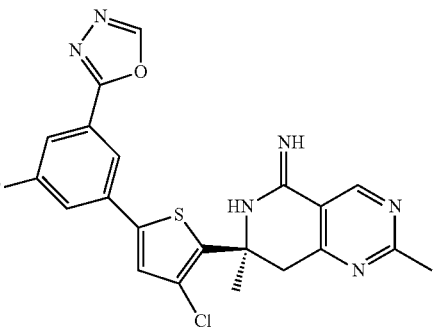  (7S)-7-{3-chloro-5-[3-fluoro-5-(1,3,4-oxadiazol-2-yl)phenyl]thiophen-2-yl}-2,7-dimethyl-7,8-dihydropyrido[4,3-d]pyrimidin-5(6H)-imine | 455 | 16.6 | 24.4 |

TABLE 1-continued

| Ex | Structure IUPAC Name | m/z | BACE-1 K$_i$ (nM) | BACE-2 K$_i$ (nM) |
|---|---|---|---|---|
| 29 | 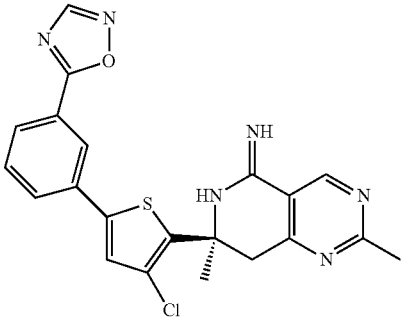 [SMILES: Cc1ncc2c(n1)C[C@@](C)(c1sc(-c3cccc(-c4ncno4)c3)cc1Cl)NC2=N]<br>(7S)-7-{3-chloro-5-[3-(1,2,4-oxadiazol-5-yl)phenyl]thiophen-2-yl}-2,7-dimethyl-7,8-dihydropyrido[4,3-d]pyrimidin-5(6H)-imine | 437 | 481.8 | 79.7 |
| 30 | 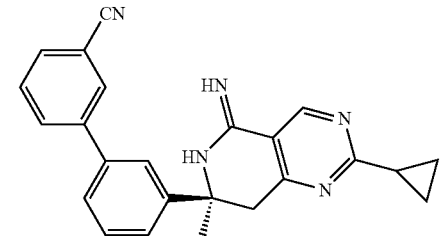<br>3'-[(7S)-2-cyclopropyl-5-imino-7-methyl-5,6,7,8-tetrahydropyrido[4,3-d]pyrimidin-7-yl]biphenyl-3-carbonitrile | 380 | * | * |
| 31 | 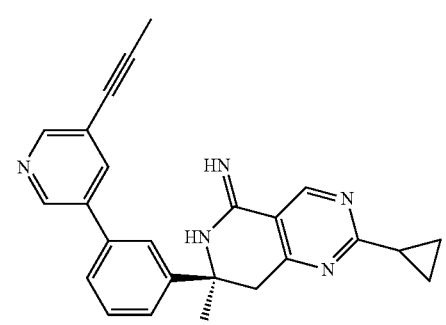<br>(7S)-2-cyclopropyl-7-methyl-7-[3-(5-prop-1-yn-1-ylpyridin-3-yl)phenyl]-7,8-dihydropyrido[4,3-d]pyrimidin-5(6H)-imine | 394 | * | * |
| 32 | 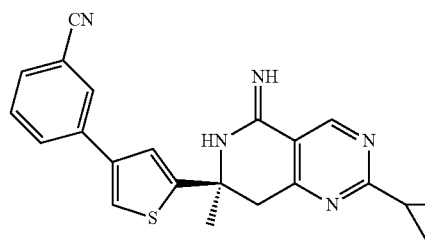<br>3-{5-[(7S)-2-cyclopropyl-5-imino-7-methyl-5,6,7,8-tetrahydropyrido[4,3-d]pyrimidin-7-yl]thiophen-3-yl}benzonitrile | 386 | 127.8 | 65.6 |

TABLE 1-continued

| Ex | Structure IUPAC Name | m/z | BACE-1 K_i (nM) | BACE-2 K_i (nM) |
|---|---|---|---|---|
| 33 | 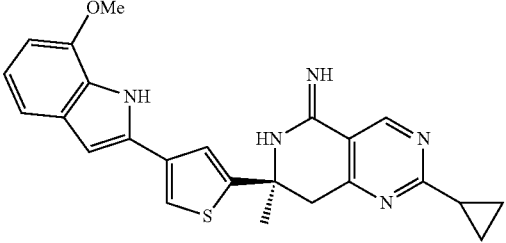 [SMILES: COc1cccc2cc(-c3csc([C@]4(C)Cc5nc(C6CC6)ncc5C(=N)N4)c3)[nH]c12] (7S)-2-cyclopropyl-7-[4-(7-methoxy-1H-indol-2-yl)thiophen-2-yl]-7-methyl-7,8-dihydropyrido[4,3-d]pyrimidin-5(6H)-imine | 430 | 38.2 | 4.8 |
| 34 | 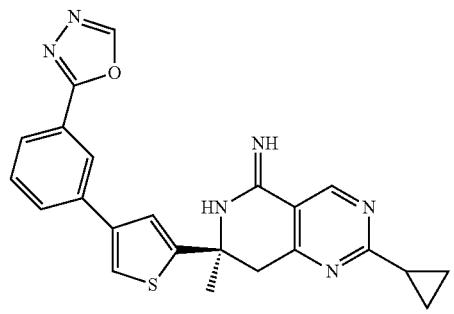 [SMILES: C[C@@]1(c2cc(-c3cccc(-c4nnco4)c3)cs2)Cc2nc(C3CC3)ncc2C(=N)N1] (7S)-2-cyclopropyl-7-methyl-7-{4-[3-(1,3,4-oxadiazol-2-yl)phenyl]thiophen-2-yl}-7,8-dihydropyrido[4,3-d]pyrimidin-5(6H)-imine | 429 | 85.0 | 214.9 |
| 35 | 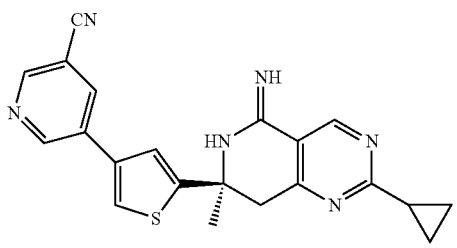 [SMILES: C[C@@]1(c2cc(-c3cncc(C#N)c3)cs2)Cc2nc(C3CC3)ncc2C(=N)N1] 5-{5-[(7S)-2-cyclopropyl-5-imino-7-methyl-5,6,7,8-tetrahydropyrido[4,3-d]pyrimidin-7-yl]thiophen-3-yl}pyridine-3-carbonitrile | 387 | 223.7 | 142.4 |
| 36 | 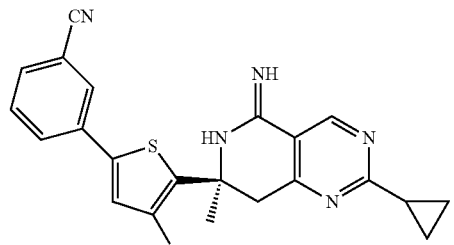 3-{4-chloro-5-[(7S)-2-cyclopropyl-5-imino-7-methyl-5,6,7,8-tetrahydropyrido[4,3-d]pyrimidin-7-yl]thiophen-2-yl}benzonitrile | 420 | 48.9 | 21.5 |

TABLE 1-continued

| Ex | Structure / IUPAC Name | m/z | BACE-1 $K_i$ (nM) | BACE-2 $K_i$ (nM) |
|---|---|---|---|---|
| 37 | 5-{4-chloro-5-[(7S)-2-cyclopropyl-5-imino-7-methyl-5,6,7,8-tetrahydropyrido[4,3-d]pyrimidin-7-yl]thiophen-2-yl}pyridine-3-carbonitrile | 421 | 94.7 | 44.2 |
| 38 | (7S)-7-[3-chloro-5-(7-methoxy-1H-indol-2-yl)thiophen-2-yl]-2-cyclopropyl-7-methyl-7,8-dihydropyrido[4,3-d]pyrimidin-5(6H)-imine | 464 | 22.3 | 2.0 |
| 39 | (7S)-7-[4-(7-methoxy-1H-indol-2-yl)thiophen-2-yl]-7-methyl-2-(trifluoromethyl)-7,8-dihydropyrido[4,3-d]pyrimidin-5(6H)-imine | 458 | 28.9 | 1.5 |
| 40 | 3-{5-[(7S)-5-imino-7-methyl-2-(trifluoromethyl)-5,6,7,8-tetrahydropyrido[4,3-d]pyrimidin-7-yl]thiophen-3-yl}benzonitrile | 414 | 58.2 | 23.1 |

TABLE 1-continued

| Ex | Structure IUPAC Name | m/z | BACE-1 K$_i$ (nM) | BACE-2 K$_i$ (nM) |
|---|---|---|---|---|
| 41 | 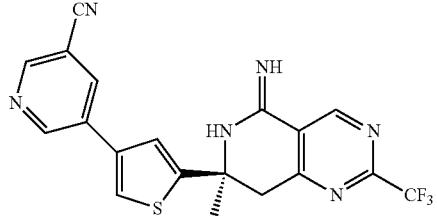 [SMILES: C[C@@]1(c2cc(-c3cncc(C#N)c3)cs2)Cc2nc(C(F)(F)F)ncc2C(=N)N1]<br>5-{5-[(7S)-5-imino-7-methyl-2-(trifluoromethyl)-5,6,7,8-tetrahydropyrido[4,3-d]pyrimidin-7-yl]thiophen-3-yl}pyridine-3-carbonitrile | 415 | 207.6 | 97.7 |
| 42 | 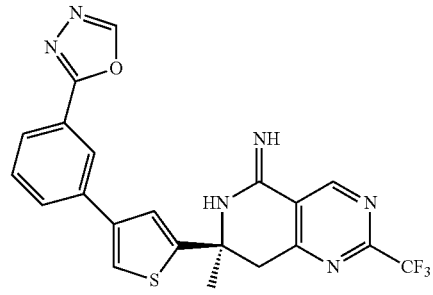 [SMILES: C[C@@]1(c2cc(-c3cccc(-c4nnco4)c3)cs2)Cc2nc(C(F)(F)F)ncc2C(=N)N1]<br>(7S)-7-methyl-7-{4-[3-(1,3,4-oxadiazol-2-yl)phenyl]thiophen-2-yl}-2-(trifluoromethyl)-7,8-dihydropyrido[4,3-d]pyrimidin-5(6H)-imine | 457 | 49.6 | 121 |
| 43 | 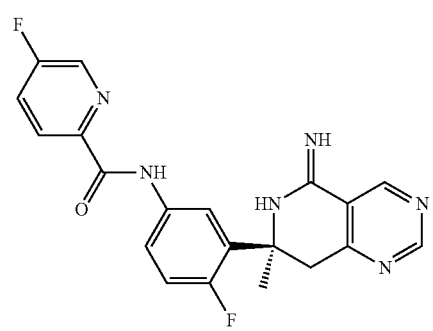 [SMILES: C[C@@]1(c2cc(NC(=O)c3ccc(F)cn3)ccc2F)Cc2ncncc2C(=N)N1]<br>5-fluoro-N-{4-fluoro-3-[(7S)-5-imino-7-methyl-5,6,7,8-tetrahydropyrido[4,3-d]pyrimidin-7-yl]phenyl}pyridine-2-carboxamide | 395 | 9.4 | 3.0 |
| 44 | 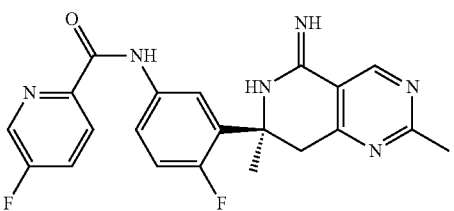<br>5-fluoro-N-{4-fluoro-3-[(7S)-5-imino-2,7-dimethyl-5,6,7,8-tetrahydropyrido[4,3-d]pyrimidin-7-yl]phenyl}pyridine-2-carboxamide | 409 | 16.8 | 4.5 |

TABLE 1-continued

| Ex | Structure IUPAC Name | m/z | BACE-1 $K_i$ (nM) | BACE-2 $K_i$ (nM) |
|---|---|---|---|---|
| 45 | 5-chloro-N-{4-fluoro-3-[(7S)-5-imino-2,7-dimethyl-5,6,7,8-tetrahydropyrido[4,3-d]pyrimidin-7-yl]phenyl}pyridine-2-carboxamide | 425 | 10.4 | 4.2 |
| 46 | N-{4-fluoro-3-[(7S)-5-imino-2,7-dimethyl-5,6,7,8-tetrahydropyrido[4,3-d]pyrimidin-7-yl]phenyl}-5-(trifluoromethyl)pyridine-2-carboxamide | 459 | 18.1 | 48.3 |
| 47 | N-{4-fluoro-3-[(7S)-5-imino-2,7-dimethyl-5,6,7,8-tetrahydropyrido[4,3-d]pyrimidin-7-yl]phenyl}-5-methoxypyridine-2-carboxamide | 421 | 15.4 | 15.3 |
| 48 | N-{3-[(7S)-2-cyclopropyl-5-imino-7-methyl-5,6,7,8-tetrahydropyrido[4,3-d]pyrimidin-7-yl]-4-fluorophenyl}-5-fluoropyridine-2-carboxamide | 435 | 13.1 | 3.0 |
| 49 | N-{3-[(7S)-2-cyclopropyl-5-imino-7-methyl-5,6,7,8-tetrahydropyrido[4,3-d]pyrimidin-7-yl]-4-fluorophenyl}-5-(trifluoromethyl)pyridine-2-carboxamide | 485 | 20.5 | 34.2 |

TABLE 1-continued

| Ex | Structure IUPAC Name | m/z | BACE-1 $K_i$ (nM) | BACE-2 $K_i$ (nM) |
|---|---|---|---|---|
| 50 | 5-cyano-N-{3-[(7S)-7-(difluoromethyl)-5-imino-2-methyl-5,6,7,8-tetrahydropyrido[4,3-d]pyrimidin-7-yl]-4-fluorophenyl}pyridine-2-carboxamide | 452 | 7.1 | 10.9 |
| 51 | 5-cyano-N-{4-fluoro-3-[(7S)-5-imino-7-methyl-5,6,7,8-tetrahydropyrido[3,4-b]pyrazin-7-yl]phenyl}pyridine-2-carboxamide | 402 | 62.7 | 207.2 |

Table 2 below contains measured $^1$H NMR data for each of Examples 1 to 51 of the compounds of the invention.

TABLE 2

| Ex. | Structure | $^1$H NMR (400 MHz, CD$_3$OD) |
|---|---|---|
| 1 | 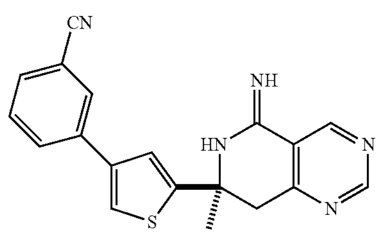 | δ 9.29 (s, 1 H), 9.26 (s, 1 H), 7.94 (s, 1 H), 7.86 (d, J = 8.0 Hz, 1 H), 7.66 (s, 1 H), 7.61 (d, J = 8.0 Hz, 1 H), 7.53 (d, J = 8.0 Hz, 1 H), 7.45 (s, 1 H), 3.68-3.82 (m, 2 H), 1.90 (s, 3 H). |
| 2 | 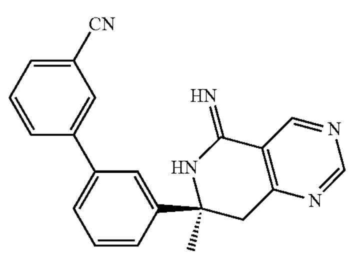 [SMILES: C[C@@]1(c2cccc(-c3cccc(C#N)c3)c2)Cc2ncncc2C(=N)N1] | δ 9.12 (s, 2 H), 8.64 (s, 2 H), 7.11-6.91 (m, 6 H), 3.80-3.72 (m, 2 H), 1.26-0.90(m, 3 H). |

TABLE 2-continued
| Ex. | Structure | ¹H NMR (400 MHz, CD₃OD) |
|---|---|---|
| 3 | 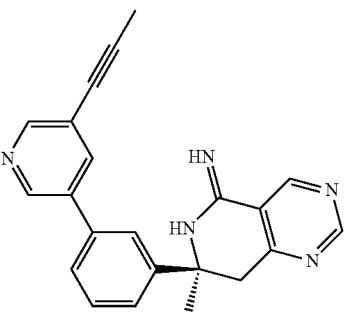 [SMILES: CC#Cc1cncc(-c2cccc([C@]3(C)Cc4ncncc4C(=N)N3)c2)c1] | δ 9.22 (s, 2 H), 8.84 (s, 2 H), 8.04 (s, 1 H), 7.34-6.91 (m, 2 H), 6.69-6.43 (m, 2 H), 3.80-3.70 (m, 2 H), 1.67-1.50 (m, 3 H), 1.23-0.90 (m, 3 H). |
| 4 | 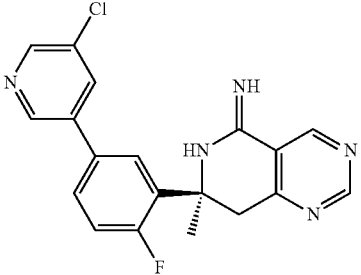 | δ 9.29 (s, 1 H), 9.21 (s, 1 H), 8.62-8.44 (m, 2 H), 8.01 (s, 1 H), 7.64 (s, 1 H), 7.47 (d, J = 7.6 Hz, 1 H), 7.30 (dd, J = 12.2, 8.5 Hz, 1 H), 4.06 (d, J = 17.2 Hz, 1 H), 3.68 (d, J = 17.3 Hz, 1 H), 1.96 (s, 3 H). |
| 5 | 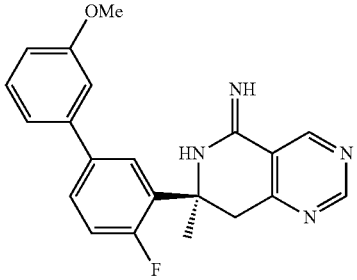 | δ 9.30 (s, 1 H), 9.21 (s, 1 H), 7.53 (s, 1 H), 7.32 (dd, J = 18.2, 9.1 Hz, 2 H), 7.21 (dd, J = 12.3, 8.5 Hz, 1 H), 6.98 (d, J = 7.4 Hz, 1 H), 6.91 (d, J = 8.6 Hz, 2 H), 4.03 (d, J = 17.2 Hz, 1 H), 3.82 (s, 3 H), 3.68 (d, J = 17.2 Hz, 1 H), 1.96 (s, 3 H). |
| 6 | 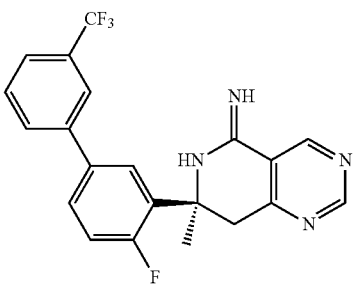 | δ 9.28 (s, 1 H), 9.21 (s, 1 H), 7.58-7.71 (m, 5 H), 7.23-7.43 (m, 2 H), 4.02 (d, J = 16.4 Hz, 1 H), 3.67 (d, J = 16.4 Hz, 1 H), 1.97 (s, 3 H). |
| 7 | 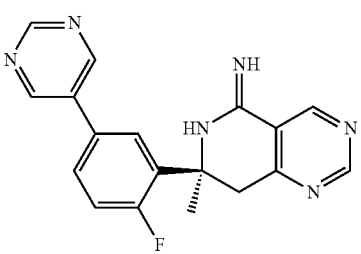 [SMILES: C[C@@]1(c2cc(-c3cncnc3)ccc2F)Cc2ncncc2C(=N)N1] | δ 9.27 (s, 1 H), 9.22 (s, 1 H), 9.11 (s, 1 H), 8.91 (s, 1 H), 7.65-7.69 (m, 2 H), 7.29-7.53 (m, 2 H), 4.07 (d, J = 16.4 Hz, 1 H), 3.67 (d, J = 16.4 Hz, 1 H), 1.97 (s, 3 H). |

TABLE 2-continued

| Ex. | Structure | ¹H NMR (400 MHz, CD₃OD) |
|---|---|---|
| 8 | 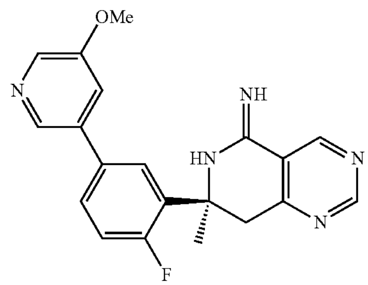 [SMILES: COc1cncc(-c2ccc(F)c([C@]3(C)Cc4ncncc4C(=N)N3)c2)c1] | δ 9.26 (s, 1 H), 9.22 (s, 1 H), 8.59 (s, 2 H), 8.17 (s, 1 H), 7.75-7.73 (m, 1 H), 7.62-7.60 (m, 1 H), 7.37-7.32 (m, 1 H), 4.07 (s, 3 H), 4.03 (d, J = 17.2 Hz, 1 H), 3.70 (d, J = 17.2 Hz, 1 H), 1.97 (s, 3 H). |
| 9 | 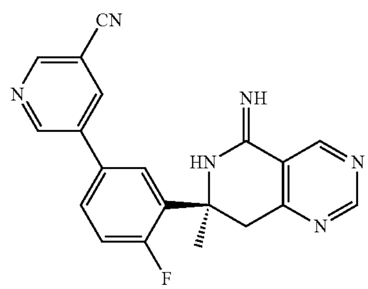 | δ 9.28 (s, 1 H), 9.22 (s, 1 H), 8.91-8.87 (m, 2 H), 8.34 (s, 1 H), 7.69-7.66 (m, 1 H), 7.53-7.51 (m, 1 H), 7.34-7.29 (m, 1 H), 4.06 (d, J = 17.2 Hz, 1 H), 3.69 (d, J = 17.2 Hz, 1H), 1.97 (s, 3 H). |
| 10 | 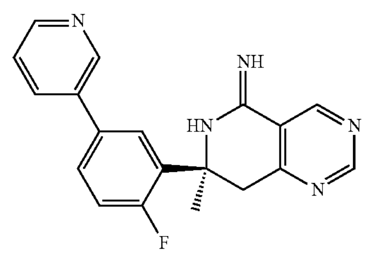 [SMILES: C[C@@]1(c2cc(-c3cccnc3)ccc2F)Cc2ncncc2C(=N)N1] | δ 9.26 (s, 1 H), 9.24 (s, 1 H), 9.01 (s, 1 H), 8.79 (d, J = 5.2 Hz, 1 H), 8.65 (d, J = 8.4 Hz, 1 H), 8.03-8.06 (m, 1 H), 7.73-7.77 (m, 1 H), 7.63-7.64 (m, 1 H), 7.33-7.39 (m, 1 H), 4.08 (d, J = 16.8 Hz, 1 H), 3.71 (d, J = 16.8 Hz, 1 H), 1.97 (s, 3 H). |
| 11 | 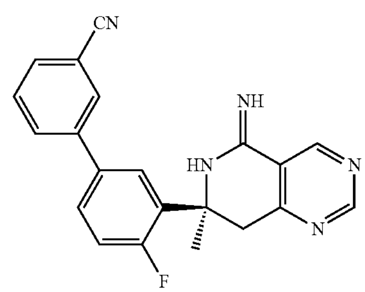 [SMILES: C[C@@]1(c2cc(-c3cccc(C#N)c3)ccc2F)Cc2ncncc2C(=N)N1] | δ 9.27 (s, 1 H), 9.23 (s, 1 H), 7.96 (s, 1 H), 7.82 (s, 1 H), 7.76 (d, J = 8 Hz, 1 H), 7.68 (d, J = 8 Hz, 1 H), 7.56-7.60 (m, 2 H), 7.44-7.46 (m, 1 H), 7.22-7.28 (m, 1 H), 4.04 (d, J = 17.6 Hz, 1 H), 3.69 (d, J = 17.6 Hz, 1 H), 1.97 (s, 3 H). |
| 12 | 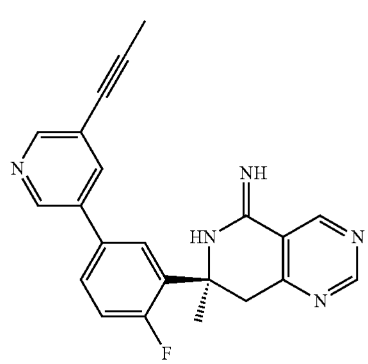 [SMILES: CC#Cc1cncc(-c2ccc(F)c([C@]3(C)Cc4ncncc4C(=N)N3)c2)c1] | δ 9.28 (s, 1 H), 9.22 (s, 1 H), 8.54 (brs, 2 H), 7.97 (s, 1 H), 7.60-7.63 (m, 1 H), 7.44-7.46 (m, 1 H), 7.26-7.31 (m, 1 H), 4.05 (d, J = 17.2 Hz, 1 H), 3.68 (d, J = 17.2 Hz, 1 H), 2.08 (s, 3 H), 1.96 (s, 3 H). |

TABLE 2-continued

| Ex. | Structure | $^1$H NMR (400 MHz, CD$_3$OD) |
|---|---|---|
| 13 | 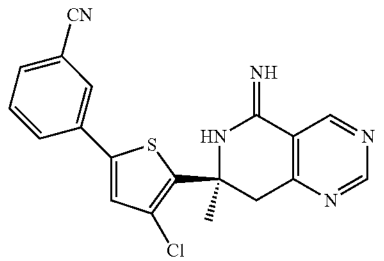 [SMILES: C[C@@]1(c2sc(-c3cccc(C#N)c3)cc2Cl)Cc2ncncc2C(=N)N1] | δ 9.30 (s, 2 H), 7.89 (s, 1 H), 7.80 (d, J = 8.0 Hz, 1 H), 7.66 (d, J = 8.0 Hz, 1 H), 7.55 (d, J = 8.0 Hz, 1 H), 7.39 (s, 1 H), 4.06-4.10 (m, 1H), 3.16-3.20 (m, 1 H), 2.03 (s, 3 H). |
| 14 | 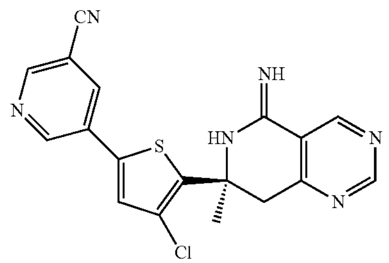 [SMILES: C[C@@]1(c2sc(-c3cncc(C#N)c3)cc2Cl)Cc2ncncc2C(=N)N1] | δ 9.30 (s, 2 H), 8.94 (s, 1 H), 8.80 (s, 1 H), 8.30 (s, 1 H), 7.51 (s, 1 H), 4.07-4.11 (m, 1 H), 3.67-3.71 (m, 1 H), 2.03 (s, 3 H). |
| 15 | 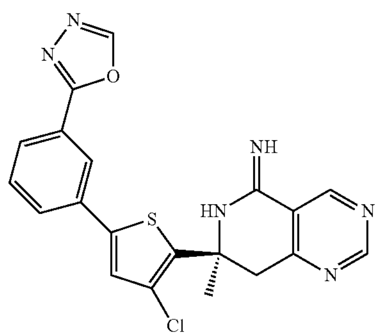 [SMILES: C[C@@]1(c2sc(-c3cccc(-c4nnco4)c3)cc2Cl)Cc2ncncc2C(=N)N1] | δ 9.30 (s, 2 H), 9.03 (s, 1 H), 8.16 (s, 1 H), 7.98 (d, J = 8.0 Hz, 1 H), 7.75 (d, J = 8.0 Hz, 1 H), 7.58 (t, J = 8.0 Hz, 1 H), 7.38 (s, 1 H), 4.08-4.12 (m, 1 H), 3.67-3.71 (m, 1 H), 2.03 (s, 3 H). |
| 16 | 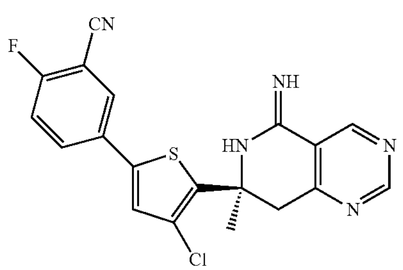 [SMILES: C[C@@]1(c2sc(-c3ccc(F)c(C#N)c3)cc2Cl)Cc2ncncc2C(=N)N1] | δ 9.30 (s, 2 H), 7.92-7.94 (m, 1 H), 7.81-7.85 (m, 1 H), 7.34-7.39 (m, 2 H), 4.05-4.09 (m, 1 H), 3.66-3.70 (m, 1 H), 2.02 (s, 3 H). |
| 17 | 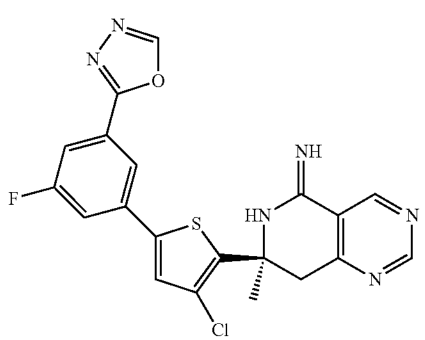 [SMILES: C[C@@]1(c2sc(-c3cc(F)cc(-c4nnco4)c3)cc2Cl)Cc2ncncc2C(=N)N1] | δ 9.31 (s, 2 H), 9.05 (s, 1 H), 7.98 (s, 1 H), 7.72 (d, J = 8.0 Hz, 1 H), 7.56 (d, J = 8.0 Hz, 1 H), 7.45 (s, 1 H), 4.08-4.12 (m, 1 H), 3.68-3.72 (m, 1 H), 2.04 (s, 3 H). |

TABLE 2-continued

| Ex. | Structure | ¹H NMR (400 MHz, CD₃OD) |
|---|---|---|
| 18 | 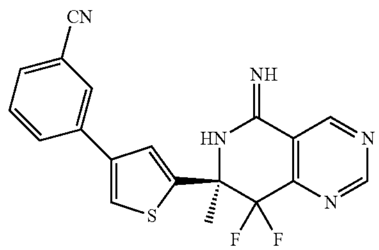 [SMILES: C[C@]1(c2cc(-c3cccc(C#N)c3)cs2)NC(=N)c2cncnc2C1(F)F] | δ 9.58-9.60 (m, 2 H), 7.97 (s, 1 H), 7.87-7.89 (m, 1 H), 7.81 (s, 1 H), 7.52-7.63 (m, 3 H), 2.07 (s, 3 H). |
| 19 | 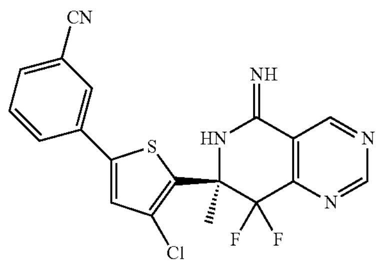 [SMILES: C[C@]1(c2sc(-c3cccc(C#N)c3)cc2Cl)NC(=N)c2cncnc2C1(F)F] | δ 9.61 (d, J = 8.4 Hz, 2 H), 7.93 (s, 1 H), 7.84 (d, J = 8 Hz, 1 H), 7.67 (d, J = 8 Hz, 1 H), 7.55 (t, J = 8 Hz, 1 H), 7.44 (s, 1 H), 2.08 (s, 3 H). |
| 20 | 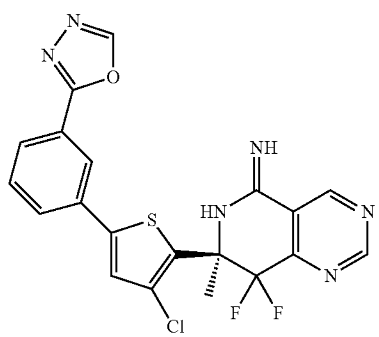 [SMILES: C[C@]1(c2sc(-c3cccc(-c4nnco4)c3)cc2Cl)NC(=N)c2cncnc2C1(F)F] | δ 9.41 (s, 1 H), 9.26 (s, 1 H), 9.04 (s, 1 H), 8.23 (s, 1 H), 7.99 (d, J = 7.6 Hz, 1 H), 7.81 (d, J = 7.2 Hz, 1 H), 7.59 (t, J = 8 Hz, 1 H), 7.37 (s, 1 H), 1.79 (s, 3 H). |
| 21 | 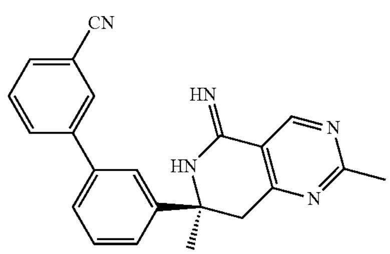 [SMILES: Cc1ncc2c(n1)C[C@@](C)(c1cccc(-c3cccc(C#N)c3)c1)NC2=N] | δ 9.03 (s, 1 H), 7.85 (s, 1 H), 7.81-7.79 (m, 1 H), 7.65-7.63 (m, 1 H), 7.58-7.52 (m, 2 H), 7.49-7.47 (m, 1 H), 7.40-7.33 (m, 2 H), 3.77 (d, J = 16.8 Hz, 1 H), 3.51 (d, J = 16.8 Hz, 1 H), 2.63 (s, 3 H), 1.80 (s, 3 H). |
| 22 | 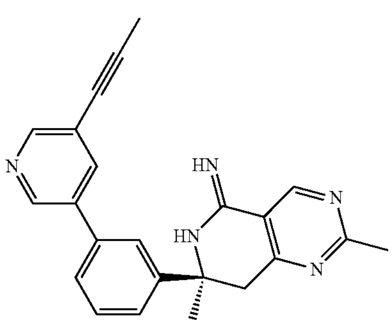 [SMILES: CC#Cc1cncc(-c2cccc([C@]3(C)Cc4nc(C)ncc4C(=N)N3)c2)c1] | δ 9.10 (s, 1 H), 8.75 (s, 1 H), 8.61 (s, 1 H), 8.23 (s, 1 H), 7.10 (s, 1 H), 7.60-7.58 (m, 1 H), 7.52-7.48 (m, 2 H), 3.85 (d, J = 16.8 Hz, 1 H), 3.60 (d, J = 16.8 Hz, 1 H), 2.70 (s, 3 H), 2.10 (s, 3 H), 1.88 (s, 3 H). |

TABLE 2-continued

| Ex. | Structure | $^1$H NMR (400 MHz, CD$_3$OD) |
| --- | --- | --- |
| 23 | 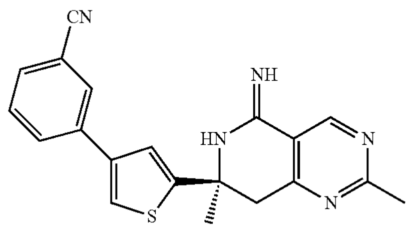 [SMILES: Cc1ncc2c(n1)C[C@@](C)(c1cc(-c3cccc(C#N)c3)cs1)NC2=N] | δ 9.2 (s, 1 H), 7.9 (s, 1 H), 7.85 (d, J = 8 Hz, 1 H), 7.7 (s, 1H), 7.63 (d, J = 6 Hz, 1 H), 7.55 (d, J = 8 Hz, 1 H), 7.45 (s, 1 H), 3.63-3.75 (m, 2 H), 2.55 (s, 3 H), 1.95 (s, 3 H). |
| 24 | 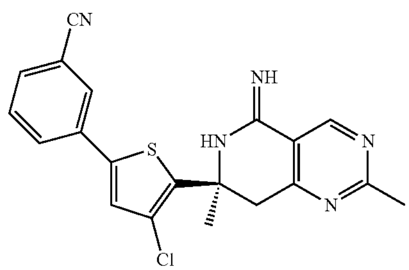 [SMILES: Cc1ncc2c(n1)C[C@@](C)(c1sc(-c3cccc(C#N)c3)cc1Cl)NC2=N] | δ 9.17 (s, 1 H), 7.90 (s, 1 H), 7.80 (d, J = 8.0 Hz, 1 H), 7.66 (d, J = 8.0 Hz, 1 H), 7.54 (t, J = 8.0 Hz, 1 H), 7.40 (s, 1 H), 4.02 (d, J = 16.8 Hz, 1 H), 3.62 (d, J = 16.8 Hz, 1 H), 2.74 (s, 3 H), 2.01 (s, 3 H). |
| 25 | 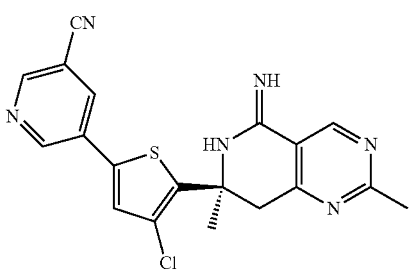 [SMILES: Cc1ncc2c(n1)C[C@@](C)(c1sc(-c3cncc(C#N)c3)cc1Cl)NC2=N] | δ 9.17 (s, 1 H), 8.94 (d, J = 2.4 Hz, 1 H), 8.81 (d, J = 1.6 Hz, 1 H), 8.35 (t, J = 2.0 Hz, 1 H), 7.52 (s, 1 H), 4.02 (d, J = 16.8 Hz, 1 H), 3.62 (d, J = 16.8 Hz, 1 H), 2.74 (s, 3 H), 2.02 (s, 3 H). |
| 26 | 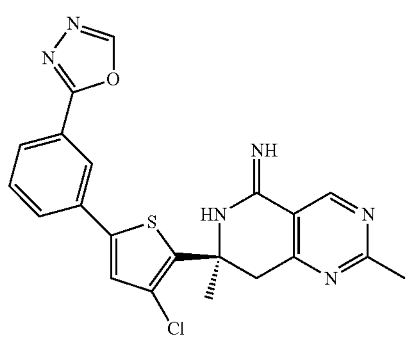 [SMILES: Cc1ncc2c(n1)C[C@@](C)(c1sc(-c3cccc(-c4nnco4)c3)cc1Cl)NC2=N] | δ 9.19 (s, 1 H), 9.04 (s, 1 H), 8.17 (s, 1 H), 7.98 (d, J = 7.6 Hz, 1 H), 7.75 (d, J = 2.0 Hz, 1 H), 7.58 (t, J = 8.0 Hz, 1 H), 7.39 (s, 1 H), 4.03 (d, J = 16.8 Hz, 1 H), 3.62 (d, J = 16.8 Hz, 1 H), 2.74 (s, 3 H), 2.02 (s, 3 H). |
| 27 | 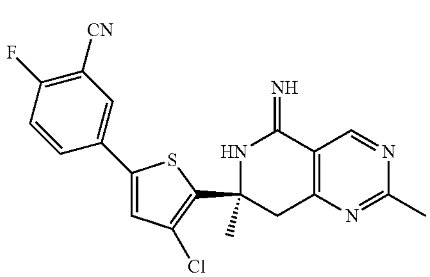 [SMILES: Cc1ncc2c(n1)C[C@@](C)(c1sc(-c3ccc(F)c(C#N)c3)cc1Cl)NC2=N] | δ 9.16 (s, 1 H), 7.91-7.94 (dd, J = 2.4 Hz, 1 H), 7.81-7.85 (m, 1 H), 7.33-7.38 (t, J = 9.6 Hz, 2 H), 4.01 (d, J = 16.8 Hz, 1 H), 3.61 (d, J = 16.8 Hz, 1 H), 2.73 (s, 3 H), 2.01 (s, 3 H). |

TABLE 2-continued

| Ex. | Structure | ¹H NMR (400 MHz, CD₃OD) |
|---|---|---|
| 28 | 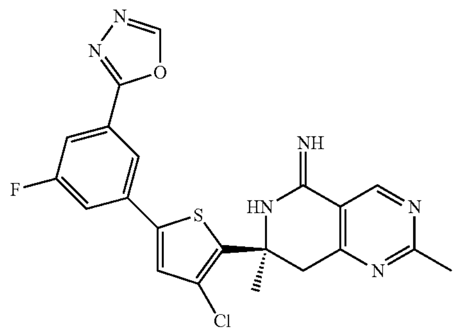 [SMILES: Cc1ncc2c(n1)C[C@@](C)(c1sc(-c3cc(F)cc(-c4nnco4)c3)cc1Cl)NC2=N] | δ 9.19 (s, 1 H), 9.04 (s, 1 H), 7.94 (s, 1 H), 7.67 (d, J = 8.4 Hz, 1 H), 7.52 (t, J = 9.2 Hz, 1 H), 7.40 (s, 1 H), 4.02 (d, J = 16.8 Hz, 1 H), 3.63 (d, J = 16.8 Hz, 1 H), 2.73 (s, 3 H), 2.03 (s, 3 H). |
| 29 | 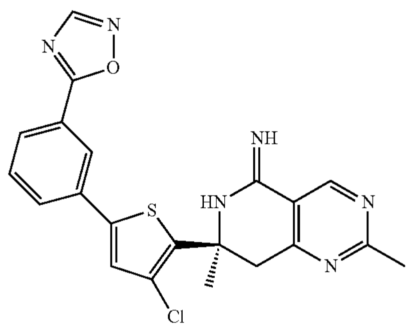 [SMILES: Cc1ncc2c(n1)C[C@@](C)(c1sc(-c3cccc(-c4ncno4)c3)cc1Cl)NC2=N] | δ 9.21 (s, 1 H), 8.05 (s, 1 H), 7.86 (s, 1 H), 7.74 (d, J = 7.2 Hz, 1 H), 7.49 (s, 1 H), 7.34 (s, 1 H), 4.05 (d, J =17.2 Hz, 1 H), 3.63 (d, J =17.2 Hz, 1 H), 2.76 (s, 3 H), 2.04 (s, 3 H). |
| 30 | 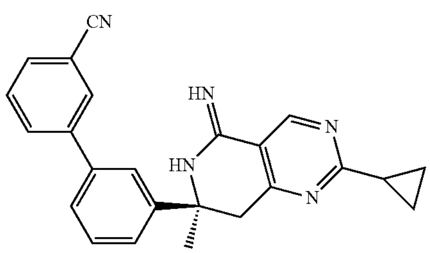 [SMILES: C[C@@]1(c2cccc(-c3cccc(C#N)c3)c2)Cc2nc(C3CC3)ncc2C(=N)N1] | δ 9.07 (s, 1 H), 7.99-7.94 (m, 2 H), 7.79-7.77 (m, 1 H), 7.72-7.67 (m, 2 H), 7.62-7.61 (m, 1 H), 7.55-7.48 (m, 2 H), 3.89 (d, J = 16.8 Hz, 1 H), 3.62 (d, J = 16.8 Hz, 1 H), 2.40-2.32 (m, 1 H), 1.94 (s, 3 H), 1.30-1.25 (m, 4 H). |
| 31 | 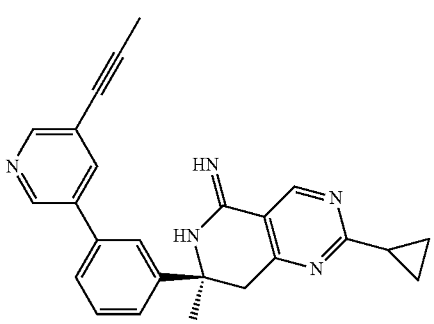 [SMILES: CC#Cc1cncc(-c2cccc([C@]3(C)Cc4nc(C5CC5)ncc4C(=N)N3)c2)c1] | δ 8.90 (s, 1 H), 8.60-8.59 (m, 1 H), 8.48-8.46 (m, 1 H), 8.02-8.01 (m, 1 H), 7.58-7.54 (m, 1 H), 7.50-7.48 (m, 1 H), 7.41-7.35 (m, 2 H), 3.72 (d, J = 16.8 Hz, 1 H), 3.45 (d, J = 16.8 Hz, 1 H), 2.21-2.15 (m, 1 H), 2.00 (s, 3 H), 1.77 (s, 3 H), 1.11-1.09 (m, 4 H). |
| 32 | 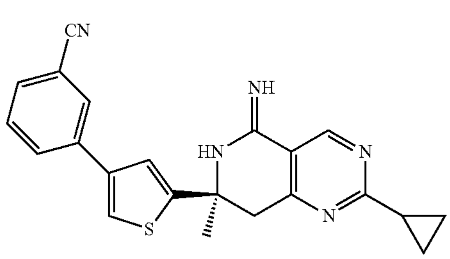 [SMILES: C[C@@]1(c2cc(-c3cccc(C#N)c3)cs2)Cc2nc(C3CC3)ncc2C(=N)N1] | δ 9.06 (s, 1 H), 7.95 (s, 1 H), 7.89-7.87 (m, 1 H), 7.69 (s, 1 H), 7.63-7.61 (m, 1 H), 7.56-7.52 (m, 1 H), 7.44 (s, 1 H), 3.68 (d, J = 17.2 Hz, 1H), 3.59 (d, J = 17.2 Hz, 1H), 2.34-2.27 (m, 1 H), 1.97 (s, 3 H), 1.23-1.21 (m, 4 H). |

TABLE 2-continued

| Ex. | Structure | ¹H NMR (400 MHz, CD₃OD) |
|---|---|---|
| 33 | 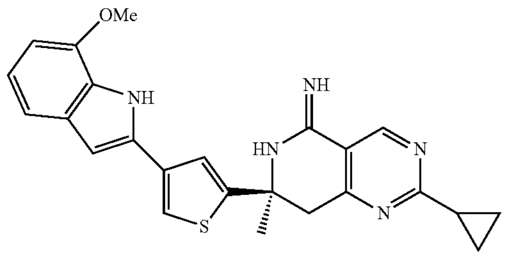 [SMILES: COc1cccc2cc(-c3csc([C@]4(C)Cc5nc(C6CC6)ncc5C(=N)N4)c3)[nH]c12] | δ 9.06 (s, 1 H), 7.60 (s, 1 H), 7.43 (s, 1 H), 7.07-7.05 (m, 1 H), 6.91-6.87 (m, 1 H), 6.62-6.57 (m, 2 H), 3.94 (s, 3 H), 3.66 (d, J = 17.2 Hz, 1H), 3.59 (d, J = 17.2 Hz, 1H), 2.34-2.26 (m, 1 H), 1.94 (s, 3 H), 1.23-1.21 (m, 4 H). |
| 34 | 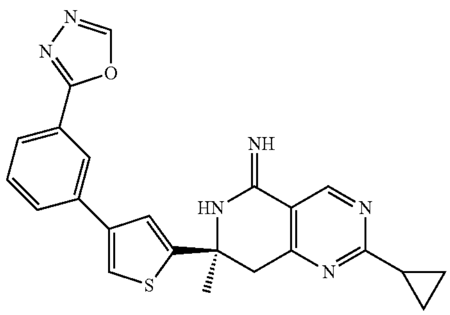 [SMILES: C[C@@]1(c2cc(-c3cccc(-c4nnco4)c3)cs2)Cc2nc(C3CC3)ncc2C(=N)N1] | δ 9.05 (d, J = 10.4 Hz, 2 H), 8.3 (s, 1 H), 8.2 (s, 1 H), 8.1 (s, 1 H), 8.0 (d, J = 7.6 Hz, 1 H), 7.82 (d, J = 7.6 Hz, 1 H), 7.76 (d, J = 8.4 Hz, 1 H), 7.70 (s, 1 H), 7.57-7.63 (m, 1 H), 7.45-7.51 (m, 1 H), 3.58-3.73 (m, 2 H), 2.29-2.32 (m, 1 H), 1.9 (s, 3 H), 1.2 (d, J = 7.6 Hz, 4 H). |
| 35 | 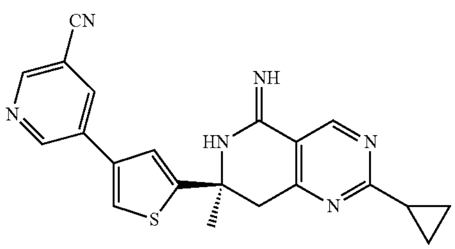 [SMILES: C[C@@]1(c2cc(-c3cncc(C#N)c3)cs2)Cc2nc(C3CC3)ncc2C(=N)N1] | δ 9.0 (d, J = 18.4 Hz, 1 H), 8.8 (s, 1 H), 8.4 (s, 1 H), 7.8 (s, 1 H), 7.5 (s, 1 H), 3.30-3.7 (m, 2 H), 2.27-2.32 (m, 1 H), 1.9 (s, 3H), 1.2 (d, J = 7.2 Hz, 4 H). |
| 36 | 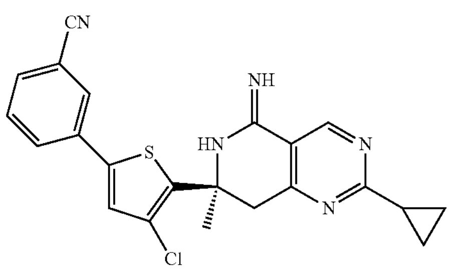 [SMILES: C[C@@]1(c2sc(-c3cccc(C#N)c3)cc2Cl)Cc2nc(C3CC3)ncc2C(=N)N1] | δ 9.06 (s, 1 H), 8.89 (s, 1 H), 7.80 (d, J = 8.0 Hz, 1 H), 7.66 (d, J = 8.0 Hz, 1 H), 7.54 (t, J = 8.0 Hz, 1 H), 7.40 (s, 1 H), 3.94-3.99 (m, 1 H), 3.53-3.57 (m, 1 H), 3.29-3.32 (m, 1 H), 2.00 (s, 3H), 1.21-1.25 (m, 4 H). |
| 37 | 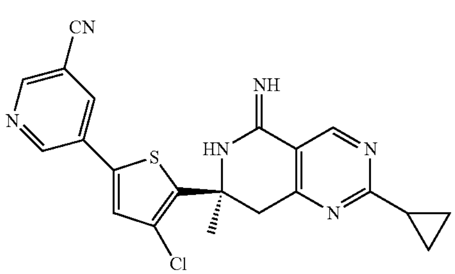 [SMILES: C[C@@]1(c2sc(-c3cncc(C#N)c3)cc2Cl)Cc2nc(C3CC3)ncc2C(=N)N1] | δ 9.06 (s, 1 H), 8.94 (s, 1 H), 8.80 (s, 1 H), 8.35 (s, 1 H), 7.52 (s, 1 H), 3.95-3.99 (m, 1 H), 3.55-3.59 (m, 1 H), 3.28-3.32 (m, 1 H), 2.00 (s, 3 H), 1.21 (m, 4 H). |

TABLE 2-continued

| Ex. | Structure | ¹H NMR (400 MHz, CD₃OD) |
|---|---|---|
| 38 | 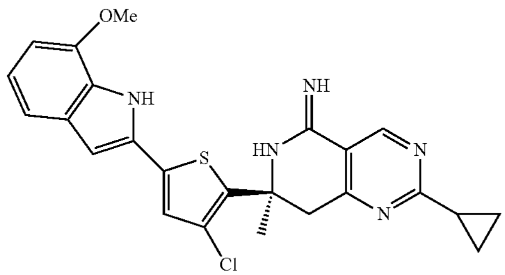 [SMILES: COc1cccc2cc(-c3cc(Cl)c([C@]4(C)Cc5nc(C6CC6)ncc5C(=N)N4)s3)[nH]c12] | δ 9.07 (s, 1 H), 7.26 (s, 1 H), 7.05 (d, J = 8.0 Hz, 1 H), 7.91 (d, J = 8.0 Hz, 1 H), 6.65 (d, J = 8.0 Hz, 1 H), 6.55 (s, 1 H), 3.93-3.98 (m, 4 H), 3.52-3.56 (m, 1 H), 3.30-3.32 (m, 1 H), 2.00 (s, 3 H), 1.22-1.24 (m, 4 H). |
| 39 | 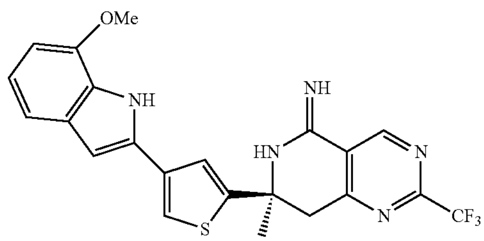 [SMILES: COc1cccc2cc(-c3csc([C@]4(C)Cc5nc(C(F)(F)F)ncc5C(=N)N4)c3)[nH]c12] | δ 9.48 (s, 1 H), 7.63 (s, 1 H), 7.49 (s, 1 H), 7.08-7.06 (m, 1 H), 6.92-6.88 (m, 1 H), 6.62-6.59 (m, 2 H), 3.94 (s, 3 H), 3.91 (d, J = 17.2 Hz, 1 H), 3.79 (d, J = 17.2 Hz, 1 H), 1.98 (s, 3 H). |
| 40 | 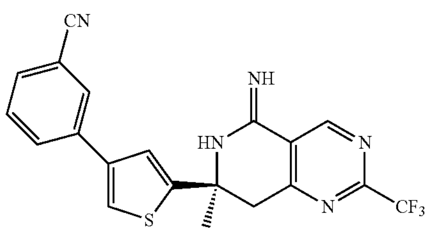 [SMILES: C[C@@]1(c2cc(-c3cccc(C#N)c3)cs2)Cc2nc(C(F)(F)F)ncc2C(=N)N1] | δ 9.47 (s, 1 H), 7.96 (s, 1 H), 7.89-7.87 (m, 1 H), 7.71 (s, 1 H), 7.63-7.61 (m, 1 H), 7.56-7.50 (m, 2 H), 3.93 (d, J = 17.2 Hz, 1 H), 3.79 (d, J = 17.2 Hz, 1 H), 1.98 (s, 3 H). |
| 41 | 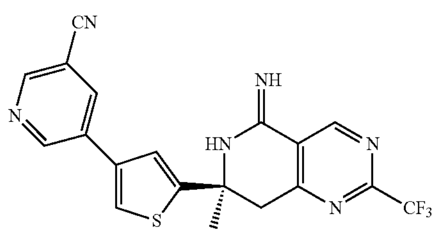 [SMILES: C[C@@]1(c2cc(-c3cncc(C#N)c3)cs2)Cc2nc(C(F)(F)F)ncc2C(=N)N1] | δ 9.48 (s, 1 H), 9.04 (s, 1 H), 8.78 (s, 1 H), 8.42 (s, 1 H), 7.88 (s, 1 H), 7.57 (s, 1 H), 3.93 (d, J = 17.2 Hz, 1 H), 3.82 (d, J = 17.2 Hz, 1 H), 2.00 (s, 3 H). |
| 42 | 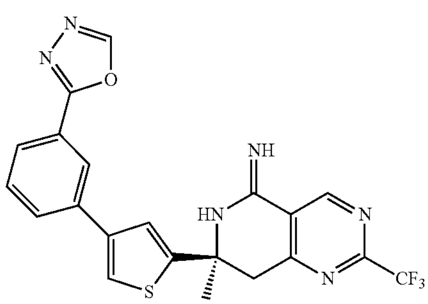 [SMILES: C[C@@]1(c2cc(-c3cccc(-c4nnco4)c3)cs2)Cc2nc(C(F)(F)F)ncc2C(=N)N1] | δ 9.48 (s, 1 H), 9.04 (s, 1 H), 8.28 (s, 1 H), 7.98-7.96 (m, 1 H), 7.84-7.82 (m, 1 H), 7.73 (s, 1 H), 7.61-7.57 (m, 1 H), 7.54 (s, 1 H), 3.96 (d, J = 17.2 Hz, 1 H), 3.80 (d, J = 17.2 Hz, 1 H), 1.99 (s, 3 H). |
| 43 | 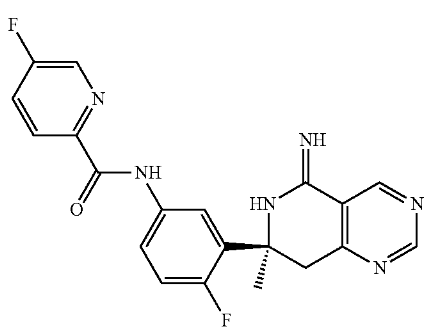 [SMILES: C[C@@]1(c2cc(NC(=O)c3ccc(F)cn3)ccc2F)Cc2ncncc2C(=N)N1] | δ 9.23 (s, 2 H), 8.56 (s, 1 H), 8.25-8.21 (m, 1 H), 7.87-7.76 (m, 2 H), 7.62-7.59 (m, 1 H), 7.18-7.12 (m, 1 H), 3.90 (d, J = 17.2 Hz, 1 H), 3.66 (d, J = 17.2 Hz, 1 H), 1.96 (s, 3 H). |

TABLE 2-continued

| Ex. | Structure | $^1$H NMR (400 MHz, CD$_3$OD) |
|---|---|---|
| 44 | 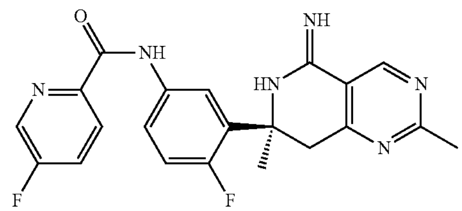 [SMILES: Cc1ncc2c(n1)C[C@@](C)(c1cc(NC(=O)c3ccc(F)cn3)ccc1F)NC2=N] | δ 9.13 (s, 1 H), 8.57 (s, 1 H), 8.23 (s, 1 H), 7.76-7.86 (m, 2 H), 7.57-7.61 (m, 1 H), 7.12-7.18 (m, 1 H), 3.59-3.85 (m, 2 H), 2.72 (s, 3 H), 1.95 (s, 3 H). |
| 45 | 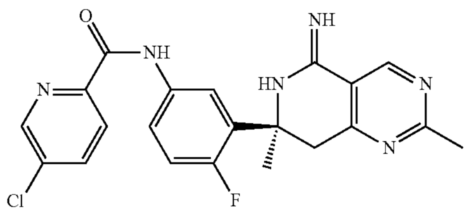 [SMILES: Cc1ncc2c(n1)C[C@@](C)(c1cc(NC(=O)c3ccc(Cl)cn3)ccc1F)NC2=N] | δ 9.13 (s, 1 H), 8.66 (s, 1 H), 8.14 (s, 1 H), 8.03-8.06 (m, 1 H), 7.83-7.86 (m, 1 H), 7.58-7.60 (m, 1 H), 7.12-7.57 (m, 1 H), 3.58-3.85 (m, 2 H), 2.72 (s, 3 H), 1.95 (s, 3 H). |
| 46 | 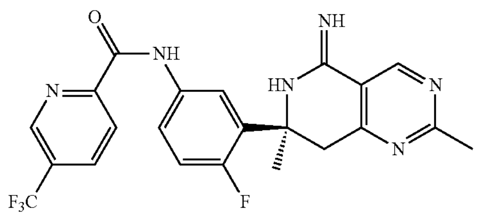 [SMILES: Cc1ncc2c(n1)C[C@@](C)(c1cc(NC(=O)c3ccc(C(F)(F)F)cn3)ccc1F)NC2=N] | δ 9.12 (s, 1 H), 8.99 (s, 1 H), 8.34 (s, 2 H), 7.87-7.89 (m, 1 H), 7.60-7.63 (m, 1 H), 7.14-7.19 (m, 1 H), 3.59-3.84 (m, 2 H), 2.72 (s, 3 H), 1.94 (s, 3 H). |
| 47 | 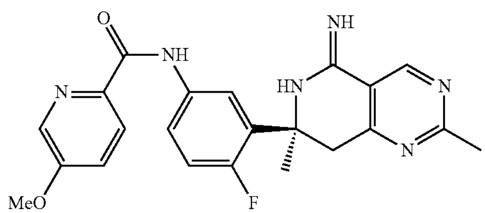 [SMILES: COc1ccc(C(=O)Nc2ccc(F)c([C@]3(C)Cc4nc(C)ncc4C(=N)N3)c2)nc1] | δ 9.13 (s, 1 H), 8.32 (s, 1 H), 8.11 (s, 1 H), 7.83-7.85 (m, 1 H), 7.49-7.59 (m, 2 H), 7.11-7.16 (m, 1 H), 3.93 (s, 3 H), 3.57-3.85 (m, 2 H), 2.72 (s, 3 H), 1.94 (s, 3 H). |
| 48 | 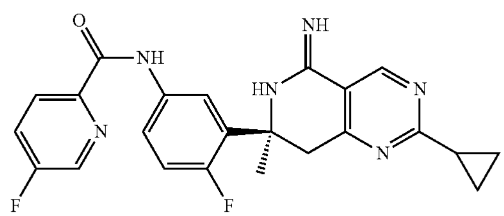 [SMILES: C[C@@]1(c2cc(NC(=O)c3ccc(F)cn3)ccc2F)Cc2nc(C3CC3)ncc2C(=N)N1] | δ 9.05 (s, 1 H), 8.56 (s, 1 H), 8.31-8.39 (m, 1 H), 7.75-7.95 (m, 2 H), 7.51-7.57 (m, 1 H), 7.12-7.17 (m, 1 H), 3.83 (d, J = 16.4 Hz, 1 H), 3.51 (d, J = 16.4 Hz, 1 H), 2.23-2.29 (m, 1 H), 1.92 (s, 3 H), 1.17-1.25 (m, 4 H). |
| 49 | 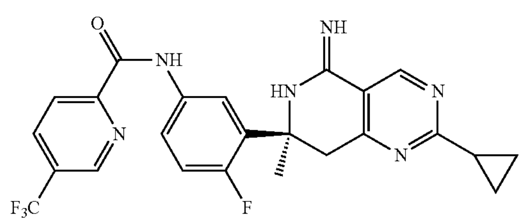 [SMILES: C[C@@]1(c2cc(NC(=O)c3ccc(C(F)(F)F)cn3)ccc2F)Cc2nc(C3CC3)ncc2C(=N)N1] | δ 9.0 (s, 2 H), 8.4 (s, 2 H), 7.91-7.93 (m, 1 H), 7.59-7.63 (m, 1H), 7.15-7.20 (m, 1 H), 3.8 (d, J = 17.2 Hz, 1 H), 3.6 (d, J = 17.2 Hz, 1 H), 2.25 (s, 1 H), 1.96 (s, 3 H), 1.2 (s, 4 H). |
| 50 | 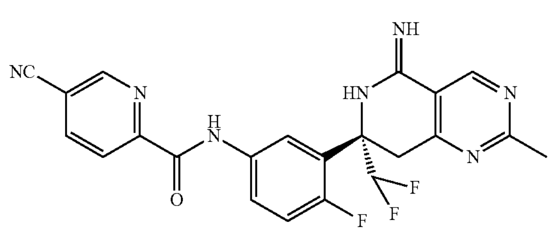 [SMILES: Cc1ncc2c(n1)C[C@](c1cc(NC(=O)c3ccc(C#N)cn3)ccc1F)(C(F)F)NC2=N] | δ 9.20 (s, 1H), 9.02 (d, J = 1.2 Hz, 1H), 8.43-8.37 (m, 1H), 8.35-8.29 (m, 1H), 8.04 (dd, J = 2.5, 7.2 Hz, 1H), 7.82-7.73 (m, 1H), 7.27 (dd, J = 9.0, 11.7 Hz, 1H), 6.88-6.57 (m, 1H), 3.94-3.79 (m, 2H), 2.74 (s, 3H). |

TABLE 2-continued

| Ex. | Structure | $^1$H NMR (400 MHz, CD$_3$OD) |
|---|---|---|
| 51 | 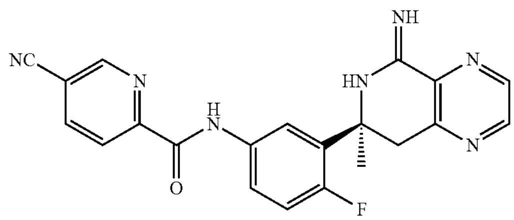 [SMILES: C[C@@]1(c2cc(NC(=O)c3ccc(C#N)cn3)ccc2F)Cc2nccnc2C(=N)N1] | δ 9.01 (s, 1H), 8.51 (d, J = 6.0 Hz, 2H), 8.41-8.35 (m, 1H), 8.33-8.27 (m, 1H), 7.81-7.75 (m, 1H), 7.73-7.66 (m, 1H), 7.07 (dd, J = 8.9, 11.9 Hz, 1H), 3.76 (d, J = 16.3 Hz, 1H), 3.42 (d, J = 16.6 Hz, 1H), 1.76 (s, 3H). |

Assays

Protocols used to determine the recited potency values for the compounds of the invention are described below.

BACE1 HTRF FRET Assay

Reagents: Na$^+$-Acetate pH 5.0; 1% Brij-35; Glycerol; Dimethyl Sulfoxide (DMSO); Recombinant human soluble BACE1 catalytic domain (>95% pure); APP Swedish mutant peptide substrate (QSY7-APP$^{swe}$-Eu): QSY7-EISEVNLDAEFC-Europium-amide.

A homogeneous time-resolved FRET assay can be used to determine IC$_{50}$ values for inhibitors of the soluble human BACE1 catalytic domain. This assay monitors the increase of 620 nm fluorescence that resulted from BACE1 cleavage of an APPswedish APP$^{swe}$ mutant peptide FRET substrate (QSY7-EISEVNLDAEFC-Europium-amide). This substrate contains an N-terminal QSY7 moiety that serves as a quencher of the C-terminal Europium fluorophore (620 nm Em). In the absence of enzyme activity, 620 nm fluorescence is low in the assay and increased linearly over 3 hours in the presence of uninhibited BACE1 enzyme. Inhibition of BACE1 cleavage of the QSY7-APP$^{swe}$-Eu substrate by inhibitors is manifested as a suppression of 620 nm fluorescence.

Varying concentrations of inhibitors at 3× the final desired concentration in a volume of 10 ul are preincubated with purified human BACE1 catalytic domain (3 nM in 10 μl) for 30 minutes at 30° C. in reaction buffer containing 20 mM Na-Acetate pH 5.0, 10% glycerol, 0.1% Brij-35 and 7.5% DSMO. Reactions are initiated by addition of 10 μl of 600 nM QSY7-APP$^{swe}$-Eu substrate (200 nM final) to give a final reaction volume of 30 μl in a 384 well Nunc HTRF plate. The reactions are incubated at 30° C. for 1.5 hours. The 620 nm fluorescence is then read on a Rubystar HTRF plate reader (BMG Labtechnologies) using a 50 millisecond delay followed by a 400 millisecond acquisition time window. Inhibitor IC$_{50}$ values are derived from non-linear regression analysis of concentration response curves. K$_i$ values are then calculated from IC$_{50}$ values using the Cheng-Prusoff equation using a previously determined μm value of 8 μM for the QSY7-APP$^{swe}$-Eu substrate at BACE1. Observed K$_i$ values for the non-limiting examples are reported in the tables above.

BACE-2 Assay

Inhibitor IC$_{50s}$ at purified human autoBACE-2 are determined in a time-resolved endpoint proteolysis assay that measures hydrolysis of the QSY7-EISEVNLDAEFC-Eu-amide FRET peptide substrate (BACE-HTRF assay). BACE-mediated hydrolysis of this peptide results in an increase in relative fluorescence (RFU) at 620 nm after excitation with 320 nm light. Inhibitor compounds, prepared at 3× the desired final concentration in 1×BACE assay buffer (20 mM sodium acetate pH 5.0, 10% glycerol, 0.1% Brij-35) supplemented with 7.5% DMSO are preincubated with an equal volume of autoBACE-2 enzyme diluted in 1×BACE assay buffer (final enzyme concentration 1 nM) in black 384-well NUNC plates for 30 minutes at 30° C. The assay is initiated by addition of an equal volume of the QSY7-EISEVNLDAEFC-Eu-amide substrate (200 nM final concentration, K$_m$=8 μM for 4 μM for autoBACE-2) prepared in 1×BACE assay buffer supplemented with 7.5% DMSO and incubated for 90 minutes at 30° C. DMSO is present at 5% final concentration in the assay. Following laser excitation of sample wells at 320 nm, the fluorescence signal at 620 nm is collected for 400 ms following a 50 μs delay on a RUBYstar HTRF plate reader (BMG Labtechnologies). Raw RFU data is normalized to maximum (1.0 nM BACE/DMSO) and minimum (no enzyme/DMSO) RFU values. IC$_{50s}$ are determined by nonlinear regression analysis (sigmoidal dose response, variable slope) of percent inhibition data with minimum and maximum values set to 0 and 100 percent respectively. Similar IC$_{50s}$ are obtained when using raw RFU data. The K$_i$ values are calculated from the IC$_{50}$ using the Cheng-Prusoff equation.

We claim:

1. A compound, or a pharmaceutically acceptable salt thereof, said compound having the structural Formula (I):

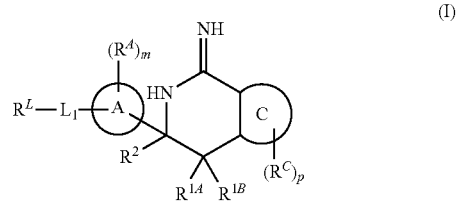

(I)

or a tautomer thereof having the structural Formula (I'):

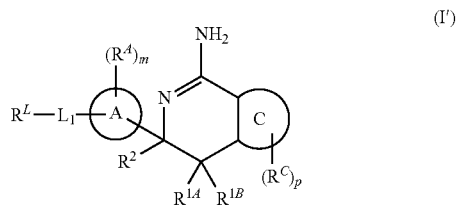

(I')

wherein:

-L$_1$- is a bond or the divalent moiety —C(O)NH—;

R$^{1A}$ and R$^{1B}$ are each independently selected from the group consisting of H, halogen, alkyl, and cycloalkyl, wherein said alkyl and said cycloalkyl are optionally substituted with one or more fluorine, and wherein 1 to 2 non-adjacent, non-terminal carbon atoms in said alkyl are optionally independently replaced with —O—, —NH—, —N(alkyl)-, —S—, —S(O)—, or —S(O)$_2$—;

$R^2$ is selected from the group consisting of H, alkyl, cycloalkyl, -alkyl-cycloalkyl, heterocycloalkyl, and -alkyl-heterocycloalkyl,
wherein said alkyl, cycloalkyl, -alkyl-cycloalkyl, heterocycloalkyl, and -alkyl-heterocycloalkyl are optionally substituted with one or more halogen, and
wherein 1 to 2 non-adjacent, non-terminal carbon atoms in said alkyl are optionally independently replaced with —O—, —NH—, —N(alkyl)-, —S—, —S(O)—, or —S(O)$_2$—;

ring A is selected from the group consisting of aryl and heteroaryl;
m is 0 or more, with the proviso that the value of m does not exceed the number of available substitutable hydrogen atoms on ring A;
each $R^A$ (when present) is independently selected from the group consisting of halogen, oxo, —OH, —CN, alkyl, —O-alkyl, and cycloalkyl,
wherein said alkyl, —O-alkyl, and cycloalkyl of $R^A$ are each optionally independently unsubstituted or substituted with one or more fluorine, and
wherein 1 to 2 non-adjacent, non-terminal carbon atoms in said alkyl are optionally independently replaced with —O—, —NH—, —N(alkyl)-, —S—, —S(O)—, or —S(O)$_2$—;

$R^L$ is alkyl,
wherein said alkyl is optionally further substituted with one or more halogen, and
wherein 1 to 2 non-adjacent, non-terminal carbon atoms in said alkyl are optionally independently replaced with —O—, —NH—, —N(alkyl)-, —S—, —S(O)—, or —S(O)$_2$—;
or, alternatively, $R^L$ is a moiety having the formula

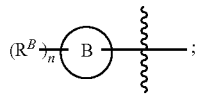

wherein
ring B is selected from the group consisting of aryl, heteroaryl, cycloalkyl, and heterocycloalkyl;
n is 0 or more, with the proviso that the value of n does not exceed the number of available substitutable hydrogen atoms on ring b; and
each $R^B$ (when present) is independently selected from the group consisting of halogen, oxo, —OH, —CN, —SF$_5$, —OSF$_5$, —OR$^{3B}$, —SR$^{3B}$, alkyl, alkenyl, alkynyl, cycloalkyl, -alkyl-cycloalkyl, heterocycloalkyl, -alkyl-heterocycloalkyl, aryl, and heteroaryl,
wherein said alkyl, alkenyl, alkynyl, cycloalkyl, -alkyl-cycloalkyl, heterocycloalkyl, -alkyl-heterocycloalkyl, aryl, and heteroaryl of $R^B$ are each optionally independently unsubstituted or substituted with one or more groups independently selected from $R^4$, and wherein 1 to 2 non-adjacent, non-terminal carbon atoms in said alkyl are optionally independently replaced with —O—, —NH—, —N(alkyl)-, —S—, —S(O)—, or —S(O)$_2$—;
ring C is selected from the group consisting of pyrazinyl, pyrimidinyl, and pyridazinyl;

p is 0 or more, with the proviso that the value of p does not exceed the number of available substitutable hydrogen atoms on ring C; and
each $R^c$ (when present) is independently selected from the group consisting of alkyl and cycloalkyl,
wherein said alkyl and cycloalkyl are each optionally substituted with one to three fluorine, and
wherein 1 to 2 non-adjacent, non-terminal carbon atoms in said alkyl are optionally independently replaced with —O—, —NH—, —N(alkyl)-, —S—, —S(O)—, or —S(O)$_2$—;

each $R^{3B}$ is independently selected from the group consisting of H, alkyl, alkenyl, alkynyl, cycloalkyl, -alkyl-cycloalkyl, heterocycloalkyl, and -alkyl-heterocycloalkyl,
wherein each said alkyl, alkenyl, alkynyl, cycloalkyl, -alkyl-cycloalkyl, heterocycloalkyl, and -alkyl-heterocycloalkyl of $R^{3B}$ is unsubstituted or optionally substituted with one or more fluorine, and
wherein 1 to 2 non-adjacent, non-terminal carbon atoms in said alkyl are optionally independently replaced with —O—, —NH—, —N(alkyl)-, —S—, —S(O)—, or —S(O)$_2$—; and each $R^4$ (when present) is independently selected from the group consisting of halogen, —OH, —CN, alkyl, alkoxy, cycloalkyl, -alkyl-cycloalkyl, —O-cycloalkyl, -heterocycloalkyl, and -alkyl-heterocycloalkyl,
wherein each said alkyl, alkoxy, cycloalkyl, -alkyl-cycloalkyl, —O—cycloalkyl, -heterocycloalkyl, and -alkyl-heterocycloalkyl are optionally substituted with one or more fluorine, and
wherein 1 to 2 non-adjacent, non-terminal carbon atoms in said alkyl are optionally independently replaced with —O—, —NH—, —N(alkyl)-, —S—, —S(O)—, or —S(O)$_2$—.

2. A compound of claim 1, or a tautomer thereof, or a pharmaceutically acceptable salt of said compound or said tautomer, wherein:
$R^{1A}$ is selected from the group consisting of H and fluorine;
$R^{1B}$ is selected from the group consisting of H and fluorine; and
$R^2$ is selected from the group consisting of methyl and —CHF$_2$.

3. A compound of claim 2, or a tautomer thereof, or a pharmaceutically acceptable salt of said compound or said tautomer, wherein:
ring C is selected from the group consisting of pyrazine and pyrimidine;
p is 0 or 1; and
$R^C$ (when present) is independently selected from the group consisting of methyl, ethyl, —CF$_3$, —CHF$_2$, —CH$_2$F, —CH$_2$OCH$_3$, and cyclopropyl.

4. A compound of claim 3, or a tautomer thereof, or a pharmaceutically acceptable salt of said compound or said tautomer, wherein:
ring A is selected from the group consisting of phenyl, pyridazinyl, pyridinyl, pyrimidinyl, pyrazinyl, pyrazolyl, triazinyl, thiazolyl, and thienyl;
m is 0, 1, 2, or 3, with the proviso that the value of m does not exceed the number of available substitutable hydrogen atoms on ring A; and
each $R^A$ (when present) is independently selected from the group consisting of fluoro, chloro, bromo, —CN, —OCH$_3$, —CH$_2$OCH$_3$, methyl, ethyl, cyclopropyl, —CF$_3$, —CHF$_2$, —CH$_2$F, —OCF$_3$, and —OCHF$_2$.

5. A compound of claim 4, or a tautomer thereof, or a pharmaceutically acceptable salt of said compound or said tautomer, wherein:

$R^L$ is selected from the group consisting of methyl, ethyl, —CF$_3$, —CHF$_2$, —CH$_2$F, —CH$_2$CF$_3$, —CF$_2$CH$_3$, —CH$_2$OCH$_3$, —CH$_2$OCH$_2$CH$_3$, —CH$_2$CH$_2$OCH$_3$, —CH(OCH$_3$)CH$_3$, —CH$_2$SCH$_3$, —CH$_2$N(CH$_3$)$_2$, —CH$_2$OCF$_3$, and —CH$_2$OCHF$_2$.

6. A compound of claim 5, or a tautomer thereof, or a pharmaceutically acceptable salt of said compound or said tautomer, wherein:

-L$_1$- is a bond.

7. A compound of claim 5, or a tautomer thereof, or a pharmaceutically acceptable salt of said compound or said tautomer, wherein:

-L$_1$- is the divalent moiety —C(O)NH—.

8. A compound of claim 4, or a tautomer thereof, or a pharmaceutically acceptable salt of said compound or said tautomer, wherein:

$R^L$ is a moiety having the formula

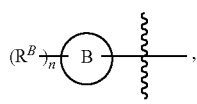

wherein:

ring B is selected from the group consisting of cyclobutyl, cyclopropyl, furanyl, imidazopyridinyl, imidazopyrimidinyl, imidazothiazolyl, indolyl, isothiazolyl, isoxazolyl, oxadiazolyl, oxazolyl, oxetanyl, phenyl, pyrazinyl, pyrazolyl, pyridazinyl, pyridinyl, pyrimidinyl, pyrrolyl, tetrahydrofuranyl, tetrahydropyranyl, thiadiazolyl, thiazolyl, and thienyl;

each $R^B$ group (when present) is independently selected from the group consisting of fluoro, chloro, —CN, —OCH$_3$, —O—CH$_2$-cyclopropyl, —OCH$_2$—C≡C—H, —OCH$_2$—C≡C—CH$_3$, methyl, ethyl, cyclopropyl, —CH$_2$-cyclopropyl, —CH$_2$OCH$_3$, —C≡CH, —C≡C—CH$_3$, —CF$_3$, —CHF$_2$, —OCF$_3$, —OCHF$_2$, oxadiazolyl, isoxazolyl, and oxazolyl, wherein each said oxadiazolyl, isoxazolyl, and oxazolyl is optionally substituted with one substituent from the group consisting of fluoro and methyl; and n is 0, 1, 2, or 3, with the proviso that the value of n does not exceed the number of available substitutable hydrogen atoms on ring B.

9. A compound of claim 8, or a tautomer thereof, or a pharmaceutically acceptable salt of said compound or said tautomer, wherein:

-L$_1$- is a bond.

10. A compound of claim 8, or a tautomer thereof, or a pharmaceutically acceptable salt of said compound or said tautomer, wherein:

-L$_1$- is the divalent moiety —C(O)NH—.

11. A compound of claim 1, or a tautomer thereof, or a pharmaceutically acceptable salt of said compound or said tautomer, said compound selected from the group consisting of:

| Structure |
|---|
| 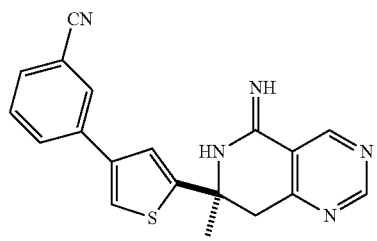 |
| 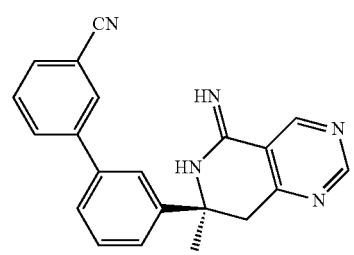 [SMILES: C[C@@]1(c2cccc(-c3cccc(C#N)c3)c2)Cc2ncncc2C(=N)N1] |
| 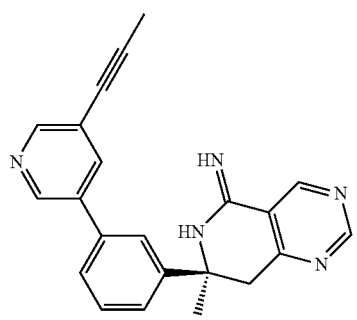 [SMILES: CC#Cc1cncc(-c2cccc([C@]3(C)Cc4ncncc4C(=N)N3)c2)c1] |
| 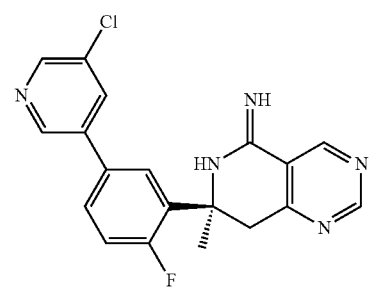 |
| 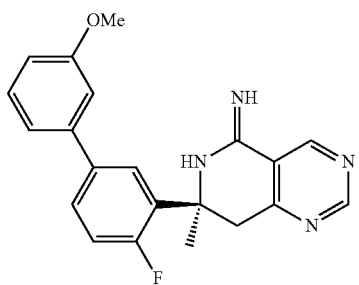 |

| 111 -continued | 112 -continued |
|---|---|
| Structure | Structure |
| 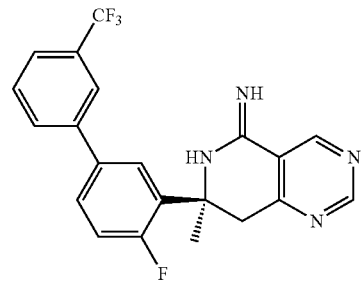 [SMILES: C[C@@]1(c2cc(-c3cccc(C(F)(F)F)c3)ccc2F)Cc2ncncc2C(=N)N1] | 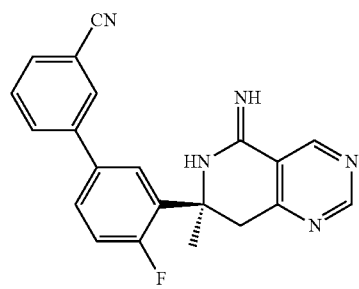 |
| 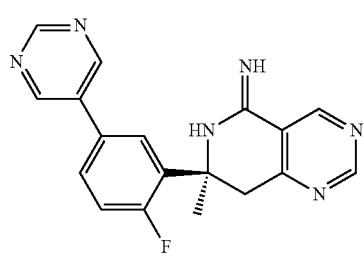 [SMILES: C[C@@]1(c2cc(-c3cncnc3)ccc2F)Cc2ncncc2C(=N)N1] | 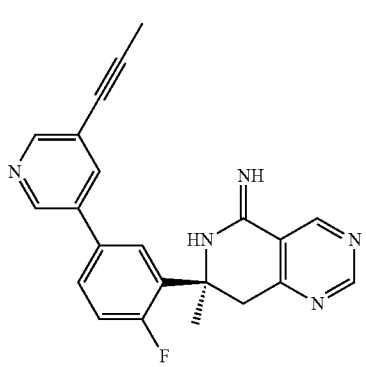 |
| 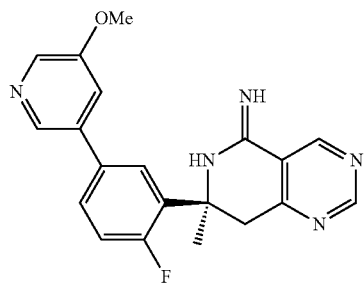 [SMILES: COc1cncc(-c2ccc(F)c([C@]3(C)Cc4ncncc4C(=N)N3)c2)c1] | 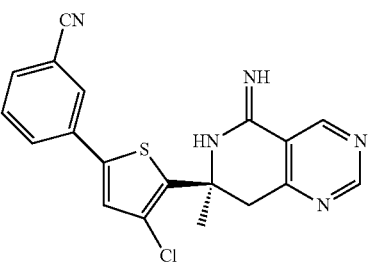 [SMILES: C[C@@]1(c2sc(-c3cccc(C#N)c3)cc2Cl)Cc2ncncc2C(=N)N1] |
| 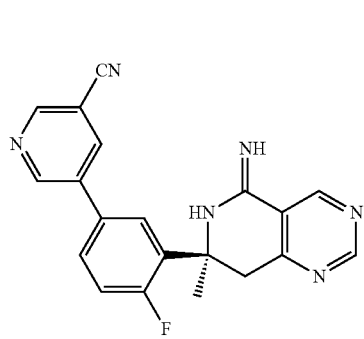 | 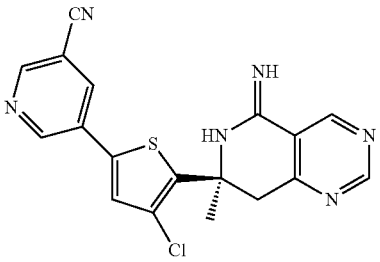 [SMILES: C[C@@]1(c2sc(-c3cncc(C#N)c3)cc2Cl)Cc2ncncc2C(=N)N1] |
| 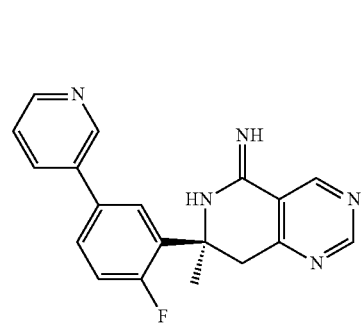 | 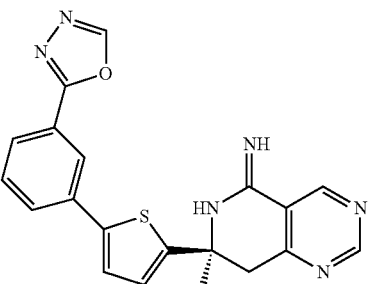 |

| 113 -continued | 114 -continued |
|---|---|
| Structure | Structure |
| 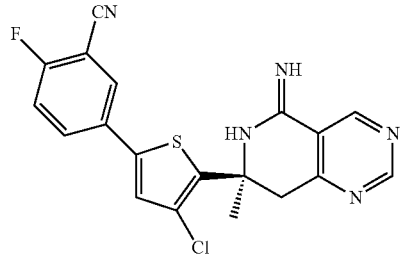 [SMILES: C[C@@]1(c2sc(-c3ccc(F)c(C#N)c3)cc2Cl)Cc2ncncc2C(=N)N1] | 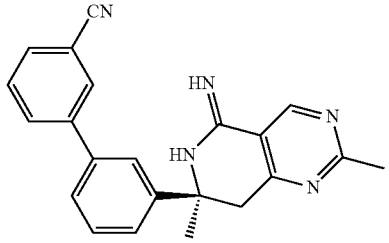 |
| 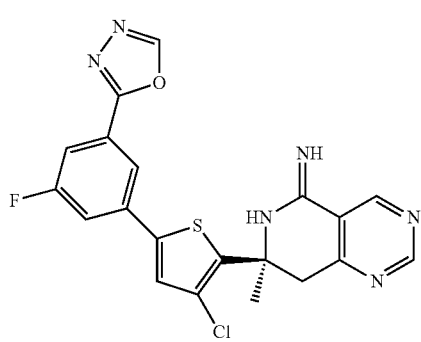 [SMILES: C[C@@]1(c2sc(-c3cc(F)cc(-c4nnco4)c3)cc2Cl)Cc2ncncc2C(=N)N1] | 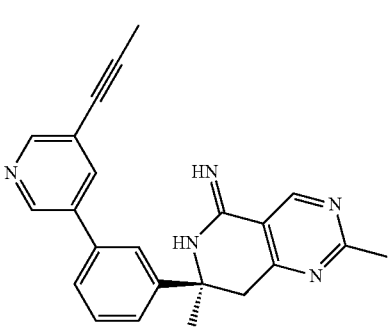 |
| 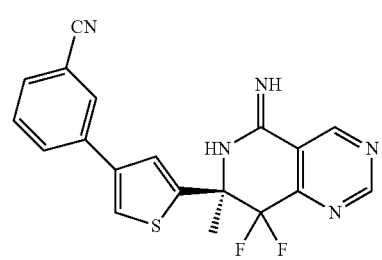 [SMILES: C[C@]1(c2cc(-c3cccc(C#N)c3)cs2)NC(=N)c2cncnc2C1(F)F] | 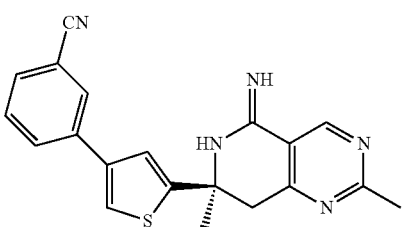 |
| 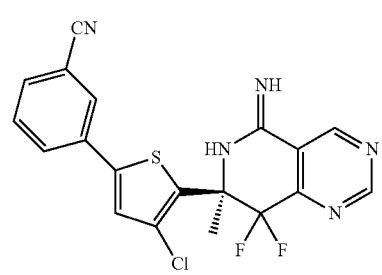 [SMILES: C[C@]1(c2sc(-c3cccc(C#N)c3)cc2Cl)NC(=N)c2cncnc2C1(F)F] | 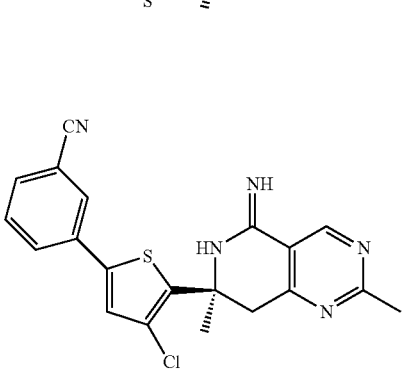 |
| 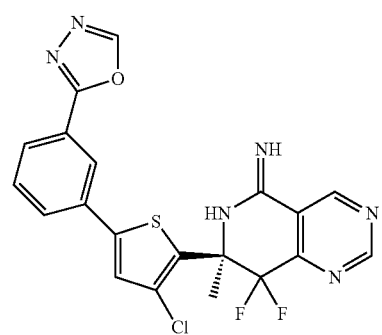 [SMILES: C[C@]1(c2sc(-c3cccc(-c4nnco4)c3)cc2Cl)NC(=N)c2cncnc2C1(F)F] | 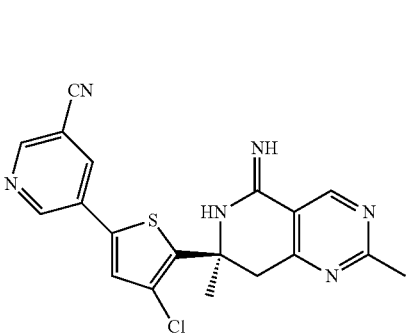 [SMILES: Cc1ncc2c(n1)C[C@@](C)(c1sc(-c3cncc(C#N)c3)cc1Cl)NC2=N] |

| 115 -continued | 116 -continued |
|---|---|
| Structure | Structure |
| 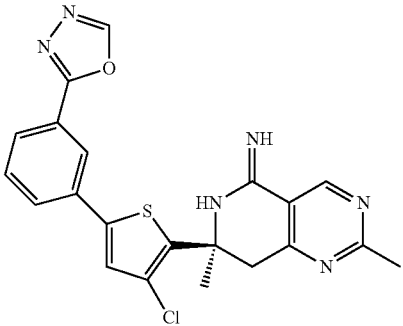 [SMILES: Cc1ncc2c(n1)C[C@@](C)(c1sc(-c3cccc(-c4nnco4)c3)cc1Cl)NC2=N] | 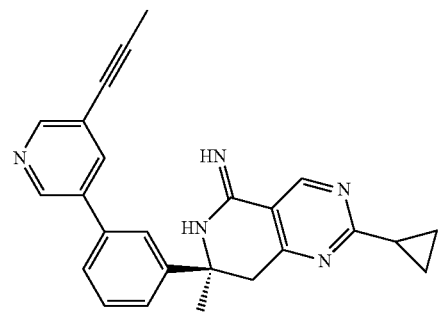 |
| 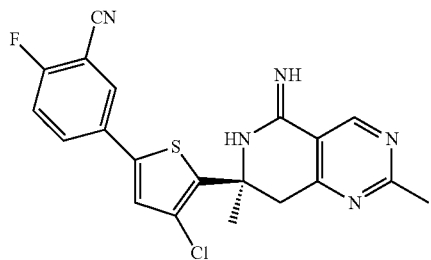 [SMILES: Cc1ncc2c(n1)C[C@@](C)(c1sc(-c3ccc(F)c(C#N)c3)cc1Cl)NC2=N] | 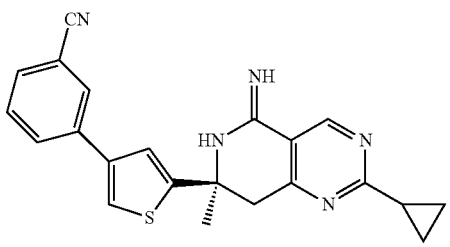 |
| 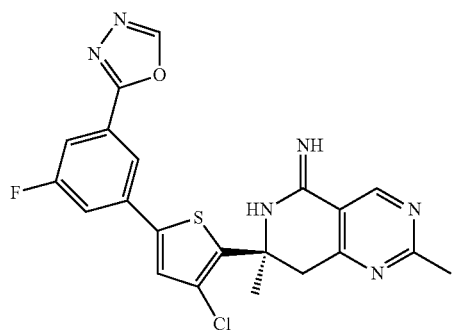 [SMILES: Cc1ncc2c(n1)C[C@@](C)(c1sc(-c3cc(F)cc(-c4nnco4)c3)cc1Cl)NC2=N] | 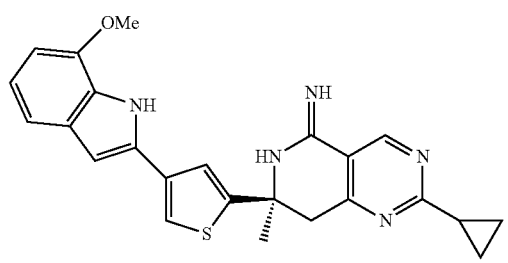 |
| 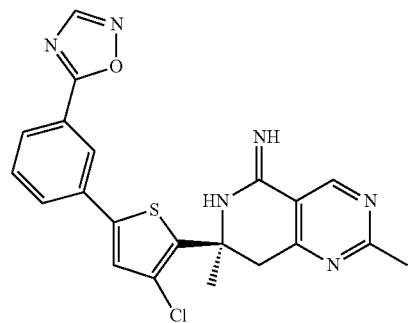 [SMILES: Cc1ncc2c(n1)C[C@@](C)(c1sc(-c3cccc(-c4ncno4)c3)cc1Cl)NC2=N] | 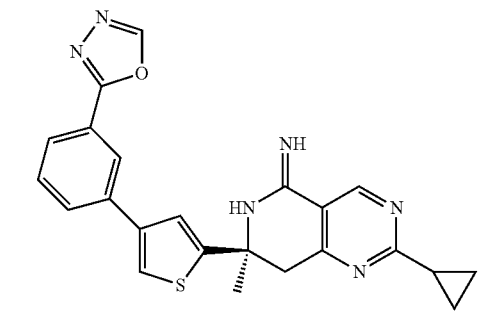 |
| 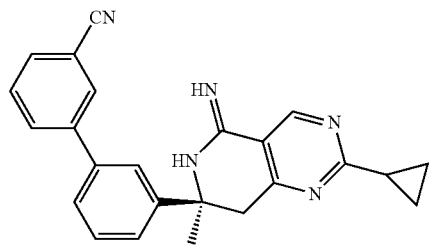 [SMILES: C[C@@]1(c2cccc(-c3cccc(C#N)c3)c2)Cc2nc(C3CC3)ncc2C(=N)N1] | 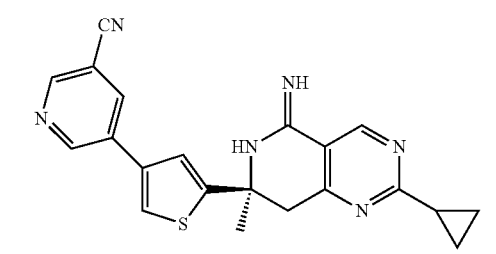 [SMILES: C[C@@]1(c2cc(-c3cncc(C#N)c3)cs2)Cc2nc(C3CC3)ncc2C(=N)N1] |

| 117 -continued | 118 -continued |
|---|---|
| Structure | Structure |
| 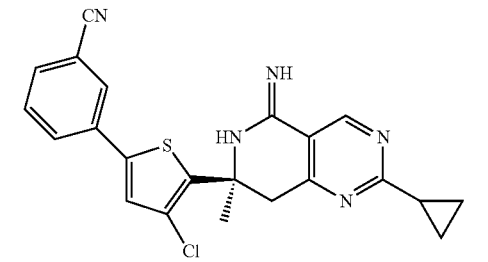 [SMILES: C[C@@]1(c2sc(-c3cccc(C#N)c3)cc2Cl)Cc2nc(C3CC3)ncc2C(=N)N1] | 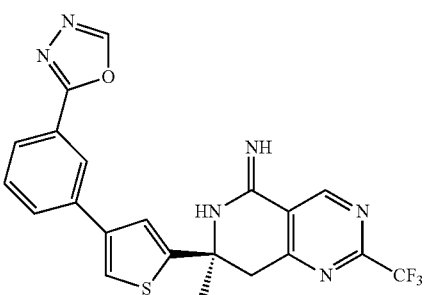 |
| 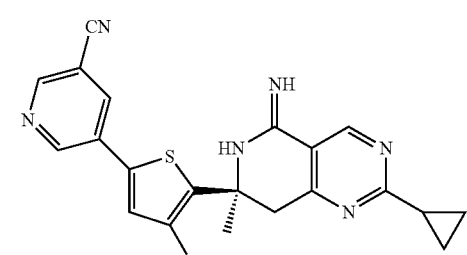 | 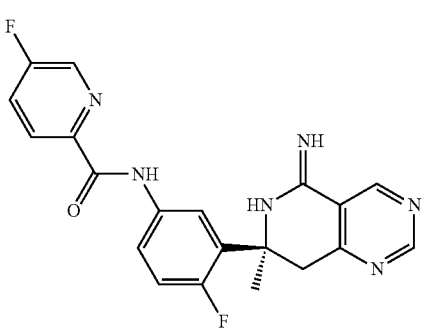 |
| 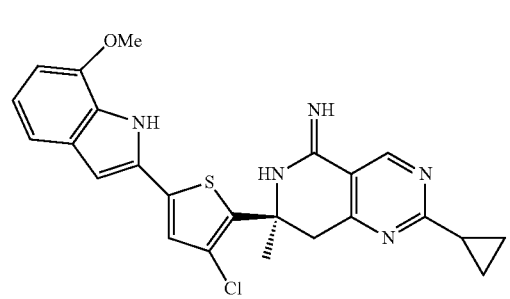 [SMILES: COc1cccc2cc(-c3cc(Cl)c([C@]4(C)Cc5nc(C6CC6)ncc5C(=N)N4)s3)[nH]c12] | 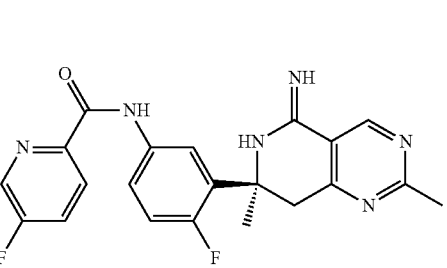 |
| 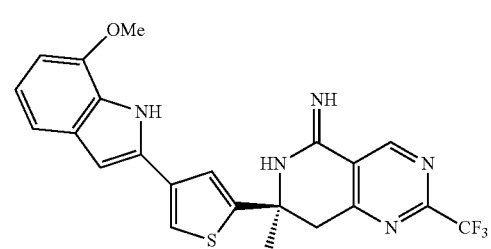 [SMILES: COc1cccc2cc(-c3csc([C@]4(C)Cc5nc(C(F)(F)F)ncc5C(=N)N4)c3)[nH]c12] | 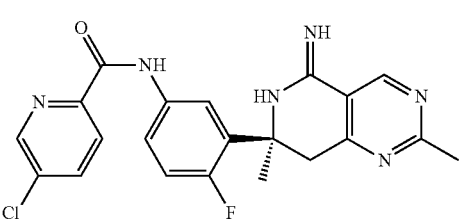 |
| 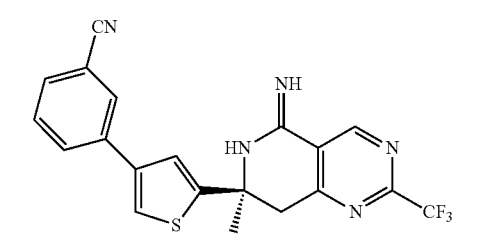 [SMILES: C[C@@]1(c2cc(-c3cccc(C#N)c3)cs2)Cc2nc(C(F)(F)F)ncc2C(=N)N1] | 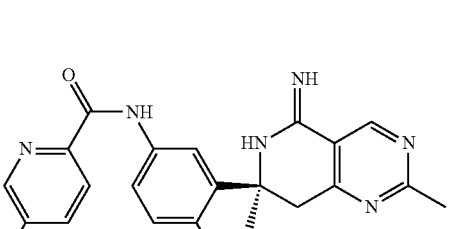 |
| 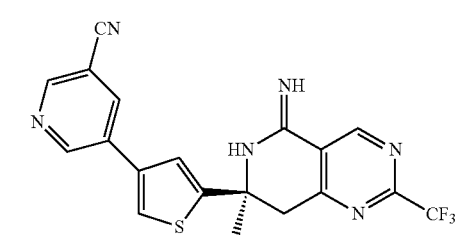 | |

| Structure | | Structure |
|---|---|---|
| 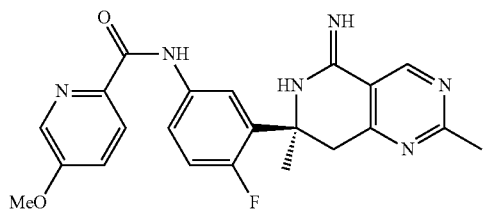 [SMILES: COc1ccc(C(=O)Nc2ccc(F)c([C@]3(C)Cc4nc(C)ncc4C(=N)N3)c2)nc1] | | 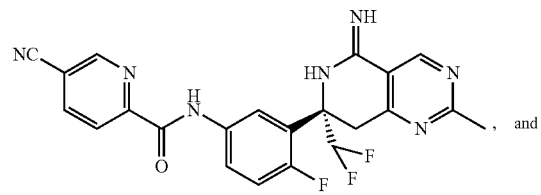 [SMILES: Cc1ncc2c(n1)C[C@](c1cc(NC(=O)c3ccc(C#N)cn3)ccc1F)(C(F)F)NC2=N], and |
| 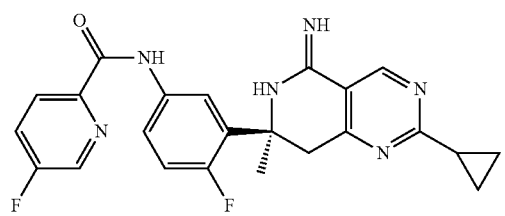 | | 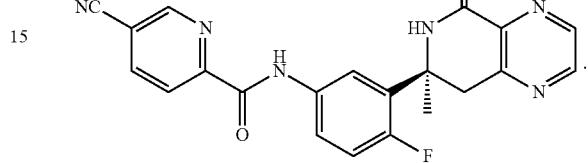 |
| 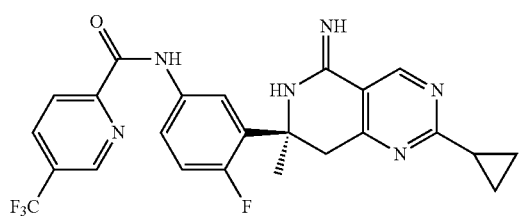 | | |

12. A pharmaceutical composition comprising a compound according to claim 1, or a tautomer thereof, or a pharmaceutically acceptable salt of said compound or said tautomer, and a pharmaceutically acceptable carrier or diluent.

13. A compound according to claim 1, or a tautomer thereof, or pharmaceutically acceptable salt of said compound or said tautomer, for use as a medicament.

* * * * *